US009346882B2

(12) United States Patent
Mataraza et al.

(10) Patent No.: US 9,346,882 B2
(45) Date of Patent: May 24, 2016

(54) FULLY HUMAN ANTIBODIES TO BTLA

(71) Applicant: MEDAREX, L.L.C., Princeton, NJ (US)

(72) Inventors: Jennifer Marie Mataraza, Cambridge, MA (US); Andrea Van Elsas, Oss (NL); Alan J. Korman, Piedmont, CA (US); Edward L. Halk, Sunnyvale, CA (US); Kent B. Thudium, Oakland, CA (US); Mark J. Selby, San Francisco, CA (US); Timothy W. Sproul, Livermore, CA (US); Heidi N. Leblanc, Mountain View, CA (US)

(73) Assignee: E. R. SQUIBB & SONS, L.L.C., Princeton, NJ (US)

( * ) Notice: Subject to any disclaimer, the term of this patent is extended or adjusted under 35 U.S.C. 154(b) by 111 days.

(21) Appl. No.: 14/031,319

(22) Filed: Sep. 19, 2013

(65) Prior Publication Data

US 2014/0017255 A1    Jan. 16, 2014

Related U.S. Application Data

(62) Division of application No. 13/388,028, filed as application No. PCT/US2010/043182 on Jul. 26, 2010, now Pat. No. 8,563,694.

(60) Provisional application No. 61/230,332, filed on Jul. 31, 2009, provisional application No. 61/257,612, filed on Nov. 3, 2009.

(51) Int. Cl.
*C07K 16/28* (2006.01)
*C12N 15/11* (2006.01)
*C12N 15/79* (2006.01)
*C12N 15/00* (2006.01)

(52) U.S. Cl.
CPC ......... *C07K 16/2803* (2013.01); *C07K 16/2818* (2013.01); *C07K 2317/24* (2013.01); *C07K 2317/56* (2013.01); *C07K 2317/565* (2013.01); *C07K 2317/73* (2013.01); *C07K 2317/77* (2013.01)

(58) Field of Classification Search
None
See application file for complete search history.

(56) References Cited

U.S. PATENT DOCUMENTS

| 8,563,694 B2 | 10/2013 | Mataraza et al. |
| 2007/0025992 A1 | 2/2007 | Takayama et al. |
| 2008/0187531 A1 | 8/2008 | Babcook et al. |
| 2010/0104559 A1 | 4/2010 | Ware et al. |

FOREIGN PATENT DOCUMENTS

WO   2008/076560 A2   6/2008

OTHER PUBLICATIONS

Ansari, Mohammed Javeed I. et al., "The Programmed Death-1 (PD-1) Pathway Regulates Autoimmune Diabetes in Nonobese Diabetic (NOD) Mice," J. Exp. Med., vol. 198(1):63-69 (2003).

Compaan, Deanne M. et al., "Attenuating Lymphocyte Activity, the Crystal Structure of the BTLA-HVEM Complex," The Journal of Biological Chemistry, vol. 280(47):39553-39561 (2005).

Deppong, Christine et al., "Cutting Edge: B and T Lymphocyte Attenuator and Programmed Death Receptor-1 Inhibitory Receptors Are Required for Termination of Acute Allergic Airway Inflammation," The Journal of Immunology, vol. 176:3909-3913 (2006).

Derre, Laurent et al., "BTLA mediates inhibition of human tumor-specific CD8+ T cells that can be partially reversed by vaccination," The Journal of Clinical Investigation, vol. 120(1):157-167 (2010).

Gurka, Stephanie et al., "Generation of Novel Anti-BTLA Monoclonal Antibodies for In Vivo Use and Their Functional Testing at Near-physiological Conditions," Hybridoma, vol. 28(6):405-414 (2009).

Han, Peggy et al., "An Inhibitory Ig Superfamily Protein Expressed by Lymphocytes and APCs Is Also an Early Marker of Thymocyte Positive Selection," The Journal of Immunology, vol. 172:5931-5939 (2004).

Harrop, Jeremy A. et al., "Herpesvirus Entry Mediator Ligand (HVEM-L), a Novel Ligand for HVEM/TR2, Stimulates Proliferation of T Cells and Inhibits HT29 Cell Growth," The Journal of Biological Chemistry, vol. 273(42):27548-27556 (1998).

Krieg, Carsten et al., "Functional Analysis of B and T Lymphocyte Attenuator Engagement of CD4+ and CD8+ T Cells," The Journal of Immunology, vol. 175:6420-6427 (2005).

Lin, Shih-Chang et al., "Association of a BTLA gene polymorphism with the risk of rheumatoid arthritis," Journal of Biomedical Science, vol. 13:853-860 (2006).

Oya, Yoshihiro et al., "Development of Autoimmune Hepatitis-Like Disease and Production of Autoantibodies to Nuclear Antigens in Mice Lacking B and T Lymphocyte Attenuator," Arthritis & Rheumatism, vol. 58(8):2498-2510 (2008).

Presta, Leonard G., "Engineering Antibodies for Therapy," Current Pharmaceutical Biotechnology, vol. 3:237-256 (2002).

Sedy, John R. et al., "B and T lymphocyte attenuator regulates T cell activation through interaction with herpesvirus entry mediator," Nature Immunology, vol. 6(1):90-98 (2005).

Stebbings, Richard et al., "'Cytokine Storm' in the Phase I Trial of Monoclonal Antibody TGN1412: Better Understanding the Causes to Improve PreClinical Testing of Immunotherapeutics," The Journal of Immunology, vol. 179:3325-3331 (2007).

(Continued)

*Primary Examiner* — Ilia Ouspenski
(74) *Attorney, Agent, or Firm* — Nelson Mullins Riley & Scarborough LLP; Jane E. Remillard, Esq.; Jill Gorny Sloper, Esq.

(57) ABSTRACT

The present invention relates to binding compounds specific for BTLA and uses thereof. More specifically, the invention relates to fully human antibodies that recognize human BTLA and modulate its activity in cancer, inflammatory, and autoimmune disorders.

22 Claims, 25 Drawing Sheets

(56) References Cited

OTHER PUBLICATIONS

Steinberg, Marcos W. et al., "A crucial role for HVEM and BTLA in preventing intestinal inflammation," J. Exp. Med., vol. 205(6):1463-1476 (2008).
Truong, Wayne et al., "BTLA targeting modulates lymphocyte phenotype, function, and numbers and attenuates disease in nonobese diabetic mice," Journal of Leukocyte Biology, vol. 86:41-51 (2009).
Truong, W. et al., "Combined Coinhibitory and Costimulatory Modulation with Anti-BTLA and CTLA4Ig Facilitates Tolerance in Murine Islet Allografts," American Journal of Transplantation, vol. 7:2663-2674 (2007).
Vendel, Andrew C. et al., "B and T Lymphocyte Attenuator Regulates B Cell Receptor Signaling by Targeting Syk adn BLNK," The Journal of Immunology, vol. 182:1509-1517 (2009).
Watanabe, Norihiko et al., "BTLA is a lymphocyte inhibitory receptor with similarities to CTLA-4 and PD-1," Nature Immunology, vol. 4(7):670-679 (2003).
International Preliminary Report on Patentability and Written Opinion for Application No. PCT/US2010/043182, 10 pages, dated Jan. 31, 2012.
International Search Report for Application No. PCT/US2010/043182, 5 pages, dated Dec. 21, 2010.

FIGURE 1A

Anti- BTLA 8D5 VH

```
V segment:      3-13
D segment:      ND
J segment:      JH6b
```

```
      E   V   Q   L   V   E   S   G   G   G   L   V   Q   P   G   G   S   L
  1 GAG GTG CAG CTG GTG GAG TCT GGG GGA GGC TTG GTA CAG CCG GGG GGG TCC CTG
                                                                    CDR1
                                                                ~~~~~~~~~~~~~~~~~~~
      R   L   S   C   A   A   S   G   F   T   I   S   S   Y   D   M   H   W
 55 AGA CTC TCC TGT GCA GCC TCT GGA TTC ACC ATC AGT AGT TAC GAC ATG CAC TGG
                                                                    CDR2
                                                                ~~~~~~~~~~~~~~~~~~~~
      V   R   Q   A   T   G   K   G   L   E   W   V   S   V   I   G   P   A
109 GTC CGC CAA GCA ACA GGA AAA GGT CTG GAG TGG GTC TCA GTT ATT GGT CCT GCT
                CDR2
    ~~~~~~~~~~~~~~~~~~~~~~~~~~~~~~~~~~~~~~~~~~~~
      G   D   T   Y   Y   P   G   S   V   K   G   R   F   T   I   S   R   E
163 GGT GAC ACA TAC TAT CCA GGC TCC GTG AAG GGC CGA TTC ACC ATC TCC AGA GAA

N   A   K   N   S   L   Y   L   Q   M   N   S   L   R   A   G   D   T
217 AAT GCC AAG AAC TCC TTG TAT CTT CAA ATG AAC AGC CTG AGA GCC GGG GAC ACG
                                                        CDR3
                                                    ~~~~~~~~~~~~~~~~~~~~~~~~~~~~~~~~~~~
      A   V   Y   Y   C   A   R   E   G   M   A   A   H   N   Y   Y   G   M
271 GCT GTG TAT TAC TGT GCA AGA GAG GGG ATG GCT GCC CAC AAC TAC TAC GGT ATG
        CDR3
    ~~~~~~~~
      D   V   W   G   Q   G   T   T   V   T   V   S   S
325 GAC GTC TGG GGC CAA GGG ACC ACG GTC ACC GTC TCC TCA
```

FIGURE 1B

Anti- BTLA 8D5 VK

V segment:      L6
    J segment:      JK5

```
        E   I   V   L   T   Q   S   P   A   T   L   S   L   S   P   G   E   R
    1  GAA ATT GTC TTG ACA CAG TCT CCA GCC ACC CTG TCT TTG TCT CCA GGG GAA AGA
                                           CDR1
                          ~~~~~~~~~~~~~~~~~~~~~~~~~~~~~~~~~~~~~~~~~~~~
        A   T   L   S   C   R   A   S   Q   S   V   S   S   Y   L   A   W   Y
   55  GCC ACC CTC TCC TGC AGG GCC AGT CAG AGT GTT AGC AGC TAC TTA GCC TGG TAC
                                                                       CDR2
                                                                   ~~~~~~~~~~~~~~~~~~~~
        Q   Q   K   P   G   Q   A   P   R   L   L   I   Y   D   A   S   N   R
  109  CAA CAG AAA CCT GGC CAG GCT CCC AGG CTC CTC ATC TAT GAT GCA TCC AAC AGG

CDR2
        ~~~~~~~~
        A   T   G   I   P   A   R   F   S   G   S   G   S   G   T   D   F   T
  163  GCC ACT GGC ATC CCA GCC AGG TTC AGT GGC AGT GGG TCT GGG ACA GAC TTC ACT
                                                                       CDR3
                                                                   ~~~~~~~~
        L   T   I   S   S   L   E   P   E   D   F   A   V   Y   Y   C   Q   Q
  217  CTC ACC ATC AGC AGC CTA GAG CCT GAA GAT TTT GCA GTT TAT TAC TGT CAG CAG

CDR3
        ~~~~~~~~~~~~~~~~~~~~~~~~~~~~~~~~
        R   S   N   W   P   P   I   T   F   G   Q   G   T   R   L   E   I   K
  271  CGT AGC AAC TGG CCC CCG ATC ACC TTC GGC CAA GGG ACA CGA CTG GAG ATT AAA
```

FIGURE 1C

Sequence features of the heavy and light chain variable regions of Hu 8D5 BTLA mAb.

| | |
|---|---|
| N-X-S/T (N-glycosylation potential) | No |
| N-G sequence (deamidation potential) | No |
| D-P sequence (hydrolysis potential) | No |
| D-G sequence (isomerization potential) | No |
| M in CDRs (oxidation potential) | VH CDR1 (germline)<br>2 in VH CDR3 |
| Unpaired C residue | No |

FIGURE 2A
Anti-BTLA antagonist 4C7 VH Sequences

```
V segment:      4-59
D segment:      ND
J segment:      JH6b

Q   V   Q   L   Q   E   S   G   P   G   L   V   K   P   S   E   T   L
  1 CAG GTG CAG CTG CAG GAG TCG GGC CCA GGA CTG GTG AAG CCT TCG GAG ACC CTA

CDR1
                                                            ~~~~~~~~~~~~~~~~~~
      S   L   T   C   T   V   H   G   G   S   I   N   H   Y   Y   W   S   W
 55 TCC CTC ACC TGC ACT GTC CAT GGT GGC TCC ATC AAT CAT TAC TAC TGG AGC TGG

CDR2
                                                            ~~~~~~~~~~~~~~~~~~
      I   R   Q   P   P   G   K   G   L   E   W   I   G   Y   I   Y   Y   S
109 ATC CGG CAG CCC CCA GGG AAG GGA CTG GAA TGG ATT GGA TAT ATC TAT TAC AGT

CDR2
    ~~~~~~~~~~~~~~~~~~~~~~~~~~~~~~~~~~~~~~~~~~~~~~
      G   S   T   K   Y   N   P   S   L   K   S   R   V   S   I   S   V   D
163 GGG AGC ACC AAG TAC AAT CCC TCC CTC AAG AGT CGC GTC AGC ATA TCA GTA GAC

T   S   K   N   Q   F   S   L   K   L   T   S   V   T   A   D   T
217 ACG TCC AAG AAC CAG TTC TCC CTG AAG CTG ACC TCT GTG ACC GCT GCG GAC ACG

CDR3
                              ~~~~~~~~~~~~~~~~~~~~~~~~~~~~~~~~~~~~~~~~~~~~~~
      A   V   Y   Y   C   A   R   E   W   P   Y   Y   Y   Y   E   M   D   V
271 GCC GTG TAT TAT TGT GCG AGA GAG TGG CCC TAC TAT TAC TAC GAA ATG GAC GTC

W   G   Q   G   T   T   V   T   V   S   S
325 TGG GGC CAA GGG ACC ACG GTC ACC GTC TCC TCA
```

FIGURE 2B
Anti-BTLA 4C7 VK

```
V segment:      A27
J segment:      JK1

E   I   V   L   T   Q   S   P   G   T   L   S   L   S   P   G   E   R
  1  GAA ATT GTG TTG ACG CAG TCT CCA GGC ACC CTG TCT TTG TCT CCA GGG GAA AGA

CDR1
                        ~~~~~~~~~~~~~~~~~~~~~~~~~~~~~~~~~~~~~~~~~~~~~~~~~~
      A   T   L   S   C   R   A   S   Q   S   V   S   S   S   Y   L   A   W
 55  GCC ACC CTC TCC TGC AGG GCC AGT CAG AGT GTT AGC AGC AGC TAC TTA GCC TGG

CDR2
                                                                ~~~~~~~~~~~~~~~~
      Y   Q   Q   K   P   G   Q   A   P   R   L   L   I   Y   G   A   S   S
109  TAC CAG CAG AAA CCT GGC CAG GCT CCC AGG CTC CTC ATC TAT GGT GCA TCC AGC

CDR2
      ~~~~~~~~~~~
      R   A   T   G   I   P   D   R   F   S   G   S   G   S   G   T   D   F
163  AGG GCC ACT GGC ATC CCA GAC AGG TTC AGT GGC AGT GGG TCT GGG ACA GAC TTC

CDR3
                                                                         ~~~
      T   L   T   I   S   R   L   E   P   E   D   F   A   V   Y   Y   C   Q
217  ACT CTC ACC ATC AGC AGA CTG GAG CCT GAA GAT TTT GCA GTC TAT TAC TGT CAG

CDR3
      ~~~~~~~~~~~~~~~~~~~~~~~~~~~~~~
      Q   Y   G   S   S   F   R   T   F   G   Q   G   T   K   V   E   I   K
271  CAG TAT GGT AGT TCA TTT CGG ACG TTC GGC CAA GGG ACC AAG GTG AAA ATC AAA
```

FIGURE 2C

Sequence features of the heavy and light chain variable regions of Hu 4C7 BTLA mAb.

| | |
|---|---|
| N-X-S/T (N-glycosylation potential) | No |
| N-G sequence (deamidation potential) | No |
| D-P sequence (hydrolysis potential) | No |
| D-G sequence (isomerization potential) | No |
| M in CDRs (oxidation potential) | One in VH CDR3 (germline encoded) |
| Unpaired C residue | No |
| Comments | VK no framework changes |

4C7 binds human BTLA expressed on CHO cells

4C7 binds cynomologus BTLA expressed on CHO cells

Human B Cell function is Inhibited by hu Mab8D5

FIGURE 12A-B
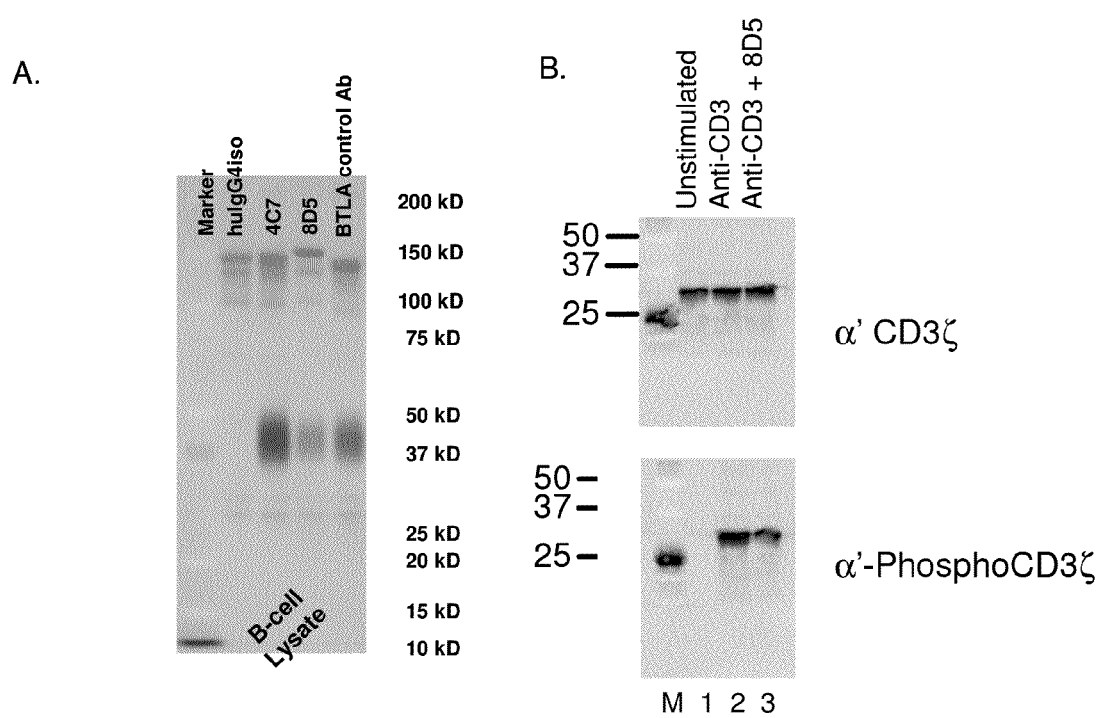

SEQUENCE LISTING

<160> NUMBER OF SEQ ID NOS: 67

<210> SEQ ID NO 1
<211> LENGTH: 870
<212> TYPE: DNA
<213> ORGANISM: Homo sapiens

<400> SEQUENCE: 1

```
atgaagacat tgcctgccat gcttggaact gggaaattat tttgggtctt cttcttaatc    60
ccatatctgg acatctggaa catccatggg aaagaatcat gtgatgtaca gctttatata   120
aagagacaat ctgaacactc catcttagca ggagatccct tgaactaga atgccctgtg    180
aaatactgtg ctaacaggcc tcatgtgact tggtgcaagc tcaatggaac aacatgtgta   240
aaacttgaag atagacaaac aagttggaag gaagagaaga catttcatt tttcattcta   300
cattttgaac caatgcttcc taatgacaat gggtcatacc gctgttctgc aaattttcag   360
tctaatctca ttgaaagcca ctcaacaact ctttatgtga cagatgtaaa aggtgcctca   420
gaacgaccct ccaaggacga agtggcaagc agaccctggc tcctgtatag tttacttcct   480
ttgggggggat tgcctctact catcactacc tggttctgcc tgttctgctg cctgagaagg   540
caccaaggaa agcaaaatga actctctgac acagcaggaa gggaaattaa tctggttgat   600
gctcacctta gagcgagca acagaagca agcaccaggc aaaattccca gtactgcta    660
tcagaagctg gaatttatga taatgaccct gacctttgtt tcaggatgca ggaagggtct   720
gaagtttgtt ctaatccatg cctggaagaa acaaaccag gcattgttta tgcttccctg   780
aaccattctg tcattggact gaactcaaga ctggcaagaa atgtaaaaga agcaccaaca   840
gaatatgcat ccatatgtgt gaggagttaa                                    870
```

<210> SEQ ID NO 2
<211> LENGTH: 289
<212> TYPE: PRT
<213> ORGANISM: Homo sapiens

<400> SEQUENCE: 2

```
Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
            20                  25                  30

Ser Cys Asp Val Gln Leu Tyr Ile Lys Arg Gln Ser Glu His Ser Ile
        35                  40                  45

Leu Ala Gly Asp Pro Phe Glu Leu Glu Cys Pro Val Lys Tyr Cys Ala
    50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Glu Lys Asn Ile Ser
                85                  90                  95

Phe Phe Ile Leu His Phe Glu Pro Met Leu Pro Asn Asp Asn Gly Ser
            100                 105                 110

Tyr Arg Cys Ser Ala Asn Phe Gln Ser Asn Leu Ile Glu Ser His Ser
        115                 120                 125

Thr Thr Leu Tyr Val Thr Asp Val Lys Gly Ala Ser Glu Arg Pro Ser
    130                 135                 140

Lys Asp Glu Val Ala Ser Arg Pro Trp Leu Leu Tyr Ser Leu Leu Pro
145                 150                 155                 160

Leu Gly Gly Leu Pro Leu Leu Ile Thr Thr Trp Phe Cys Leu Phe Cys
```

```
              165                 170                 175
Cys Leu Arg Arg His Gln Gly Lys Gln Asn Glu Leu Ser Asp Thr Ala
            180                 185                 190

Gly Arg Glu Ile Asn Leu Val Asp Ala His Leu Lys Ser Glu Gln Thr
        195                 200                 205

Glu Ala Ser Thr Arg Gln Asn Ser Gln Val Leu Leu Ser Glu Ala Gly
    210                 215                 220

Ile Tyr Asp Asn Asp Pro Asp Leu Cys Phe Arg Met Gln Glu Gly Ser
225                 230                 235                 240

Glu Val Cys Ser Asn Pro Cys Leu Glu Glu Asn Lys Pro Gly Ile Val
                245                 250                 255

Tyr Ala Ser Leu Asn His Ser Val Ile Gly Leu Asn Ser Arg Leu Ala
            260                 265                 270

Arg Asn Val Lys Glu Ala Pro Thr Glu Tyr Ala Ser Ile Cys Val Arg
        275                 280                 285

Ser

<210> SEQ ID NO 3
<211> LENGTH: 921
<212> TYPE: DNA
<213> ORGANISM: Mus musculus

<400> SEQUENCE: 3
atgaagacag tgcctgccat gcttgggact cctcggttat ttagggaatt cttcatcctc      60
catctgggcc tctggagcat cctttgtgag aaagctacta agaggaatga tgaagagtgt     120
gaagtgcaac ttaatattaa gaggaattcc aaacactctg cctggacagg agagttattt     180
aaaattgaat gtcctgtgaa atactgtgtt catagaccta atgtgacttg gtgtaagcac     240 aatgaacaa tctgggtacc ccttgaagtt ggtcctcagc tatacactag ttgggaagaa     300
aatcgatcag ttccggtttt tgttctccat tttaaaccaa tacatctcag tgataacggg     360
tcgtatagct gttctacaaa cttcaattct caagttatta tagccattc agtaaccatc     420 catgtgagag aaaggactca aaactcttca gaacacccac taataacagt atctgacatc     480
ccagatgcca ccaatgcctc aggaccatcc accatggaag agaggccagg caggacttgg     540
ctgctttaca ccttgcttcc tttgggggca ttgcttctgc tccttgcctg tgtctgcctg     600
ctctgctttc tgaaaaggat ccaagggaaa gaaagaagc cttctgactt ggcaggaagg     660
gacactaacc tggttgatat tccagccagt tccaggacaa tcaccaagc actgccatca     720 ggaactggaa tttatgataa tgatccctgg tctagcatgc aggatgaatc tgaattgaca     780
attagcttgc aatcagagag aaacaaccag ggcattgttt atgcttcttt gaaccattgt     840
gttattggaa ggaatccaag acaggaaaac aacatgcagg aggcacccac agaatatgca     900
tccatttgtg tgagaagtta a                                                921

<210> SEQ ID NO 4
<211> LENGTH: 306
<212> TYPE: PRT
<213> ORGANISM: Mus musculus

<400> SEQUENCE: 4

Met Lys Thr Val Pro Ala Met Leu Gly Thr Pro Arg Leu Phe Arg Glu
1               5                   10                  15

Phe Phe Ile Leu His Leu Gly Leu Trp Ser Ile Leu Cys Glu Lys Ala
            20                  25                  30
```

```
Thr Lys Arg Asn Asp Glu Glu Cys Glu Val Gln Leu Asn Ile Lys Arg
         35                  40                  45
Asn Ser Lys His Ser Ala Trp Thr Gly Glu Leu Phe Lys Ile Glu Cys
 50                  55                  60
Pro Val Lys Tyr Cys Val His Arg Pro Asn Val Thr Trp Cys Lys His
 65                  70                  75                  80
Asn Gly Thr Ile Trp Val Pro Leu Glu Val Gly Pro Gln Leu Tyr Thr
                 85                  90                  95
Ser Trp Glu Glu Asn Arg Ser Val Pro Val Phe Val Leu His Phe Lys
             100                 105                 110
Pro Ile His Leu Ser Asp Asn Gly Ser Tyr Ser Cys Ser Thr Asn Phe
         115                 120                 125
Asn Ser Gln Val Ile Asn Ser His Ser Val Thr Ile His Val Arg Glu
 130                 135                 140
Arg Thr Gln Asn Ser Ser Glu His Pro Leu Ile Thr Val Ser Asp Ile
 145                 150                 155                 160
Pro Asp Ala Thr Asn Ala Ser Gly Pro Ser Thr Met Glu Glu Arg Pro
                 165                 170                 175
Gly Arg Thr Trp Leu Leu Tyr Thr Leu Leu Pro Leu Gly Ala Leu Leu
             180                 185                 190
Leu Leu Leu Ala Cys Val Cys Leu Leu Cys Phe Leu Lys Arg Ile Gln
         195                 200                 205
Gly Lys Glu Lys Lys Pro Ser Asp Leu Ala Gly Arg Asp Thr Asn Leu
 210                 215                 220
Val Asp Ile Pro Ala Ser Ser Arg Thr Asn His Gln Ala Leu Pro Ser
225                 230                 235                 240
Gly Thr Gly Ile Tyr Asp Asn Asp Pro Trp Ser Ser Met Gln Asp Glu
                 245                 250                 255
Ser Glu Leu Thr Ile Ser Leu Gln Ser Glu Arg Asn Asn Gln Gly Ile
             260                 265                 270
Val Tyr Ala Ser Leu Asn His Cys Val Ile Gly Arg Asn Pro Arg Gln
         275                 280                 285
Glu Asn Asn Met Gln Glu Ala Pro Thr Glu Tyr Ala Ser Ile Cys Val
 290                 295                 300
Arg Ser
305

<210> SEQ ID NO 5
<211> LENGTH: 5
<212> TYPE: PRT
<213> ORGANISM: Homo sapiens

<400> SEQUENCE: 5

Ser Tyr Asp Met His
1               5

<210> SEQ ID NO 6
<211> LENGTH: 16
<212> TYPE: PRT
<213> ORGANISM: Homo sapiens

<400> SEQUENCE: 6

Val Ile Gly Pro Ala Gly Asp Thr Tyr Tyr Pro Gly Ser Val Lys Gly
1               5                   10                  15

<210> SEQ ID NO 7
<211> LENGTH: 13
```

<212> TYPE: PRT
<213> ORGANISM: Homo sapiens

<400> SEQUENCE: 7

Glu Gly Met Ala Ala His Asn Tyr Tyr Gly Met Asp Val
1               5                   10

<210> SEQ ID NO 8
<211> LENGTH: 420
<212> TYPE: DNA
<213> ORGANISM: Homo sapiens

<400> SEQUENCE: 8

```
atggagttgg ggctgagctg ggttttcctt gttgctatat tagaaggtgt ccagtgtgag     60
gtgcagctgg tggagtctgg gggaggcttg gtacagccgg gggggtccct gagactctcc    120
tgtgcagcct ctggattcac catcagtagt tacgacatgc actgggtccg ccaagcaaca    180
ggaaaaggtc tggagtgggt ctcagttatt ggtcctgctg gtgacacata ctatccaggc    240
tccgtgaagg gccgattcac catctccaga gaaaatgcca agaactcctt gtatcttcaa    300
atgaacagcc tgagagccgg ggacacggct gtgtattact gtgcaagaga ggggatggct    360
gcccacaact actacggtat ggacgtctgg ggccaaggga ccacggtcac cgtctcctca    420
```

<210> SEQ ID NO 9
<211> LENGTH: 140
<212> TYPE: PRT
<213> ORGANISM: Homo sapiens

<400> SEQUENCE: 9

Met Glu Leu Gly Leu Ser Trp Val Phe Leu Val Ala Ile Leu Glu Gly
1               5                   10                  15

Val Gln Cys Glu Val Gln Leu Val Glu Ser Gly Gly Gly Leu Val Gln
                20                  25                  30

Pro Gly Gly Ser Leu Arg Leu Ser Cys Ala Ala Ser Gly Phe Thr Ile
        35                  40                  45

Ser Ser Tyr Asp Met His Trp Val Arg Gln Ala Thr Gly Lys Gly Leu
    50                  55                  60

Glu Trp Val Ser Val Ile Gly Pro Ala Gly Asp Thr Tyr Tyr Pro Gly
65                  70                  75                  80

Ser Val Lys Gly Arg Phe Thr Ile Ser Arg Glu Asn Ala Lys Asn Ser
                85                  90                  95

Leu Tyr Leu Gln Met Asn Ser Leu Arg Ala Gly Asp Thr Ala Val Tyr
            100                 105                 110

Tyr Cys Ala Arg Glu Gly Met Ala Ala His Asn Tyr Tyr Gly Met Asp
        115                 120                 125

Val Trp Gly Gln Gly Thr Thr Val Thr Val Ser Ser
    130                 135                 140

<210> SEQ ID NO 10
<211> LENGTH: 363
<212> TYPE: DNA
<213> ORGANISM: Homo sapiens
<220> FEATURE:
<221> NAME/KEY: CDS
<222> LOCATION: (1)..(363)

<400> SEQUENCE: 10 gag gtg cag ctg gtg gag tct ggg gga ggc ttg gta cag ccg ggg ggg     48
Glu Val Gln Leu Val Glu Ser Gly Gly Gly Leu Val Gln Pro Gly Gly
1               5                   10                  15

```
tcc ctg aga ctc tcc tgt gca gcc tct gga ttc acc atc agt agt tac    96
Ser Leu Arg Leu Ser Cys Ala Ala Ser Gly Phe Thr Ile Ser Ser Tyr
        20                  25                  30 gac atg cac tgg gtc cgc caa gca aca gga aaa ggt ctg gag tgg gtc   144
Asp Met His Trp Val Arg Gln Ala Thr Gly Lys Gly Leu Glu Trp Val
            35                  40                  45 tca gtt att ggt cct gct ggt gac aca tac tat cca ggc tcc gtg aag   192
Ser Val Ile Gly Pro Ala Gly Asp Thr Tyr Tyr Pro Gly Ser Val Lys
    50                  55                  60 ggc cga ttc acc atc tcc aga gaa aat gcc aag aac tcc ttg tat ctt   240
Gly Arg Phe Thr Ile Ser Arg Glu Asn Ala Lys Asn Ser Leu Tyr Leu
65                  70                  75                  80 caa atg aac agc ctg aga gcc ggg gac acg gct gtg tat tac tgt gca   288
Gln Met Asn Ser Leu Arg Ala Gly Asp Thr Ala Val Tyr Tyr Cys Ala
                85                  90                  95 aga gag ggg atg gct gcc cac aac tac tac ggt atg gac gtc tgg ggc   336
Arg Glu Gly Met Ala Ala His Asn Tyr Tyr Gly Met Asp Val Trp Gly
            100                 105                 110 caa ggg acc acg gtc acc gtc tcc tca                               363
Gln Gly Thr Thr Val Thr Val Ser Ser
    115                 120
```

<210> SEQ ID NO 11
<211> LENGTH: 121
<212> TYPE: PRT
<213> ORGANISM: Homo sapiens

<400> SEQUENCE: 11

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser Tyr
            20                  25                  30

Asp Met His Trp Val Arg Gln Ala Thr Gly Lys Gly Leu Glu Trp Val
        35                  40                  45

Ser Val Ile Gly Pro Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Glu Gly Met Ala Ala His Asn Tyr Tyr Gly Met Asp Val Trp Gly
            100                 105                 110

Gln Gly Thr Thr Val Thr Val Ser Ser
        115                 120
```

<210> SEQ ID NO 12
<211> LENGTH: 11
<212> TYPE: PRT
<213> ORGANISM: Homo sapiens

<400> SEQUENCE: 12

```
Arg Ala Ser Gln Ser Val Ser Ser Tyr Leu Ala
1               5                   10
```

<210> SEQ ID NO 13
<211> LENGTH: 7
<212> TYPE: PRT
<213> ORGANISM: Homo sapiens

<400> SEQUENCE: 13

```
Asp Ala Ser Asn Arg Ala Thr
1               5
```

<210> SEQ ID NO 14
<211> LENGTH: 10
<212> TYPE: PRT
<213> ORGANISM: Homo sapiens

<400> SEQUENCE: 14

```
Gln Gln Arg Ser Asn Trp Pro Pro Ile Thr
1               5                   10
```

<210> SEQ ID NO 15
<211> LENGTH: 384
<212> TYPE: DNA
<213> ORGANISM: Homo sapiens

<400> SEQUENCE: 15

```
atggaagccc agctcagct tctcttcctc ctgctactct ggctcccaga taccaccgga      60
gaaattgtgt tgacacagtc tccagccacc ctgtctttgt ctccagggga aagagccacc    120
ctctcctgca gggccagtca gagtgttagc agctacttag cctggtacca acagaaacct    180
ggccaggctc ccaggctcct catctatgat gcatccaaca gggccactgg catcccagcc    240
aggttcagtg gcagtgggtc tgggacagac ttcactctca ccatcagcag cctagagcct    300
gaagattttg cagtttatta ctgtcagcag cgtagcaact ggccccccgat caccttcggc    360
caagggacac gactggagat taaa                                           384
```

<210> SEQ ID NO 16
<211> LENGTH: 128
<212> TYPE: PRT
<213> ORGANISM: Homo sapiens

<400> SEQUENCE: 16

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Pro Pro Ile Thr Phe Gly Gln Gly Thr Arg Leu Glu Ile Lys
        115                 120                 125
```

<210> SEQ ID NO 17
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 17

```
gaa att gtg ttg aca cag tct cca gcc acc ctg tct ttg tct cca ggg       48
Glu Ile Val Leu Thr Gln Ser Pro Ala Thr Leu Ser Leu Ser Pro Gly
1               5                   10                  15 gaa aga gcc acc ctc tcc tgc agg gcc agt cag agt gtt agc agc tac       96
Glu Arg Ala Thr Leu Ser Cys Arg Ala Ser Gln Ser Val Ser Ser Tyr
                20                  25                  30 tta gcc tgg tac caa cag aaa cct ggc cag gct ccc agg ctc ctc atc      144
Leu Ala Trp Tyr Gln Gln Lys Pro Gly Gln Ala Pro Arg Leu Leu Ile
            35                  40                  45 tat gat gca tcc aac agg gcc act ggc atc cca gcc agg ttc agt ggc      192
Tyr Asp Ala Ser Asn Arg Ala Thr Gly Ile Pro Ala Arg Phe Ser Gly
    50                  55                  60 agt ggg tct ggg aca gac ttc act ctc acc atc agc agc cta gag cct      240
Ser Gly Ser Gly Thr Asp Phe Thr Leu Thr Ile Ser Ser Leu Glu Pro
65                  70                  75                  80 gaa gat ttt gca gtt tat tac tgt cag cag cgt agc aac tgg ccc ccg      288
Glu Asp Phe Ala Val Tyr Tyr Cys Gln Gln Arg Ser Asn Trp Pro Pro
                85                  90                  95 atc acc ttc ggc caa ggg aca cga ctg gag att aaa                      324
Ile Thr Phe Gly Gln Gly Thr Arg Leu Glu Ile Lys
                100                 105
```

<210> SEQ ID NO 18
<211> LENGTH: 108
<212> TYPE: PRT
<213> ORGANISM: Homo sapiens

<400> SEQUENCE: 18

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ile Thr Phe Gly Gln Gly Thr Arg Leu Glu Ile Lys
                100                 105
```

<210> SEQ ID NO 19
<211> LENGTH: 5
<212> TYPE: PRT
<213> ORGANISM: Homo sapiens

<400> SEQUENCE: 19

```
His Tyr Tyr Trp Ser
1               5
```

<210> SEQ ID NO 20
<211> LENGTH: 16
<212> TYPE: PRT
<213> ORGANISM: Homo sapiens

<400> SEQUENCE: 20

```
Tyr Ile Tyr Tyr Ser Gly Ser Thr Lys Tyr Asn Pro Ser Leu Lys Ser
1               5                   10                  15
```

<210> SEQ ID NO 21
<211> LENGTH: 11
<212> TYPE: PRT
<213> ORGANISM: Homo sapiens

<400> SEQUENCE: 21

Glu Trp Pro Tyr Tyr Tyr Tyr Glu Met Asp Val
1               5                   10

<210> SEQ ID NO 22
<211> LENGTH: 414
<212> TYPE: DNA
<213> ORGANISM: Homo sapiens

<400> SEQUENCE: 22
atgaaacatc tgtggttctt ccttctcctg gtggcagctc ccagatgggt cctgtcccag      60
gtgcagctgc aggagtcggg cccaggactg gtgaagcctt cggagaccct atccctcacc     120
tgcactgtcc atggtggctc catcaatcat tactactgga gctggatccg gcagccccca     180
gggaagggac tggaatggat tggatatatc tattacagtg ggagcaccaa gtacaatccc     240
tccctcaaga gtcgcgtcag catatcagta gacacgtcca agaaccagtt ctccctgaag     300
ctgacctctg tgaccgctgc ggacacggcc gtgtattatt gtgcgagaga gtggccctac     360
tattactacg aaatggacgt ctggggccaa gggaccacgg tcaccgtctc ctca           414

<210> SEQ ID NO 23
<211> LENGTH: 138
<212> TYPE: PRT
<213> ORGANISM: Homo sapiens

<400> SEQUENCE: 23

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val His Gly Gly Ser Ile
        35                  40                  45

Asn His Tyr Tyr Trp Ser Trp Ile Arg Gln Pro Pro Gly Lys Gly Leu
    50                  55                  60

Glu Trp Ile Gly Tyr Ile Tyr Tyr Ser Gly Ser Thr Lys Tyr Asn Pro
65                  70                  75                  80

Ser Leu Lys Ser Arg Val Ser Ile Ser Val Asp Thr Ser Lys Asn Gln
                85                  90                  95

Phe Ser Leu Lys Leu Thr Ser Val Thr Ala Ala Asp Thr Ala Val Tyr
            100                 105                 110

Tyr Cys Ala Arg Glu Trp Pro Tyr Tyr Tyr Glu Met Asp Val Trp
        115                 120                 125

Gly Gln Gly Thr Thr Val Thr Val Ser Ser
    130                 135

<210> SEQ ID NO 24
<211> LENGTH: 357
<212> TYPE: DNA
<213> ORGANISM: Homo sapiens
<220> FEATURE:
<221> NAME/KEY: CDS
<222> LOCATION: (1)..(357)

<400> SEQUENCE: 24

```
cag gtg cag ctg cag gag tcg ggc cca gga ctg gtg aag cct tcg gag      48
Gln Val Gln Leu Gln Glu Ser Gly Pro Gly Leu Val Lys Pro Ser Glu
1               5                   10                  15 acc cta tcc ctc acc tgc act gtc cat ggt ggc tcc atc aat cat tac      96
Thr Leu Ser Leu Thr Cys Thr Val His Gly Gly Ser Ile Asn His Tyr
            20                  25                  30 tac tgg agc tgg atc cgg cag ccc cca ggg aag gga ctg gaa tgg att     144
Tyr Trp Ser Trp Ile Arg Gln Pro Pro Gly Lys Gly Leu Glu Trp Ile
        35                  40                  45 gga tat atc tat tac agt ggg agc acc aag tac aat ccc tcc ctc aag     192
Gly Tyr Ile Tyr Tyr Ser Gly Ser Thr Lys Tyr Asn Pro Ser Leu Lys
    50                  55                  60 agt cgc gtc agc ata tca gta gac acg tcc aag aac cag ttc tcc ctg     240
Ser Arg Val Ser Ile Ser Val Asp Thr Ser Lys Asn Gln Phe Ser Leu
65                  70                  75                  80 aag ctg acc tct gtg acc gct gcg gac acg gcc gtg tat tat tgt gcg     288
Lys Leu Thr Ser Val Thr Ala Ala Asp Thr Ala Val Tyr Tyr Cys Ala
                85                  90                  95 aga gag tgg ccc tac tat tac tac gaa atg gac gtc tgg ggc caa ggg     336
Arg Glu Trp Pro Tyr Tyr Tyr Tyr Glu Met Asp Val Trp Gly Gln Gly
            100                 105                 110 acc acg gtc acc gtc tcc tca                                          357
Thr Thr Val Thr Val Ser Ser
        115
```

<210> SEQ ID NO 25
<211> LENGTH: 119
<212> TYPE: PRT
<213> ORGANISM: Homo sapiens

<400> SEQUENCE: 25

Gln Val Gln Leu Gln Glu Ser Gly Pro Gly Leu Val Lys Pro Ser Glu
1               5                   10                  15

Thr Leu Ser Leu Thr Cys Thr Val His Gly Gly Ser Ile Asn His Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Lys Tyr Asn Pro Ser Leu Lys
    50                  55                  60

Ser Arg Val Ser Ile Ser Val Asp Thr Ser Lys Asn Gln Phe Ser Leu
65                  70                  75                  80

Lys Leu Thr Ser Val Thr Ala Ala Asp Thr Ala Val Tyr Tyr Cys Ala
                85                  90                  95

Arg Glu Trp Pro Tyr Tyr Tyr Tyr Glu Met Asp Val Trp Gly Gln Gly
            100                 105                 110

Thr Thr Val Thr Val Ser Ser
        115

<210> SEQ ID NO 26
<211> LENGTH: 12
<212> TYPE: PRT
<213> ORGANISM: Homo sapiens

<400> SEQUENCE: 26

Arg Ala Ser Gln Ser Val Ser Ser Ser Tyr Leu Ala
1               5                   10

<210> SEQ ID NO 27
<211> LENGTH: 7

<212> TYPE: PRT
<213> ORGANISM: Homo sapiens

<400> SEQUENCE: 27

Gly Ala Ser Ser Arg Ala Thr
1               5

<210> SEQ ID NO 28
<211> LENGTH: 9
<212> TYPE: PRT
<213> ORGANISM: Homo sapiens

<400> SEQUENCE: 28

Gln Gln Tyr Gly Ser Ser Phe Arg Thr
1               5

<210> SEQ ID NO 29
<211> LENGTH: 384
<212> TYPE: DNA
<213> ORGANISM: Homo sapiens

<400> SEQUENCE: 29

```
atggaaaccc cagcgcagct tctcttcctc ctgctactct ggctcccaga taccaccgga      60
gaaattgtgt tgacgcagtc tccaggcacc ctgtctttgt ctccagggga agagccacc     120
ctctcctgca gggccagtca gagtgttagc agcagctact tagcctggta ccagcagaaa    180
cctggccagg ctcccaggct cctcatctat ggtgcatcca gcagggccac tggcatccca    240
gacaggttca gtggcagtgg gtctgggaca gacttcactc tcaccatcag cagactggag    300
cctgaagatt ttgcagtgta ttactgtcag cagtatggta gttcatttcg gacgttcggc    360
caagggacca aggtggaaat caaa                                           384
```

<210> SEQ ID NO 30
<211> LENGTH: 128
<212> TYPE: PRT
<213> ORGANISM: Homo sapiens

<400> SEQUENCE: 30

Met Glu Thr Pro Ala Gln Leu Leu Phe Leu Leu Leu Leu Trp Leu Pro
1               5                  10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Ser Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Ser Ser Phe Arg Thr Phe Gly Gln Gly Thr Lys Val Glu Ile Lys
        115                 120                 125

<210> SEQ ID NO 31
<211> LENGTH: 324
<212> TYPE: DNA
<213> ORGANISM: Homo sapiens
<220> FEATURE:

<221> NAME/KEY: CDS
<222> LOCATION: (1)..(324)

<400> SEQUENCE: 31

```
gaa att gtg ttg acg cag tct cca ggc acc ctg tct ttg tct cca ggg     48
Glu Ile Val Leu Thr Gln Ser Pro Gly Thr Leu Ser Leu Ser Pro Gly
1               5                   10                  15 gaa aga gcc acc ctc tcc tgc agg gcc agt cag agt gtt agc agc agc     96
Glu Arg Ala Thr Leu Ser Cys Arg Ala Ser Gln Ser Val Ser Ser Ser
                20                  25                  30 tac tta gcc tgg tac cag cag aaa cct ggc cag gct ccc agg ctc ctc    144
Tyr Leu Ala Trp Tyr Gln Gln Lys Pro Gly Gln Ala Pro Arg Leu Leu
            35                  40                  45 atc tat ggt gca tcc agc agg gcc act ggc atc cca gac agg ttc agt    192
Ile Tyr Gly Ala Ser Ser Arg Ala Thr Gly Ile Pro Asp Arg Phe Ser
        50                  55                  60 ggc agt ggg tct ggg aca gac ttc act ctc acc atc agc aga ctg gag    240
Gly Ser Gly Ser Gly Thr Asp Phe Thr Leu Thr Ile Ser Arg Leu Glu
65                  70                  75                  80 cct gaa gat ttt gca gtg tat tac tgt cag cag tat ggt agt tca ttt    288
Pro Glu Asp Phe Ala Val Tyr Tyr Cys Gln Gln Tyr Gly Ser Ser Phe
                85                  90                  95 cgg acg ttc ggc caa ggg acc aag gtg gaa atc aaa                    324
Arg Thr Phe Gly Gln Gly Thr Lys Val Glu Ile Lys
                100                 105
```

<210> SEQ ID NO 32
<211> LENGTH: 108
<212> TYPE: PRT
<213> ORGANISM: Homo sapiens

<400> SEQUENCE: 32

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Phe
                85                  90                  95

Arg Thr Phe Gly Gln Gly Thr Lys Val Glu Ile Lys
                100                 105
```

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
gcctgagttc cacgacaccg tc     22

<210> SEQ ID NO 34
<211> LENGTH: 32
<212> TYPE: DNA

-continued

<213> ORGANISM: Artificial Sequence
<220> FEATURE:
<223> OTHER INFORMATION: Description of Artificial Sequence: Synthetic primer

<400> SEQUENCE: 34
gcaggcacac aacagaggca gttccagatt tc                        32

<210> SEQ ID NO 35
<211> LENGTH: 289
<212> TYPE: PRT
<213> ORGANISM: Homo sapiens

<400> SEQUENCE: 35

Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
            20                  25                  30

Ser Cys Asp Val Gln Leu Tyr Ile Lys Arg Gln Ser Glu His Ser Ile
        35                  40                  45

Leu Ala Gly Asp Pro Phe Glu Leu Glu Cys Pro Val Lys Tyr Cys Ala
    50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Glu Lys Asn Ile Ser
                85                  90                  95

Phe Phe Ile Leu His Phe Glu Pro Val Leu Pro Asn Asp Asn Gly Ser
            100                 105                 110

Tyr Arg Cys Ser Ala Asn Phe Gln Ser Asn Leu Ile Glu Ser His Ser
        115                 120                 125

Thr Thr Leu Tyr Val Thr Asp Val Lys Ser Ala Ser Glu Arg Pro Ser
    130                 135                 140

Lys Asp Glu Met Ala Ser Arg Pro Trp Leu Leu Tyr Ser Leu Leu Pro
145                 150                 155                 160

Leu Gly Gly Leu Pro Leu Leu Ile Thr Thr Cys Phe Cys Leu Phe Cys
                165                 170                 175

Cys Leu Arg Arg His Gln Gly Lys Gln Asn Glu Leu Ser Asp Thr Ala
            180                 185                 190

Gly Arg Glu Ile Asn Leu Val Asp Ala His Leu Lys Ser Glu Gln Thr
        195                 200                 205

Glu Ala Ser Thr Arg Gln Asn Ser Gln Val Leu Leu Ser Glu Thr Gly
    210                 215                 220

Ile Tyr Asp Asn Asp Pro Asp Leu Cys Phe Arg Met Gln Glu Gly Ser
225                 230                 235                 240

Glu Val Tyr Ser Asn Pro Cys Leu Glu Glu Asn Lys Pro Gly Ile Val
                245                 250                 255

Tyr Ala Ser Leu Asn His Ser Val Ile Gly Leu Asn Ser Arg Leu Ala
            260                 265                 270

Arg Asn Val Lys Glu Ala Pro Thr Glu Tyr Ala Ser Ile Cys Val Arg
        275                 280                 285

Ser

<210> SEQ ID NO 36
<211> LENGTH: 870
<212> TYPE: DNA
<213> ORGANISM: Homo sapiens

```
<400> SEQUENCE: 36
atgaagacat tgcctgccat gcttggaact gggaaattat tttgggtctt cttcttaatc    60
ccatatctgg acatctggaa catccatggg aagaatcat gtgatgtaca gctttatata   120
aagagacaat ctgaacactc catcttagca ggagatccct tgaactaga atgcccgtg    180 aaatactgtg ctaacaggcc tcatgtgact tggtgcaagc tcaatggaac aacatgtgta   240
aaacttgaag atagacaaac aagttggaag gaagagaaga acatttcatt tttcattcta   300
cattttgaac cagtgcttcc taatgacaat gggtcatacc gctgttctgc aaattttcag   360
tctaatctca ttgaaagcca ctcaacaact ctttatgtga cagatgtaaa aagtgcctca   420
gaacgaccct ccaaggacga aatggcaagc agaccctggc tcctgtatag tttacttcct   480 ttgggggggat tgcctctact catcactacc tgtttctgcc tgttctgctg cctgagaagg   540
caccaaggaa agcaaaatga actctctgac acagcaggaa gggaaattaa cctggttgat   600
gctcacctta agagtgagca aacagaagca agcaccaggc aaaattccca agtactgcta   660
tcagaaactg gaatttatga taatgaccct gacctttgtt tcaggatgca ggaagggtct   720
gaagtttatt ctaatccatg cctggaagaa aacaaaccag gcattgttta tgcttccctg   780
aaccattctg tcattggact gaactcaaga ctggcaagaa atgtaaaaga agcaccaaca   840
gaatatgcat ccatatgtgt gaggagttaa                                     870

<210> SEQ ID NO 37
<211> LENGTH: 289
<212> TYPE: PRT
<213> ORGANISM: Homo sapiens

<400> SEQUENCE: 37

Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
            20                  25                  30

Ser Cys Asp Val Gln Leu Tyr Ile Lys Arg Gln Ser Glu His Ser Ile
        35                  40                  45

Leu Ala Gly Asp Pro Phe Glu Leu Glu Cys Pro Val Lys Tyr Cys Ala
    50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Lys Asn Ile Ser
                85                  90                  95

Phe Phe Ile Leu His Phe Glu Pro Val Leu Pro Asn Asp Asn Gly Ser
            100                 105                 110

Tyr Arg Cys Ser Ala Asn Phe Gln Ser Asn Leu Ile Glu Ser His Ser
        115                 120                 125

Thr Thr Leu Tyr Val Thr Asp Val Lys Ser Ala Ser Glu Arg Pro Ser
    130                 135                 140

Lys Asp Glu Met Ala Ser Arg Pro Trp Leu Leu Tyr Ser Leu Leu Pro
145                 150                 155                 160

Leu Gly Gly Leu Pro Leu Leu Ile Thr Thr Cys Phe Cys Leu Phe Cys
                165                 170                 175

Cys Leu Arg Arg His Gln Gly Lys Gln Asn Glu Leu Ser Asp Thr Ala
            180                 185                 190

Gly Arg Glu Ile Asn Leu Val Asp Ala His Leu Lys Ser Glu Gln Thr
        195                 200                 205
```

```
Glu Ala Ser Thr Arg Gln Asn Ser Gln Val Leu Leu Ser Glu Thr Gly
            210                 215                 220

Ile Tyr Asp Asn Asp Pro Asp Leu Cys Phe Arg Met Gln Glu Gly Ser
225                 230                 235                 240

Glu Val Tyr Ser Asn Pro Cys Leu Glu Glu Asn Lys Pro Gly Ile Val
                245                 250                 255

Tyr Ala Ser Leu Asn His Ser Val Ile Gly Pro Asn Ser Arg Leu Ala
                260                 265                 270

Arg Asn Val Lys Glu Ala Pro Thr Glu Tyr Ala Ser Ile Cys Val Arg
            275                 280                 285

Ser

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Met, Lys, Leu, Ala or Phe

<400> SEQUENCE: 38

Ser Tyr Asp Xaa His
1               5

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Met, Lys, Leu, Ala or Phe
<220> FEATURE:
<221> NAME/KEY: MOD_RES
<222> LOCATION: (7)..(7)
<223> OTHER INFORMATION: Asn, Gln or Ala
<220> FEATURE:
<221> NAME/KEY: MOD_RES
<222> LOCATION: (11)..(11)
<223> OTHER INFORMATION: Met, Lys, Leu, Ala or Phe

<400> SEQUENCE: 39

Glu Gly Xaa Ala Ala His Xaa Tyr Tyr Gly Xaa Asp Val
1               5                   10

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Gln or Ala

<400> SEQUENCE: 40

Asp Ala Ser Xaa Arg Ala Thr
1               5
```

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Gln or Ala

<400> SEQUENCE: 41

Gln Gln Arg Ser Xaa Trp Pro Pro Ile Thr
1               5                   10

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(12)
<223> OTHER INFORMATION: This region may encompass "Asn Pro," "Gln Pro,"
      "Ala Pro" or "Asn Ala"

<400> SEQUENCE: 42

Tyr Ile Tyr Tyr Ser Gly Ser Thr Lys Tyr Xaa Xaa Ser Leu Lys Ser
1               5                   10                  15

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Met, Lys, Leu, Ala or Phe

<400> SEQUENCE: 43

Glu Trp Pro Tyr Tyr Tyr Tyr Glu Xaa Asp Val
1               5                   10

<210> SEQ ID NO 44
<211> LENGTH: 441
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
atggacatac tttgttccac gctcctgcta ctgactgtcc cgtcctgggt cttatcccag      60
gtcaccttga gggagtctgg tcctgcgctg gtgaaaccca cacagaccct cacactgacc     120
tgcaccttct ctgggttctc actcagcact agtggaatgg gtgtgagctg gatccgtcag     180
cccccaggga aggccctgga gtggcttgca gtcattgatt gggatggtac taaagactac     240
agcacatctc tgaagaccag gctcaccatc tccaaggaca cctccaaaaa ccaggtggtc     300
cttacaatga ccaacatgga ccctgtggac acagccacgt attactgtgc acggatccgt     360
attaatgtgg ttcggggagt tattatcaac tactatggta tggacgtctg gggccaaggg     420
accacggtca ccgtctcctc a    441

<210> SEQ ID NO 45
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Asp Ile Leu Cys Ser Thr Leu Leu Leu Thr Val Pro Ser Trp
1               5                   10                  15

Val Leu Ser Gln Val Thr Leu Arg Glu Ser Gly Pro Ala Leu Val Lys
            20                  25                  30

Pro Thr Gln Thr Leu Thr Leu Thr Cys Thr Phe Ser Gly Phe Ser Leu
        35                  40                  45

Ser Thr Ser Gly Met Gly Val Ser Trp Ile Arg Gln Pro Pro Gly Lys
    50                  55                  60

Ala Leu Glu Trp Leu Ala Val Ile Asp Trp Asp Gly Thr Lys Asp Tyr
65                  70                  75                  80

Ser Thr Ser Leu Lys Thr Arg Leu Thr Ile Ser Lys Asp Thr Ser Lys
                85                  90                  95

Asn Gln Val Val Leu Thr Met Thr Asn Met Asp Pro Val Asp Thr Ala
            100                 105                 110

Thr Tyr Tyr Cys Ala Arg Ile Arg Ile Asn Val Val Arg Gly Val Ile
        115                 120                 125

Ile Asn Tyr Tyr Gly Met Asp Val Trp Gly Gln Gly Thr Thr Val Thr
    130                 135                 140

Val Ser Ser
145

<210> SEQ ID NO 46
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
atggaaaccc cagcgcagct tctcttcctc ctgctactct ggctcccaga taccaccgga    60
gaaattgtgt tgacgcagtc tccaggcacc ctgtctttgt ctccagggga aagagccacc    120
ctctcctgca gggccagtca gagtgttagc agcagctact tagcctggta ccagcagaaa    180
cctggccagg ctcccaggct cctcatctat ggtgcatcca gcagggccac tggcatccca    240
gacaggttca gtggcagtgg gtctgggaca gacttcactc tcaccatcag cagactggag    300
cctgaagatt ttgcagtgta ttactgtcag cagtatggta ggtcacccgc gtacactttt    360
ggccagggga ccaagctgga gatcaaa    387

<210> SEQ ID NO 47
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Arg Ser Pro Ala Tyr Thr Phe Gly Gln Gly Thr Lys Leu Glu Ile
        115                 120                 125

Lys

<210> SEQ ID NO 48
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
atggaagccc cagctcagct tctcttcctc ctgctactct ggctcccaga taccaccgga      60
gaaattgtgt tgacacagtc tccagccacc ctgtctttgt ctccagggga aagagccacc     120
ctctcctgca gggccagtca gagtgttagc agctacttag cctggtacca acagaaacct     180
ggccaggctc ccaggctcct catctatgat gcatccaaca gggccactgg catcccagcc     240
aggttcagtg gcagtgggtc tgggacagac ttcactctca ccatcagcag cctagagcct     300
gaagattttg cagtttatta ctgtcagcag cgtagcaact ggccattcac tttcggccct     360
gggaccaaag tggatatcaa a                                               381

<210> SEQ ID NO 49
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Glu Ala Pro Ala Gln Leu Leu Phe Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser 85                  90                  95
Ser Leu Glu Pro Glu Asp Phe Ala Val Tyr Tyr Cys Gln Gln Arg Ser
                100                 105                 110

Asn Trp Pro Phe Thr Phe Gly Pro Gly Thr Lys Val Asp Ile Lys
        115                 120                 125

<210> SEQ ID NO 50
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
atggaaaccc cagcgcagct tctcttcctc ctgctactct ggctcccaga taccaccgga      60
gaaattgtgt tgacgcagtc tccaggcacc ctgtctttgt ctccagggga aagagccacc    120
ctctcctgca gggccagtca gagtgttagc agcagctact tagcctggta ccagcagaaa    180
cctggccagg ctcccaggct cctcatctat gatgcatcca acagggccac tggcatccca    240
gccaggttca gtggcagtgg gtctgggaca gacttcactc tcaccatcag cagcctagag    300
cctgaagatt ttgcagttta ttactgtcag cagcgtagca ctggccatt cactttcggc     360 cctgggacca aagtggatat caaa                                          384

<210> SEQ ID NO 51
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala
    50                  55                  60

Pro Arg Leu Leu Ile Tyr Asp Ala Ser Asn Arg Ala Thr Gly Ile Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Val Tyr Tyr Cys Gln Gln Arg
                100                 105                 110

Ser Asn Trp Pro Phe Thr Phe Gly Pro Gly Thr Lys Val Asp Ile Lys
            115                 120                 125

<210> SEQ ID NO 52
<211> LENGTH: 432
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

```
atggagtttg tgctgagctg ggttttcctt gttgctatat taaaaggtgt ccagtgtgag      60
gttcagctgg tgcagtctgg gggaggcttg gtacatcctg ggggtccct gagactctcc     120 tgtgcaggct ctggattcac cttcagtagc tatgctatgc actgggttcg ccaggctcca    180
ggaaaaggtc tggagtgggt ttcagttatt ggtactggtg ttgccacata ctatgcagac    240
tccgtgaagg gccgattcac catctccaga gacaatgcca agaactcctt gtttcttcat    300
atgaacagcc tgagagccga ggacatggct gtgtattact gtgcaagagg cttttactat    360
ggttcgggga ctaattatta caaccgcggt atggacgtct ggggccaagg gaccacggtc    420
accgtctcct ca                                                         432
```

<210> SEQ ID NO 53
<211> LENGTH: 144
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 53

```
Met Glu Phe Val Leu Ser Trp Val Phe Leu Val Ala Ile Leu Lys Gly
1               5                   10                  15

Val Gln Cys Glu Val Gln Leu Val Gln Ser Gly Gly Gly Leu Val His
                20                  25                  30

Pro Gly Gly Ser Leu Arg Leu Ser Cys Ala Gly Ser Gly Phe Thr Phe
            35                  40                  45

Ser Ser Tyr Ala Met His Trp Val Arg Gln Ala Pro Gly Lys Gly Leu
    50                  55                  60

Glu Trp Val Ser Val Ile Gly Thr Gly Val Ala Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Phe Leu His Met Asn Ser Leu Arg Ala Glu Asp Met Ala Val Tyr
            100                 105                 110

Tyr Cys Ala Arg Gly Phe Tyr Tyr Gly Ser Gly Thr Asn Tyr Tyr Asn
        115                 120                 125

Arg Gly Met Asp Val Trp Gly Gln Gly Thr Thr Val Thr Val Ser Ser
    130                 135                 140
```

<210> SEQ ID NO 54
<211> LENGTH: 384
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 54

```
atggaaaccc cagcgcagct tctcttcctc ctgctactct ggctcccaga taccaccgga      60
gaaattgtgt tgacgcagtc tccaggcacc ctgtctttgt ctccagggga aagagccacc    120
ctctcctgca gggccagtca gagtgttagc agcagctact tagcctggta ccagcagaaa    180
cctggccagg ctcccaggct cctcatctat ggtgcatcca gcagggccac tggcatccca    240
gacaggttca gtggcagtgg gtctgggaca gacttcactc tcaccatcag cagactggag    300
cctgaagatt ttgcagtgta ttactgtcag cagtatggta gctcaccgta cacttttggc    360
caggggacca agctggagat caaa                                            384
```

<210> SEQ ID NO 55
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Ser Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Ser Ser Pro Tyr Thr Phe Gly Gln Gly Thr Lys Leu Glu Ile Lys
        115                 120                 125

<210> SEQ ID NO 56
<211> LENGTH: 441
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
atggacatac tttgttccac gctcctgcta ctgactgtcc cgtcctgggt cttatcccag    60
gtcaccttga gggagtctgg tcctgcgctg gtgaaaccca cacagaccct cacactgacc   120
tgcaccttct ctgggtctc actcagcact agtggaatgt gtgtgagctg gatccgtcag   180
cccccaggga aggccctgga gtggcttgca gtcattgatt gggatgatga taaatactac   240
aacacatctc tgaagaccag gctcaccatc tccaaggaca cctccaaaaa ccaggtggtc   300
cttacaatga ccaacatgga ccctgtggac acagccacgt attactgtgc acggctacgt   360
attactgtgg ttcggggagt tattataacc tactacggtc tggacgtctg gggccaaggg   420
accacggtca ccgtctcctc a                                            441

<210> SEQ ID NO 57
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Met Asp Ile Leu Cys Ser Thr Leu Leu Leu Leu Thr Val Pro Ser Trp
1               5                   10                  15

Val Leu Ser Gln Val Thr Leu Arg Glu Ser Gly Pro Ala Leu Val Lys
            20                  25                  30

-continued

```
Pro Thr Gln Thr Leu Thr Leu Thr Cys Thr Phe Ser Gly Val Ser Leu
            35                  40                  45

Ser Thr Ser Gly Met Cys Val Ser Trp Ile Arg Gln Pro Pro Gly Lys
 50                  55                  60

Ala Leu Glu Trp Leu Ala Val Ile Asp Trp Asp Asp Lys Tyr Tyr
 65                  70                  75                  80

Asn Thr Ser Leu Lys Thr Arg Leu Thr Ile Ser Lys Asp Thr Ser Lys
                85                  90                  95

Asn Gln Val Val Leu Thr Met Thr Asn Met Asp Pro Val Asp Thr Ala
                100                 105                 110

Thr Tyr Tyr Cys Ala Arg Leu Arg Ile Thr Val Val Arg Gly Val Ile
            115                 120                 125

Ile Thr Tyr Tyr Gly Leu Asp Val Trp Gly Gln Gly Thr Thr Val Thr
 130                 135                 140

Val Ser Ser
145
```

<210> SEQ ID NO 58
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

```
atggaaaccc cagcgcagct tctcttcctc ctgctactct ggctcccaga taccaccgga    60
gaaattgtgt tgacgcagtc tccaggcacc ctgtctttgt ctccagggga aagagccacc   120
ctctcctgca gggccagtca gagtgttagc agcagctact tagcctggta ccagcagaaa   180
cctggccagg ctcccaggct cctcatctat ggtgcatcca gcagggccac tggcatccca   240
gacaggttca gtggcagtgg gtctgggaca gacttcactc tcaccatcag cagactggag   300
cctgaagatt ttgcagtgta ttactgtcag cagtatggta ggtcactcac tttcggccct   360
gggaccaaag tggatatcaa a                                              381
```

<210> SEQ ID NO 59
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

```
Met Glu Thr Pro Ala Gln Leu Leu Phe Leu Leu Leu Leu Trp Leu Pro
 1               5                  10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Ala Ser Gln Ser
            35                  40                  45

Val Ser Ser Tyr Leu Ala Trp Tyr Gln Gln Lys Pro Gly Gln Ala
 50                  55                  60

Pro Arg Leu Leu Ile Tyr Gly Ala Ser Ser Arg Ala Thr Gly Ile Pro
 65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
```

100                 105                 110

Gly Arg Ser Leu Thr Phe Gly Pro Gly Thr Lys Val Asp Ile Lys
        115                 120                 125

<210> SEQ ID NO 60
<211> LENGTH: 432
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
atggagtttg tgctgagctg ggttttcctt gttgctatat taaaaggtgt ccagtgtgag     60
gttcagctgg tgcagtctgg gggaggcttg gtacatcctg gggggtccct gagactctcc    120
tgtgcaggct ctggattcac cttcagtagc tatgctatgc actgggttcg ccaggctcca    180
ggaaaaggtc tggagtgggt atcagttatt ggtcctggtg gtggcacata ctatgcagac    240
tccgtgaagg gccgattcac catctccaga gacaatgcca agaactcctt gtatcttcaa    300
atgaacagcc tgagagccga ggacatggct gtgtatttct gtgcaagagg ctattactat    360
ggttcgggga atttttttaa gaattacggt atggacgtct ggggccaagg gaccacggtc    420
accgtctcct ca                                                        432

<210> SEQ ID NO 61
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Glu Phe Val Leu Ser Trp Val Phe Leu Val Ala Ile Leu Lys Gly
1               5                   10                  15

Val Gln Cys Glu Val Gln Leu Val Gln Ser Gly Gly Gly Leu Val His
            20                  25                  30

Pro Gly Gly Ser Leu Arg Leu Ser Cys Ala Gly Ser Gly Phe Thr Phe
        35                  40                  45

Ser Ser Tyr Ala Met His Trp Val Arg Gln Ala Pro Gly Lys Gly Leu
    50                  55                  60

Glu Trp Val Ser Val Ile Gly Pro Gly Gly Gly Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Met Ala Val Tyr
            100                 105                 110

Phe Cys Ala Arg Gly Tyr Tyr Tyr Gly Ser Gly Asn Phe Phe Lys Asn
        115                 120                 125

Tyr Gly Met Asp Val Trp Gly Gln Gly Thr Thr Val Thr Val Ser Ser
    130                 135                 140

<210> SEQ ID NO 62
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

```
atggaaaccc cagcgcagct tctcttcctc ctgctactct ggctcccaga taccaccgga      60
gaaattgtgt tgacgcagtc tccaggcacc ctgtctttgt ctccagggga aagagccacc     120
ctctcctgca gggccagtca gagtgttagc agcagctact tagcctggta ccagcagaaa     180
cctggccagg ctcccaggct cctcatctat ggtgcatcca gccgggccac tggcatccca     240
gacaggttca gtggcagtgg gtctgggaca gacttcactc tcaccatcag cagactggag     300
cctgaagatt ttgcagtgta ttactgtcag cagtatggtg gctcaccgta cacttttggc     360
caggggacca agctgcagat caaa                                            384
```

<210> SEQ ID NO 63
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

```
Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Ala Ser Gln Ser
            35                  40                  45

Val Ser Ser Ser Tyr Leu Ala Trp Tyr Gln Gln Lys Pro Gly Gln Ala
        50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Gly Ser Pro Tyr Thr Phe Gly Gln Gly Thr Lys Leu Gln Ile Lys
        115                 120                 125
```

<210> SEQ ID NO 64
<211> LENGTH: 438
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64

```
atggagtttg ggctgaactg ggttttcctc gttgctcttt taagaggtgt ccagtgtcag      60
gtgcagctgg tggagtctgg gggaggcgtg gtccagcctg gaggtccct gagactctcc      120
tgtgaagcgt ctggattcac cttcaataac tatgacatga actgggtccg ccaggctcca     180
ggcaaggggc tggagtgggt ggcagttata tggaatgatg aagtaataa atactttgca      240
gactccgtga aggccgatt caccatctcc agagacaatt ccaagaacac gctgtatctg      300
caaatgaaca gcctgagagc cgaggacacg gctgtgtatt actgtgcgag agaggttttt     360
actatggttc gggaattat tataacctac tacggtatgg acgtctgggg ccaagggacc      420
acggtcaccg tctcctca                                                   438
```

<210> SEQ ID NO 65
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Glu Phe Gly Leu Asn Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Glu Ala Ser Gly Phe Thr Phe
        35                  40                  45

Asn Asn Tyr Asp Met Asn Trp Val Arg Gln Ala Pro Gly Lys Gly Leu
    50                  55                  60

Glu Trp Val Ala Val Ile Trp Asn Asp Gly Ser Asn Lys Tyr Phe Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Thr Ala Val
            100                 105                 110

Tyr Tyr Cys Ala Arg Glu Val Phe Thr Met Val Arg Gly Ile Ile Ile
        115                 120                 125

Thr Tyr Tyr Gly Met Asp Val Trp Gly Gln Gly Thr Thr Val Thr Val
    130                 135                 140

Ser Ser
145

<210> SEQ ID NO 66
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
atggaaaccc cagcgcagct tctcttcctc ctgctactct ggctcccaga taccaccgga      60
gaaattgtgt tgacgcagtt tccaggcacc ctgtctttgt ctccagggga agagccacc     120 ctctcctgca gggccagtca gagtgttagc agcagctact tagcctggta ccagcagaaa    180
cctggccagg ctcccaggct cctcatctat ggtgcatcca gcagggccac tggcatccca    240
gacaggttca gtggcagtgg gtctgggaca gacttcactc tcaccatcag cagactggag    300
cctgaagatt ttgcagtgta ttactgtcag cagtatggta ggtcaatcat caccttcggc    360
caagggacac gactggagat taaa                                           384

<210> SEQ ID NO 67
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Met Glu Thr Pro Ala Gln Leu Leu Phe Leu Leu Leu Leu Trp Leu Pro
1               5                   10                  15

-continued

```
Asp Thr Thr Gly Glu Ile Val Leu Thr Gln Phe Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Ser Tyr Leu Ala Trp Tyr Gln Gln Lys Pro Gly Gln Ala
        50                  55                  60

Pro Arg Leu Leu Ile Tyr Gly Ala Ser Ser Arg Ala Thr Gly Ile Pro
65                      70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Arg Ser Ile Ile Thr Phe Gly Gln Gly Thr Arg Leu Glu Ile Lys
            115                 120                 125
```

FULLY HUMAN ANTIBODIES TO BTLA

This application is a divisional of U.S. patent application Ser. No. 13/388,028, filed Mar. 27, 2012, which is a 35 U.S.C. §371 filing of International patent application no. PCT/US2010/043182, which was filed on Jul. 26, 2010, and which claims the benefit of U.S. provisional patent application No. 61/230,332 filed Jul. 31, 2009, and U.S. Provisional patent application No. 61/257,612 filed Nov. 3, 2009, each of which are herein incorporated by reference in their entireties.

FIELD OF THE INVENTION

The present invention relates generally to antibodies or antigen binding fragments that bind to BTLA and uses thereof. More specifically, the invention relates to fully human antibodies that recognize human BTLA and modulate its activity, particularly in inflammatory, autoimmune and proliferative disorders.

BACKGROUND OF THE INVENTION

The immune system functions to protect individuals from infectious agents, e.g., bacteria, multi-cellular organisms, and viruses, as well as from cancers. This system includes several types of lymphoid and myeloid cells such as monocytes, macrophages, dendritic cells (DCs), eosinophils, T cells, B cells, and neutrophils. These lymphoid and myeloid cells often produce signaling proteins known as cytokines. The immune response includes inflammation, i.e., the accumulation of immune cells systemically or in a particular location of the body. In response to an infective agent or foreign substance, immune cells secrete cytokines which, in turn, modulate immune cell proliferation, development, differentiation, or migration. Immune responses can produce pathological consequences, e.g., when it involves excessive inflammation, as in the autoimmune disorders (see, e.g., Abbas et al. (eds.) (2000) *Cellular and Molecular Immunology*, W.B. Saunders Co., Philadelphia, Pa.; Oppenheim and Feldmann (eds.) (2001) *Cytokine Reference*, Academic Press, San Diego, Calif.; von Andrian and Mackay (2000) *New Engl. J. Med.* 343:1020-1034; Davidson and Diamond (2001) *New Engl. J. Med.* 345:340-350).

Positive and negative co-stimulatory signals play critical roles in the modulation of B and T cell activity, and the molecules that mediate these signals have proven to be effective targets for immunomodulatory agents. Positive co-stimulation, in addition to T cell receptor (TCR) engagement, is required for optimal activation of naive T cells, whereas negative co-stimulation is believed to be required for the acquisition of immunologic tolerance to self, as well as the termination of effector T cell functions. Upon interaction with B7.1 or B7.2 on the surface of antigen-presenting cells (APC), CD28, the prototypic T cell costimulatory molecule, emits signals that promote T cell proliferation and differentiation in response to TCR engagement, while the CD28 homologue cytotoxic T lymphocyte antigen-4 (CTLA-4) mediates inhibition of T cell proliferation and effector functions (Chambers et al, Ann. Rev. Immunol., 19:565-594, 2001; Egen et al., Nature Immunol, 3:611-618, 2002). Several new molecules with homology to the B7 family have been discovered (Abbas et al, Nat. Med., 5:1345-6, 1999; Coyle et al., Nat. Immunol., 2: 203-9, 2001; Carreno et al., Annu. Rev. Immunol., 20: 29-53, 2002; Liang et al., Curr. Opin. Immunol., 14: 384-90, 2002), and their role in T cell activation is just beginning to be elucidated.

These new costimulatory ligands include B7h, PD-L1, PD-L2, and B7-H3. B7h (Swallow et al, Immunity, 11: 423-32, 1999), also known as B7RP-1 (Yoshinaga et al, Nature, 402: 827-32, 1999), GL50 (Ling, et al, J. Immunol., 164:1653-7, 2000), B7H2 (Wang et al, Blood, 96: 2808-13, 2000), and LICOS (Brodie et al, Curr. Biol., 10: 333-6, 2000), binds to an inducible costimulator (ICOS) on activated T cells, and costimulates T cell proliferation and production of cytokines such as interleukin 4 (IL-4) and IL-10.

PD-L1 (Freeman et al, J. Exp. Med., 192: 1027-34, 2000), also known as B7-H1 (Dong et al, Nat. Med., 5, 1365-9, 1999), and PD-L2 (Latchman et al, Nat. Immunol., 2:261-8, 2001), also known as B7-DC (Tseng et al, J. Exp. Med., 193, 839-46, 2001) bind to programmed death 1 (PD-I) receptor on T and B cells.

Finally, B7-H3 binds an as yet currently unknown counter-receptor on activated T cells, and is reported to enhance proliferation of CD4+ T helper (Th) cells and CD8+ cytotoxic T lymphocytes (CTLs or Tcs) and selectively enhance IFN-γ expression (Chapoval et al, Nat. Immunol, 2, 269-74, 2001; Sun et al, J. Immunol., 168, 6294-7, 2002).

The identification of additional molecules that have T cell costimulatory activity is of keen interest due to their fundamental biological importance and the therapeutic potential of agents capable of affecting their activity. Agents capable of modulating costimulatory signals, and thereby capable of modulating the activation and/or effector functions of CD8+ CTLs and CD4+ Th cells find use in the modulation of immune responses, and are highly desirable.

In particular, many autoimmune disorders are known to involve autoreactive T cells and autoantibodies. Agents that are capable of inhibiting or eliminating autoreactive lymphocytes without compromising the immune system's ability to defend against pathogens are highly desirable.

Conversely, many cancer immunotherapies, such as adoptive immunotherapy, expand tumor-specific T cell populations and direct them to attack and kill tumor cells (Dudley et al., Science 298:850-854, 2002; Pardoll, Nature Biotech., 20: 1207-1208, 2002; Egen et al., Nature Immunol., 3:611-618, 2002). Agents capable of augmenting tumor attack are also highly desirable.

In addition, immune responses directed against different antigens (e.g., microbial antigens or tumor antigens), while detectable, are frequently of insufficient magnitude to afford protection against a disease process mediated by agents (e.g., infectious microorganisms or tumor cells) expressing those antigens. It is often desirable to administer to the subject, in conjunction with the antigen, an adjuvant that serves to enhance the immune response to the antigen in the subject.

It is also desirable to inhibit normal immune responses to antigen under certain circumstances. For example, the suppression of normal immune responses in a patient receiving a transplant is desirable, and agents that exhibit such immunosuppressive activity are highly desirable.

Costimulatory signals, particularly positive costimulatory signals, also play a role in the modulation of B cell activity. For example, B cell activation and the survival of germinal center B cells require T cell-derived signals in addition to stimulation by antigen.

CD40 ligand present on the surface of helper T cells interacts with CD40 on the surface of B cells, and mediates many such T-cell dependent effects in B cells.

The protein BTLA (B and T lymphocyte attenuator) is a member of the CD28 family of receptors that also includes CD28, CTLA-4, ICOS, and PD-1. The initial members of the family, CD28 and ICOS, were discovered by functional effects on augmenting T cell proliferation following the addition of monoclonal antibodies (Hutloff et al. (1999) Nature 397:263-266; Hansen et al. (1980) Immunogenics 10:247-260). BTLA was discovered through screening for differential expression in TH1 cells. In addition, BTLA has been described as providing negative inhibitory signals, analogous to CTLA-4. In the presence of agonist anti-BTLA Mab, anti-CD3 and anti-CD28 activated T-cells show reduced IL-2 production and proliferation (Kreig et al., J. Immunol., 175, 6420-6472, 2005). Mice lacking an intact BTLA gene show higher titers to DNP-KLH post-immunization and an increased sensitivity to EAE (Watanabe et al., Nat. Immunol, 4, 670-679, 2003). HVEM (herpes virus entry mediator) has been shown to be a ligand for BTLA (Scully et al. (2005) Nat. Immunol. 6:90-98; Gonzalez et al. (2005) Proc. Nat. Acad. Sci. U.S.A. 102: 1116-1121).

Accordingly, agents that recognize BTLA, in particular antibodies and binding agents thereof that recognize BTLA, and methods of using such agents, are desired.

Antibodies can be used as therapeutic agents. Certain antibodies when used as a therapeutic agent in vivo can cause undesired immunogenicity of the antibodies. As most monoclonal antibodies are derived from rodents, repeated use in humans results in the generation of an immune response against the therapeutic antibody, e.g., human against mouse antibodies or HAMA. Such an immune response results in a loss of therapeutic efficacy at a minimum and a potential fatal anaphylactic response at a maximum. One approach for reducing the immunogenicity of rodent antibodies involves the production of chimeric antibodies, in which mouse variable regions (Fv) were fused with human constant regions (Liu et al. (1987) Proc. Natl. Acad. Sci. USA 84:3439-43). However, mice injected with hybrids of human variable regions and mouse constant regions develop a strong anti-antibody response directed against the human variable region, suggesting that the retention of the entire rodent Fv region in such chimeric antibodies may still result in unwanted immunogenicity in patients.

Additionally, grafting of rodent complementarity determining region (CDR) loops of variable domains onto human frameworks (i.e., humanization) has been used to further minimize rodent sequences. Jones et al. (1986) Nature 321: 522; Verhoeyen et al. (1988) Science 239:1534. However, CDR loop exchanges still do not uniformly result in an antibody with the same binding properties as the antibody of origin. Changes in framework residues (FR), residues involved in CDR loop support, in humanized antibodies also are often required to preserve antigen binding affinity. Kabat et al. (1991) J. Immunol. 147:1709. While the use of CDR grafting and framework residue preservation in a number of humanized antibody constructs has been reported, it is difficult to predict if a particular sequence will result in the antibody with the desired binding, and sometimes biological, properties. See, e.g., Queen et al. (1989) Proc. Natl. Acad. Sci. USA 86:10029, Gorman et al. (1991) Proc. Natl. Acad. Sci. USA 88:4181, and Hodgson (1991) Biotechnology (NY) 9:421-5. Moreover, most prior studies used different human sequences for animal light and heavy variable sequences, rendering the predictive nature of such studies questionable. Sequences of known antibodies have been used or, more typically, those of antibodies having known X-ray crystal structures, such as antibodies NEW and KOL. See, e.g., Jones et al., supra; Verhoeyen et al., supra; and Gorman et al., supra. Exact sequence information has been reported for a few humanized constructs.

The need exists for anti-BTLA antibodies, and in particular anti-BTLA monoclonal antibodies, for use in treatment of human disorders, such as inflammatory, autoimmune, and proliferative disorders. Such antibodies will preferably exhibit low immunogenicity in human subjects, allowing for repeated administration without adverse immune responses.

SUMMARY OF THE INVENTION

The present invention relates to anti-human BTLA antibodies having one or more desirable properties, including high binding affinities, neutralizing activities, good pharmacokinetics and low antigenicity in human subjects. The invention also relates to use of the antibodies of the present invention in the treatment of disease.

In certain embodiments, the invention relates to an isolated antibody or antigen binding fragment thereof which binds to human B and T lymphocyte attenuator (BTLA), comprising one or more properties selected from the group consisting of: a) does not block binding of BTLA to herpes virus entry mediator (HVEM); b) cross reacts with cynomolgus BTLA; c) exhibits a $K_D$ for binding to human BTLA of at most about $2.4 \times 10^{-9}$; and d) exhibits an $EC_{50}$ of from about 10-100 nM in an in in vitro assay measuring B or T cell activation.

In additional embodiments, the invention relates to an isolated antibody or antigen binding fragment thereof which binds to human BTLA, comprising one of more properties selected from the group consisting of: a) blocks binding of BTLA to HVEM; b) cross reacts with cynomolgus BTLA; and c) exhibits a $K_D$ for binding to human BTLA of at most about $4.6 \times 10^{-9}$.

In additional embodiments, the invention relates to an isolated agonist antibody or antigen binding fragment thereof which binds BTLA selected from the group consisting of hu Mab8D5 and hu Mab8A3, wherein the antibody specifically binds BTLA and does not block binding to HVEM.

In additional embodiments, the invention relates to an isolated agonist antibody or antigen binding fragment thereof which binds BTLA selected from the group consisting of hu Mab21H6 hu and Mab19A7, wherein the antibody specifically binds BTLA and also blocks binding to HVEM.

In yet additional embodiments the invention relates to an isolated antibody or antigen binding fragment thereof which binds BTLA comprising at least one $V_L$ CDR domain selected from the group consisting of SEQ ID Nos.:12, 13, and 14 and at least one $V_H$ CDR domain selected from the group consisting of SEQ ID Nos.: 5, 6, and 7.

In yet additional embodiments the invention relates to an isolated antagonist antibody or antigen binding fragment thereof which binds BTLA, comprising at least one $V_L$ CDR domain selected from the group consisting of SEQ ID Nos.: 26, 27, 28, and at least one $V_H$ CDR domain selected from the group consisting of SEQ ID Nos.: 19, 20, and 21.

In yet additional embodiments the invention relates to an isolated antibody or antigen binding fragment thereof, comprising a heavy chain variable region and a light chain variable region, wherein: (a) the heavy chain variable region comprises the amino acid sequence of SEQ ID NO: 11 (8D5 heavy chain); and (b) the light chain variable region comprises the amino acid sequence of SEQ ID NO: 18 (8D5 light chain).

In yet additional embodiments the invention relates to an isolated antibody or antigen binding fragment thereof, comprising: (a) a heavy chain variable region CDR1 comprising the amino acid sequence of SEQ ID NO:5 (8D5 HCDR1); (b) a heavy chain variable region CDR2 comprising the amino acid sequence of SEQ ID NO:6 (8D5 HCDR2); (c) a heavy chain variable region CDR3 comprising the amino acid sequence of SEQ ID NO:7 (8D5 HCDR3); (d) a light chain variable region CDR1 comprising the amino acid sequence of SEQ ID NO: 12(8D5 LCDR1); (e) a light chain variable region CDR2 comprising the amino acid sequence of SEQ ID NO:13 (8D5 LCDR2); and (f) a light chain variable region CDR3 comprising the amino acid sequence of SEQ ID NO: 14(8D5 LCDR3); wherein the antibody specifically binds BTLA and does not block binding to HVEM.

In yet additional embodiments the invention relates to an isolated antibody or antigen binding fragment thereof, comprising: (a) a heavy chain variable region that is the product of or derived from a human VH gene (SEQ ID NO:8) [encoding 8D5]; and (b) a light chain variable region that is the product of or derived from a human VK gene (SEQ ID NO:15) [encoding 8D5]; wherein the antibody specifically binds BTLA.

In yet additional embodiments the invention relates to an isolated antibody or antigen binding fragment thereof, wherein the antibody cross-competes for binding to BTLA with a reference antibody that comprises: (a) the heavy chain variable region comprises the amino acid sequence of SEQ ID NO: 9 or SEQ ID NO:11 (8D5 heavy chain); (b) the light chain variable region comprises the amino acid sequence of SEQ ID NO:16 or SEQ ID NO:18 (8D5 light chain); wherein the isolated monoclonal antibody, or antigen-fragment thereof, is a BTLA agonist.

In certain embodiments, the heavy chain and light chain are connected by a flexible linker to form a single-chain antibody.

In certain embodiments, the antibody or antigen binding fragment is a single-chain Fv antibody. In certain embodiments, the antibody or antigen binding fragment is a Fab antibody. In certain embodiments, the antibody or antigen binding fragment is a Fab' antibody. In certain embodiments, the antibody or antigen binding fragment is a (Fab')$_2$ antibody.

In certain embodiments, the antibody or antigen binding fragment is a fully human monoclonal or recombinant antibody.

In certain embodiments, the antibody or antigen binding fragment decreases BTLA activity and/or signaling.

In certain embodiments, the antibody or antigen binding fragment increases BTLA activity and/or signaling.

In yet additional embodiments, the invention relates to an isolated polypeptide comprising the $V_L$ domains or the $V_H$ domains of any of the antibodies or antigen binding fragments described herein.

In yet additional embodiments, the invention relates to an isolated nucleic acid encoding the $V_L$ domains or the $V_H$ domains of any of the antibodies or antigen binding fragments described herein.

In yet additional embodiments, the invention relates to a composition comprising one or more antibodies or antigen binding fragments as described herein and a pharmaceutically acceptable carrier or diluent.

In yet additional embodiments, the invention relates to a method of treating a condition caused by decreased expression and/or activity of BTLA in a subject, comprising administering to the subject an effective amount of the pharmaceutical composition as described herein. In particular, any disease or disorder marked by the presence or activity of T or B cells can be treated by a BTLA agonist antibody (i.e., a disease or disorder that involves the presence of BTLA positive immune cells can be managed or treated by activating BTLA receptor function). In certain embodiments, the one or more antibodies or antigen binding fragment thereof is selected from the group consisting of hu Mab8D5, hu Mab8A3, hu Mab21H6, hu Mab19A7, or hu Mab4C7.

In yet additional embodiments, the invention relates to a method of treating an inflammatory or autoimmune disorder in a subject comprising administering an effective amount of the antibody or antigen binding fragments as described herein to the subject. In certain embodiments, the inflammatory or autoimmune disorder is selected from the group consisting of inflammatory bowel disorders (e.g., Crohn's disease, ulcerative colitis, and inflammatory bowel disease), inflammatory fibrosis (e.g., scleroderma, lung fibrosis, and cirrhosis), rheumatoid arthritis (RA), osteoarthritis, osteoporosis, asthma (including allergic asthma), allergies, chronic obstructive pulmonary disease (COPD), multiple sclerosis, psoriasis, uveitis, graft versus host disease (GVHD), juvenile early-onset Type I diabetes, transplant rejection, SLE, and Sjögren's syndrome. Such methods of treatment may further comprise administering one or more additional therapeutic agents, such as immunosuppressive or anti-inflammatory agents. In yet additional embodiments, the disorder is rheumatoid arthritis.

In yet additional embodiments, the inflammatory bowel disorder is selected from the group consisting of Crohn's disease, ulcerative colitis, and inflammatory bowel disease.

In yet additional embodiments, the invention relates to a method of treating transplant rejection and/or graft-versus-host disease.

In yet additional embodiments, the invention relates to a method of treating diabetes type I.

In yet additional embodiments, the invention relates to the use of the antibody or antigen binding fragment as described herein for the preparation of a medicament to treat an inflammatory or autoimmune disorder in a subject.

In yet additional embodiments, the invention relates to the use of the antibody or antigen binding fragment as described herein for the preparation of a medicament to decrease the activity of BTLA.

In yet additional embodiments, the invention relates to a method of increasing the immune response in a subject comprising administering an effective amount of the pharmaceutical composition to the subject. In certain embodiments, the one or more antibodies or antigen binding fragment thereof is hu Mab4C7.

In yet additional embodiments, the invention relates to the use of an antagonist antibody as described herein for the preparation of a medicament to increase the activity of BTLA.

In yet additional embodiments, the invention relates to the use of any of the antibody or antibody fragments described herein for diagnostic use.

In yet additional embodiments, the invention relates to a kit comprising any of the antibodies of or antigen binding fragments described herein.

In yet additional embodiments, the invention relates to a complex comprising BTLA and any one of the antibody or antigen binding fragments described herein.

In yet additional embodiments, the invention relates to an expression vector comprising the isolated nucleic acid encoding a polypeptide encoding any of the VH or VL chains described herein. In yet additional embodiments, the invention relates to host cell comprising the expression vector described herein.

In yet additional embodiments, the invention relates to a method of producing the antibody of antigen binding fragment thereof as described herein comprising:

(a) culturing the host cell described herein in culture medium under conditions wherein the nucleic acid sequence is expressed, thereby producing polypeptide comprising the light and heavy chain variable regions; and (b) recovering the polypeptides from the host cell or culture medium.

In yet additional embodiments, the invention relates to an isolated antibody or antigen binding fragment thereof, wherein the antibody cross-competes for binding to BTLA with a reference antibody that comprises:

(a) the heavy chain variable region comprises the amino acid sequence of SEQ ID NO: 23 (4C7 heavy chain);

(b) the light chain variable region comprises the amino acid sequence of SEQ ID NO:30 (4C7 light chain); wherein the isolated monoclonal antibody, or antigen-fragment thereof, is a BTLA antagonist.

In yet additional embodiments, the invention relates to an isolated nucleic acid encoding an immunoglobulin polypeptide comprising CDR-L1, CDR-L2 and CDR-L3 found in a light chain variable region that comprises the amino acid sequence set forth in SEQ ID NO:18.

In yet additional embodiments, the invention relates to an isolated immunoglobulin polypeptide comprising CDR-L1, CDR-L2 and CDR-L3 found in a light chain variable region that comprises the amino acid sequence set forth in SEQ ID NO:18.

In yet additional embodiments, the invention relates to an isolated nucleic acid encoding an immunoglobulin polypeptide comprising CDR-H1, CDR-H2 and CDR-H3 found in a heavy chain variable region that comprises the amino acid sequence set forth in SEQ ID NO:11.

In yet additional embodiments, the invention relates to an isolated immunoglobulin polypeptide comprising CDR-H1, CDR-H2 and CDR-H3 found in a heavy chain variable region that comprises the amino acid sequence set forth in SEQ ID NO:11.

In yet additional embodiments, the invention relates to an isolated nucleic acid encoding an immunoglobulin polypeptide comprising CDR-L1, CDR-L2 and CDR-L3 found in a light chain variable region that comprises the amino acid sequence set forth in SEQ ID NO:32.

In yet additional embodiments, the invention relates to an isolated immunoglobulin polypeptide comprising CDR-L1, CDR-L2 and CDR-L3 found in a light chain variable region that comprises the amino acid sequence set forth in SEQ ID NO:32.

In yet additional embodiments, the invention relates to an isolated nucleic acid encoding an immunoglobulin polypeptide comprising CDR-H1, CDR-H2 and CDR-H3 found in a heavy chain variable region that comprises the amino acid sequence set forth in SEQ ID NO: 25.

In yet additional embodiments, the invention relates to an isolated immunoglobulin polypeptide comprising CDR-H1, CDR-H2 and CDR-H3 found in a heavy chain variable region that comprises the amino acid sequence set forth in SEQ ID NO:25.

In certain embodiments, these nucleic acid constructs and/or polypeptides are useful in methods of making an antibody.

BRIEF DESCRIPTION OF THE DRAWINGS

FIGS. 1A-C show the sequences of the heavy and light chain variable regions of hu Mab 8D5. FIG. 1A shows the mature amino acid sequence of VH chain and the encoding nucleic acid sequence. The CDR1, CDR2, and CDR3 sequences are indicated with waved lines above the amino acid sequence. FIG. 1B shows the mature amino acid sequence of the VL chain and the encoding nucleic acid sequence. The CDR1, CDR2, and CDR3 sequences are indicated with waved lines above the amino acid sequence. FIG. 1C shows sequence features of the heavy and light chain variable regions of Hu Mab8D5.

FIGS. 2A-C show the sequences of the heavy and light chain variable regions of hu Mab 4C7. FIG. 2A shows the mature amino acid sequence of VH chain and the encoding nucleic acid sequence. The CDR1, CDR2, and CDR3 sequences are indicated with waved lines above the amino acid sequence. FIG. 2B shows the mature amino acid sequence of the $V_K$ and the encoding nucleic acid sequence. The CDR1, CDR2, and CDR3 sequences are indicated with waved lines above the amino acid sequence. FIG. 2C shows sequence features of the heavy and light chain variable regions of hu Mab4C7.

FIG. 3A shows the binding profile of hu Mab8D5 for human BTLA expressed on CHO cells. FIG. 3B shows the binding profile of hu Mab8D5 for cyno BTLA expressed on CHO cells. FIG. 3C shows the binding profile of hu Mab4C7 for human BTLA expressed on CHO cells. FIG. 3D shows the binding profile of hu Mab4C7 for cyno BTLA expressed on CHO cells.

FIG. 4A shows that hu Mab4C7 blocks human HVEM binding to CHO cells expressing human BTLA. FIG. 4B shows that hu Mab8D5 fails to block human HVEM binding to CHO cells expressing human BTLA.

FIGS. 12A-B are Western blots showing hu Mab8D5 and hu Mab4C7 (FIG. 12A) binding to BTLA and hu Mab8D5 reducing TCR4 phosphorylation (FIG. 12B).

DETAILED DESCRIPTION OF THE INVENTION

Figure 3A:
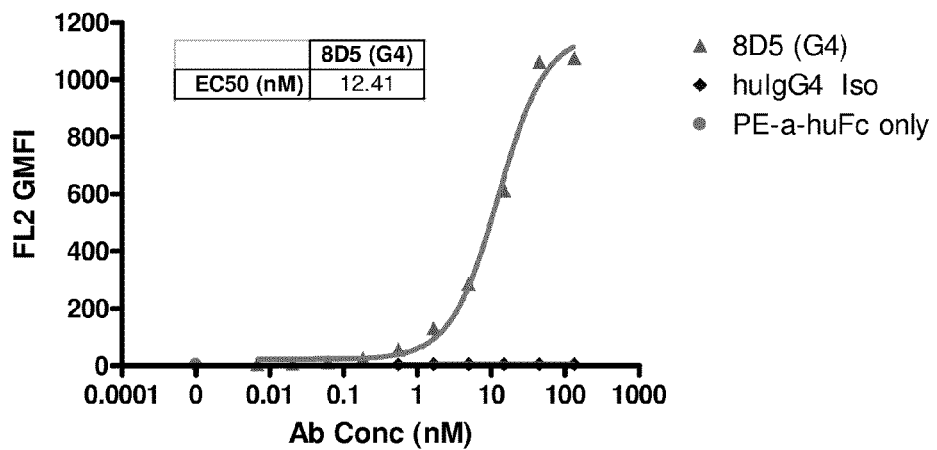
FIGS. 3A-D show binding and cross reactivity features of hu Mab8D5 and hu Mab4C7.

The mammalian immune system has developed several pathways to harness the potentially harmful activities of T and B lymphocytes. These include a wide variety of cytokine-receptor pathways as well as costimulation pathways involving receptors like CD28, CTLA-4, PD-1 and BTLA. Whereas the CD28-B7 interaction is an example of a positive costimulatory pathway (i.e., CD28 triggering enhances T cell responses to antigen specific triggers), the other three receptors are representations of inhibitory costimulation pathways. CTLA-4, PD-1 and BTLA show overlapping, but distinct expression profiles, and limit the activity of T and B lymphocytes as well as other immune cells in a non-redundant fashion. (See, Deppong et al. J Immunol 2006, Tao et al., J Immunol 2005). Whereas CTLA-4 competes with CD28 for binding of B7.1 and B7.2 (CD80 and CD86) and sets a primordial threshold for naïve T cell activation in lymph nodes and spleen, PD-1 and BTLA each have their own unique ligands (PD-L1/-L2 and HVEM, respectively) and appear to control peripheral T cell homeostasis and re-activation. (See, Krieg et al. Nat Immunol 2007.)

BTLA Downregulates B and T Cell Activation

As indicated by its name, B- and T-Lymphocyte Attenuator (BTLA) is expressed on both resting and activated B- and T-lymphocytes. BTLA is a type I transmembrane glycoprotein and has a cytoplasmic tail which contains several inhibitory tyrosine motifs (Watanabe, 2003). BTLA bears some structural similarity to members of the CD28/CTLA-4 family, but several factors make it a unique member. Human BTLA contains the following characterized domains: Ig extracellular domain: residues 51-117; transmembrane domain: residues 153-173; ITIM domain: residues 255-260; and an ITSM domain: residues 280-285 (with reference to human SEQ ID NO:2). ITIM stands for immunoreceptor tyrosine-based inhibition motif, while ITSM stands for immunoreceptor tyrosine-based switch motif.

The BTLA Ig intermediate-type (I set-type) extracellular domain corresponding to residues 43-134 of SEQ ID NO:2 is responsible for ligand binding and is not found in other members of the CD28/CTLA-4 family. In addition, the ligand for BTLA is not a B7 family member, but rather it is the TNFR superfamily receptor herpesvirus entry mediator (HVEM) (Sedy, 2005). HVEM is expressed on peripheral B and T cells and monocytes, and the crystal structure of HVEM bound to BTLA has been solved (Compaan, 2005).

Several in vivo studies demonstrated the inhibitory role for BTLA in lymphocyte responses. BTLA-deficient mice generated by Murphy and co-workers (Washington University St. Louis) exhibited a three-fold increase in IgG production in response to T-dependent antigen. In addition, T and B cells isolated from BTLA$^{-/-}$ mice showed a greater proliferative response to antigen-receptor stimulation using –CD3 and anti-IgM, respectively (Watanabe, 2003). In overexpression studies, BTLA was found associated with the B cell receptor complex and with the T cell receptor. In line with this finding, antigen-receptor independent stimulation using Con A (T cells) or LPS (B cells) is not affected in BTLA deficient lymphocytes and cannot be modulated using anti-BTLA antibodies.

BTLA knockout mice have been shown to develop spontaneous autoimmune disease over time and have a decreased lifespan (Oya, 2008). Ligation of BTLA by HVEM leads to downregulation of T cell activation and proliferation (Sedy, 2005). BTLA knockout mice exhibit increased disease severity in autoimmune encephalomyelitis (EAE) and allergic airway inflammation models, both of which are dependent on T cell activity (Watanabe, 2005; Deppong, 2006). An association between a SNP in the human BTLA gene and susceptibility to RA has also been shown (Lin, 2006). However, little is yet known about the role of BTLA signaling in pathological conditions.

Thus, for autoimmune and certain proliferative diseases, there is an ongoing need to develop treatments that exploit the inhibitory role of BTLA in lymphocyte responses, while allowing for BTLA-HVEM binding.

Agonist BTLA antibodies are particularly well-suited for this role. In the course of selection of over 200 mAbs generated using the Ultimab platform, a number of agonist antibodies and antagonist BTLA antibodies were identified. Out of the over 200 mAbs, several antibodies including hu Mab8D5, hu Mab8A3, hu Mab21H6, and hu Mab19A7 were identified that activate inhibitory BTLA receptor function (i.e., agonist antibodies). Hu Mab8D5 and hu Mab8A3 are BTLA agonists that do not block HVEM ligand binding to BTLA. Hu Mab21H6 and hu Mab19A7 activate inhibitory BTLA receptor function while also blocking HVEM ligand binding to BTLA. These agonist antibodies exhibit ~12-14 nM binding affinity for BTLA, and also inhibit T and B cell responses in human donor blood with an EC50 of ~30-100 nM. When re-expressed as an IgG4, as well as a monovalent Fab' fragment, hu Mab8D5 maintained its immune inhibitory activity in vitro. These agonist BTLA antibodies also bind to cynomolgus BTLA with similar affinity and demonstrate equivalent inhibition of cynomolgus T cell responses. However, these agonist antibodies do not cross-react with mouse BTLA. In mouse pharmacological studies, hu Mab8D5 exhibited a half-life of ~16 days, consistent with expectations for a human IgG4. These receptor agonistic mAbs inhibit and suppress T and B lymphocyte activity in vitro, and also exhibit such activity in in vivo model systems. Agonist antibodies of the present invention are distinguished by having the ability to inhibit B cell activation by cognate antigen without depleting the B cells. Additionally, agonist antibodies of the present invention are also distinguished by the ability to target B and T cell activation simultaneously.

In addition to the four agonist anti-BTLA antibodies described above, the selection also identified an antagonist antibody hu Mab4C7. This antibody exhibits immune stimulating effects as shown in FIGS. 6C-D and FIGS. 8A-B and therefore is expected to be useful as a cancer treatment, or for treatment of certain pathogenic infections, and as an adjuvant to a vaccine. The use of a BTLA antagonist such as Mab4C7 for stimulating the immune response in the context of cancer is expected to correlate with these results as well as results illustrating that blocking BTLA-HVEM ligation during priming of naïve CD8+ T cells contributes to enhanced T cell proliferation. (See, Derré et al. J. Clin. Invest. 2010, 120: 157-167).

For BTLA agonists, the ability to suppress both antigen-specific T and B cell responses will provide methods for modulating BTLA activity that are expected to be useful for conditions such as arthritis, SLE, Sjogren's disease, ulcerative colitis and Crohn's disease, as well as solid organ transplants (i.e., kidney, liver and other organs, including tissue transplants). Current treatments exhibit deficiencies in part because suppressing T cells alone is not sufficient to achieve the desired effects. The anti-BTLA antibodies of the present invention may be efficacious for the treatment of arthritis, ulcerative colitis and Crohn's disease, as well as solid organ transplants (i.e., kidney, liver and other organs) by the ability to suppress both T- and B-cell responses. The ability of each of the agonist antibodies of the present invention, when re-expressed as an IgG4, as well as a monovalent Fab' fragment to maintain immune inhibitory activity in vitro and in vivo models, provides desirable traits for novel treatments.

ABBREVIATIONS

Throughout the detailed description and examples of the invention the following abbreviations will be used:

ADCC Antibody-dependent cellular cytotoxicity
BTLA B- and T-Lymphocyte Attenuator
HVEM Herpes Virus Entry Mediator
Hu Mab8D5 fully human monoclonal agonist anti-BTLA antibody
Hu Mab8A3 fully human monoclonal agonist anti-BTLA antibody
Hu Mab21H6 fully human monoclonal agonist anti-BTLA antibody
Hu Mab19A7 fully human monoclonal agonist anti-BTLA antibody
Hu Mab4C7 fully human monoclonal antagonist anti-BTLA antibody
Hu Mab 20H4 fully human monoclonal anti-BTLA antibody
Hu Mab 15C5 fully human monoclonal anti-BTLA antibody
CDC Complement-dependent cyotoxicity
CDR Complementarity determining region in the immunoglobulin variable regions, defined using the Kabat numbering system
CHO Chinese hamster ovary
CTL Cytotoxic T lymphocyte
EC50 concentration resulting in 50% efficacy or binding
ELISA Enzyme-linked immunosorbant assay
FW Antibody framework region: the immunoglobulin variable regions excluding the CDR regions
HRP Horseradish peroxidase
IL-2 interleukin 2
IL-5 interleukin 5
IFN interferon
IC50 concentration resulting in 50% inhibition
IgG Immunoglobulin G
Kabat An immunoglobulin alignment and numbering system pioneered by Elvin A. Kabat ((1991) Sequences of Proteins of Immunological Interest, 5th Ed. Public Health Service, National Institutes of Health, Bethesda, Md.)
mAb or Mab or MAb Monoclonal antibody
MES 2-(N-morpholino)ethanesulfonic acid
MOA Mechanism of action
NHS Normal human serum
PCR Polymerase chain reaction
PK Pharmacokinetics
SEB *Staphylococcus* Enterotoxin B
TT Tetanus toxoid
V region The segment of IgG chains which is variable in sequence between different antibodies. It extends to Kabat residue 109 in the light chain and 113 in the heavy chain.
VH Immunoglobulin heavy chain variable region
VK Immunoglobulin kappa light chain variable region

DEFINITIONS

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"Activation," "stimulation," and "treatment," as it applies to cells or to receptors, may have the same meaning, e.g., activation, stimulation, or treatment of a cell or receptor with a ligand, unless indicated otherwise by the context or explicitly. "Ligand" encompasses natural and synthetic ligands, e.g., cytokines, cytokine variants, analogues, muteins, and binding compounds derived from antibodies. "Ligand" also encompasses small molecules, e.g., peptide mimetics of cytokines and peptide mimetics of antibodies. "Activation" can refer to cell activation as regulated by internal mechanisms as well as by external or environmental factors. "Response," e.g., of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming.

"Activity" of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" can also mean specific activity, e.g., [catalytic activity]/[mg protein], or [immunological activity]/[mg protein], concentration in a biological compartment, or the like. "Activity" may refer to modulation of components of the innate or the adaptive immune systems. "Proliferative activity" encompasses an activity that promotes, that is necessary for, or that is specifically associated with, e.g., normal cell division, as well as cancer, tumors, dysplasia, cell transformation, metastasis, and angiogenesis.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. The term "subject" includes any organism, preferably an animal, more preferably a mammal (e.g., rat, mouse, dog, cat, rabbit) and most preferably a human.

As used herein, a BTLA agonist antibody refers to an antibody that binds to BTLA and enhances its coinhibitory signal to B and T cells.

As used herein, a BTLA antagonist antibody refers to an antibody that binds to BTLA and prevents the coinhibitory signal delivery to B and T cells.

In an embodiment of the invention, where possible, a composition of the invention is administered to a subject in accordance with the Physicians' Desk Reference 2003 (Thomson Healthcare; 57th edition (Nov. 1, 2002)).

In certain embodiments, the anti-BTLA antibody or antigen binding fragment thereof can be administered by an invasive route such as by injection (see above). Administration by a non-invasive route (e.g., orally; for example, in a pill, capsule or tablet) is also within the scope of the present invention. In an embodiment of the invention, an anti-BTLA antibody or antigen binding fragment thereof, or pharmaceutical composition thereof, is administered intravenously, subcutaneously, intramuscularly, intraarterially, intra-articular (e.g. in arthritis joints), by inhalation, aerosol delivery, or intratumorally. In certain embodiments, the anti-BTLA antibody or antigen binding fragment thereof is administered in combination with a chemotherapeutic agent (e.g., gefitinib (e.g., Iressa™)) administered orally in tablet form. In another embodiment, the chemotherapeutic agent is paclitaxel (e.g., Taxol®) which is administered intravenously.

In yet another embodiment, the anti-BTLA antibody or antigen binding fragment thereof is administered in combination with at least one additional therapeutic agent, such as, but not limited to other monoclonal antibodies directed to CTLA-4 (e.g., AVASTIN (bevacizumab), MYLOTARG (gemtuzumab), BEXXAR (tositumomab), RITUXAN (rituximab), HERCEPTIN (trastuzumab)), or protein ligands having similar effects; agents that activate antigen presenting cells (dendritic cells, macrophages, B cells, monocytes), including type 1 interferons (e.g., interferon alpha and beta); interferon gamma; BCG; agents that provide tumor antigens in any and all forms, including protein antigens, peptide antigens, whole cell lysates and derivatives thereof; genetically encoded antigens (e.g., adenovirus encoded antigens); cellular components of the immune system that have been altered either in vivo or ex vivo to enhance their immune properties (e.g., autologous dendritic cells, lymphocytes, heat shock proteins, etc.); chemotherapeutic agents such as, but not limited to, cyclophosphamide, methotrexate, etoposide, adriamycin, taxanes, fluorouracil, cytosine arabinoside (AraC), and platinum-containing agents, among numerous others. Examples of antigens include PSA antigens (e.g., PROSTVAC/TRICOM) and melanoma-derived gp100 antigens. The combination may also be administered in combination with a cytokine or growth factor such as but not limited to GM-CSF, or with an immunostimulatory nucleotide, such as but not limited to CpG ODN PF3512676 (also known as ProMune, See WO2007/008463).

Additionally, in certain embodiments, the anti-BTLA antibody or antigen binding fragment thereof can be administered in combination with antibodies such as anti-CTLA-4 and anti-PD1, including those described in U.S. Pat. No. 6,682,736 and U.S. Pat. No. 7,563,869, respectively.

Compositions can be administered with medical devices known in the art. For example, a pharmaceutical composition of the invention can be administered by injection with a hypodermic needle.

The pharmaceutical compositions of the invention may also be administered with a needleless hypodermic injection device; such as the devices disclosed in U.S. Pat. No. 6,620,135; 6,096,002; 5,399,163; 5,383,851; 5,312,335; 5,064,413; 4,941,880; 4,790,824 or 4,596,556.

Examples of well-known implants and modules form administering pharmaceutical compositions include: U.S. Pat. No. 4,487,603, which discloses an implantable microinfusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art.

"Treat" or "treating" means to administer a therapeutic agent, such as a composition containing any of the binding compounds of the present invention, internally or externally to a patient having one or more disease symptoms for which the agent has known therapeutic activity. Typically, the agent is administered in an amount effective to alleviate one or more disease symptoms in the treated patient or population, whether by inducing the regression of or inhibiting the progression of such symptom(s) by any clinically measurable degree. The amount of a therapeutic agent that is effective to alleviate any particular disease symptom (also referred to as the "therapeutically effective amount") may vary according to factors such as the disease state, age, and weight of the patient, and the ability of the drug to elicit a desired response in the patient. Whether a disease symptom has been alleviated can be assessed by any clinical measurement typically used by physicians or other skilled healthcare providers to assess the severity or progression status of that symptom. While an embodiment of the present invention (e.g., a treatment method or article of manufacture) may not be effective in alleviating the target disease symptom(s) in every patient, it should alleviate the target disease symptom(s) in a statistically significant number of patients as determined by any statistical test known in the art such as the Student's t-test, the $chi^2$-test, the U-test according to Mann and Whitney, the Kruskal-Wallis test (H-test), Jonckheere-Terpstra-test and the Wilcoxon-test.

"Treatment," as it applies to a human, veterinary, or research subject, refers to therapeutic treatment, prophylactic or preventative measures, to research and diagnostic applications. "Treatment" as it applies to a human, veterinary, or research subject, or cell, tissue, or organ, encompasses contact of a BTLA agonist or antagonist to a human or animal subject, a cell, tissue, physiological compartment, or physiological fluid. "Treatment of a cell" also encompasses situations where the BTLA agonist or antagonist contacts BTLA receptor, e.g., in the fluid phase or colloidal phase, but also situations where the agonist or antagonist does not contact the cell or the receptor.

In certain embodiments, an anti-BTLA antibody or antigen-binding fragment thereof, alone, or in combination can be used for treating or preventing any disease or condition in a subject in need of such treatment or prevention.

With respect to antagonist anti-BTLA antibodies, in certain embodiments, the condition is mediated, for example, by elevated expression or activity of BTLA, or by elevated expression of its ligand (e.g., HVEM) and may be treated or prevented by modulation of BTLA-HVEM ligand binding, activity or expression. In certain embodiments, the disease or condition is mediated by an increased level of BTLA, and/or HVEM and is treated or prevented by decreasing BTLA-HVEM ligand binding, activity, or expression. Antagonist anti-BTLA antibodies as described herein will block the activity of BTLA as a negative signaling molecule and will result in upregulating the response to tumors by T and B cells.

The term "B and T lymphocyte attenuator" and "BTLA", genes/proteins are used interchangeably, which includes variants, isoforms, homologs orthologs and paralogs. For example, antibodies specific for human BTLA may, in certain embodiments, cross-react with BTLA from species other than human. In other embodiments the antibodies specific for human BTLA may be completely specific for human BTLA and may not exhibit species or other types of cross reactivity. The term "human BTLA" unless otherwise noted, refers to a human BTLA sequence. Human BTLA sequences, unless otherwise noted, encompass all human isotypes and BTLA variants, such as the complete amino acid sequence of human BTLA that has Genbank Accession No. AAP44003. There are also at least two human BTLA transcript variants. Transcript variant 1 described at GenBank Accession No. NP_861445 is 289 amino acids in length and exhibits nearly 98% identity with the BTLA sequence of Accession No. AAP44003. This variant represents the longer transcript and encodes the longer isoform of 289 amino acids. Transcript variant 2 (GenBank Accession No. NM_001085357) lacks an alternate in-frame exon, compared to variant 1, resulting in a shorter protein of 241 amino acids (isoform 2, GenBank Accession No. NP_001078826), compared to isoform 1.

The human BTLA sequences may differ by having, for example, conserved mutations or mutations in non-conserved regions and the BTLA has substantially the same biological function as the human BTLA of SEQ ID NO:2, SEQ ID NO:35, or SEQ ID NO:37. For example, a biological function of human BTLA is to suppress an immune response, such as a T-cell response. That is, BTLA is considered to be a negative regulator. It has C-terminal inhibitor motifs that are involved in reducing IL-2 production and T cell expansion (Watanabe et al., Nat. Immunol., 4, 670-679, 2003; Chemnitz et al., J. Immunol., 176, 6603-6614, 2006). In addition, a biological function of human BTLA may be having, for example, an epitope in the extracellular domain of BTLA that is specifically bound by an antibody of the instant disclosure.

A particular BTLA sequence will generally be at least 90% identical in amino acid sequence to human BTLA of SEQ ID NO:2, SEQ ID NO:35, or SEQ ID NO:37, or other isoforms, and contain amino acid residues that identify the amino acid sequence as being human when compared to BTLA amino acid sequences of other species (e.g., murine). In certain cases, a human BTLA may be at least 95%, or even at least 96%, 97%, 98% or 99% identical to human BTLA of SEQ ID NO:2, SEQ ID NO:35, or SEQ ID NO:37, or other isoforms or variants. In certain embodiments, a human BTLA sequence will display no more than 10 amino acid differences from the BTLA of SEQ ID NO:2, SEQ ID NO:35, or SEQ ID NO:37, or other isoforms or variants. In certain embodiments, the human BTLA may display no more than 5, or even no more than 4, 3, 2, or 1 amino acid difference from the BTLA of SEQ ID NO:2, SEQ ID NO:35, or SEQ ID NO:37, or other isoforms or variants. Percent identity can be determined as described herein. The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

In certain instances it is useful to conduct corollary studies on mouse analog antibodies. Suitable methods as described herein can be used to generate anti-BTLA mouse antibodies as well as to select and characterize mouse anti-BTLA antibodies. While any mouse BTLA peptide with desired features and activities can be used to generate mouse BTLA antibodies, the sequences described by Watanabe et al. Nat. Immunol. 4 (7), 670-679 (2003) including GenBank Accession No. AAP44002 (306 amino acids) coded for by GenBank Accession No. AY293285 are preferred.

Additionally, a number of mouse BTLA splice variants have been characterized, and in certain instances, any of these can be utilized for generating anti-mouse BTLA antibodies. Mouse BTLA splice variants include the coding sequence NM_001037719 and corresponding amino acid sequence NP_001032808 for the longer transcript variant 1 (306 amino acids in length) and the shorter transcript 2 variant sequence is described at GenBank NP_808252 (305 amino acids in length); which uses an alternate in-frame splice site in the 3' coding region, compared to variant 1, resulting in a shorter protein (isoform 2).

As used herein, the term "antibody" refers to any form of antibody that exhibits the desired biological activity. Thus, it is used in the broadest sense and specifically covers, but is not limited to, monoclonal antibodies (including full length monoclonal antibodies), polyclonal antibodies, multispecific antibodies (e.g., bispecific antibodies), humanized, fully human antibodies, chimeric antibodies and camelized single domain antibodies. As used herein, the terms "anti BTLA antibody" or "antigen binding fragment" of an antibody (the "parental antibody") encompass a fragment or a derivative of an antibody, typically including at least a fragment of the antigen binding or variable regions (e.g. one or more CDRs) of the parental antibody, that retains at least some of the binding specificity of the parental antibody. Examples of antibody binding fragments include, but are not limited to, Fab, Fab', F(ab')$_2$, and Fv fragments; diabodies; linear antibodies; single-chain antibody molecules, e.g., sc-Fv; nanobodies and multispecific antibodies formed from antibody fragments. Typically, a binding fragment or derivative retains at least 10% of its BTLA binding activity when that activity is expressed on a molar basis. Preferably, a binding fragment or derivative retains at least 20%, 50%, 70%, 80%, 90%, 95% or 100% or more of the BTLA binding affinity as the parental antibody. It is also intended that an anti BTLA antigen binding fragment can include conservative or non conservative amino acid substitutions (referred to as "conservative variants" or "function conserved variants" of the antibody) that do not substantially alter its biologic activity. The term "binding compound" refers to both antibodies and binding fragments thereof.

"Isolated antibody" refers to the purification status of a binding compound and in such context means the molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

A "Fab fragment" is comprised of one light chain and the $C_H1$ and variable regions of one heavy chain. The heavy chain of a Fab molecule cannot form a disulfide bond with another heavy chain molecule.

An "Fc" region contains two heavy chain fragments comprising the $C_H1$ and $C_H2$ domains of an antibody. The two heavy chain fragments are held together by two or more disulfide bonds and by hydrophobic interactions of the $C_H3$ domains.

A "Fab' fragment" contains one light chain and a portion or fragment of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')$_2$ molecule.

A "F(ab')$_2$ fragment" contains two light chains and two heavy chains containing a portion of the constant region between the $C_H1$ and $C_H^2$ domains, such that an interchain disulfide bond is formed between the two heavy chains. A F(ab')$_2$ fragment thus is composed of two Fab' fragments that are held together by a disulfide bond between the two heavy chains.

The "Fv region" comprises the variable regions from both the heavy and light chains, but lacks the constant regions.

The term "single-chain Fv" or "scFv" antibody refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv, see Pluckthun (1994) THE PHARMACOLOGY OF MONOCLONAL ANTIBODIES, vol. 113, Rosenburg and Moore eds. Springer-Verlag, New York, pp. 269-315. See also, International Patent Application Publication No. WO 88/01649 and U.S. Pat. Nos. 4,946,778 and 5,260,203.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen binding sites. In some instances, the two binding sites have the same antigen specificities. However, bivalent antibodies may be bispecific (see below).

As used herein, unless otherwise indicated, an "anti-BTLA" antibody refers to an antibody that is raised against human BTLA or a variant thereof, or any antigenic fragment thereof.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352: 624-628 and Marks et al. (1991) *J. Mol. Biol.* 222: 581-597, for example. See also Presta (2005) *J. Allergy Clin. Immunol.* 116:731.

In certain embodiments, monoclonal antibodies include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., (1984) *Proc. Natl. Acad. Sci. USA* 81: 6851-6855).

As used herein, a "chimeric antibody" is an antibody having the variable domain from a first antibody and constant domain from a second antibody, where the first and second antibodies are from different species. Typically the variable domains are obtained from an antibody from an experimental animal (the "parental antibody"), such as a rodent, and the constant domain sequences are obtained from human antibodies, so that the resulting chimeric antibody will be less likely to elicit an adverse immune response in a human subject than the parental rodent antibody.

In certain embodiments, monoclonal antibodies herein also include camelized single domain antibodies. See, e.g., Muyldermans et al. (2001) *Trends Biochem. Sci.* 26:230; Reichmann et al. (1999) *J. Immunol. Methods* 231:25; WO 94/04678; WO 94/25591; U.S. Pat. No. 6,005,079). In one embodiment, the present invention provides single domain antibodies comprising two $V_H$ domains with modifications such that single domain antibodies are formed.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) *Proc. Natl. Acad. Sci. USA* 90: 6444-6448. For a review of engineered antibody variants generally see Holliger and Hudson (2005) *Nat. Biotechnol.* 23:1126-1136.

As used herein, the term "humanized antibody" refers to forms of antibodies that contain sequences from both human and non-human (e.g., murine, rat) antibodies. In general, the humanized antibody will comprise substantially all of at least one, and typically two, variable domains, in which all or substantially all of the hypervariable loops correspond to those of a non-human immunoglobulin, and all or substantially all of the framework (FR) regions are those of a human immunoglobulin sequence. The humanized antibody may optionally comprise at least a portion of a human immunoglobulin constant region (Fc).

The antibodies of the present invention also include antibodies with modified (or blocked) Fc regions to provide altered effector functions. See, e.g., U.S. Pat. No. 5,624,821; WO2003/086310; WO2005/120571; WO2006/0057702. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antibodies, enabling less frequent dosing and thus increased convenience and decreased use of material. See Presta (2005) *J. Allergy Clin. Immunol.* 116:731 at 734-35.

The term "fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" refers to an antibody that comprises mouse immunoglobulin sequences only. Alternatively, a fully human antibody may contain rat carbohydrate chains if produced in a rat, in a rat cell, or in a hybridoma derived from a rat cell. Similarly, "rat antibody" refers to an antibody that comprises rat immunoglobulin sequences only.

Antibody Structure

In general, the basic antibody structural unit is known to comprise a tetramer. Each tetramer includes two identical pairs of polypeptide chains, each pair having one "light" (about 25 kDa) and one "heavy" chain (about 50-70 kDa). The amino-terminal portion or fragment of each chain may include a variable region of about 100 to 110 or more amino acids primarily responsible for antigen recognition. The carboxy-terminal portion or fragment of each chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989).

The variable regions of each light/heavy chain pair to form the antibody binding site. Thus, in general, an intact IgG antibody has two binding sites. Except in bifunctional or bispecific antibodies, the two binding sites are, in general, the same.

Normally, the chains all exhibit the same general structure of relatively conserved framework regions (FR) joined by three hypervariable regions, also called complementarity determining regions or CDRs. The CDRs from the two chains of each pair are usually aligned by the framework regions, enabling binding to a specific epitope. In general, from N-terminal to C-terminal, both light and heavy chains comprise the domains FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; 5$^{th}$ ed.; NIH Publ. No. 91-3242 (1991); Kabat (1978) Adv. Prot. Chem. 32:1-75; Kabat, et al., (1977) J. Biol. Chem. 252:6609-6616; Chothia, et al., (1987) J Mol. Biol. 196:901-917 or Chothia, et al., (1989) Nature 342:878-883.

As used herein, the term "hypervariable region" refers to the amino acid residues of an antibody which are responsible for antigen-binding. The hypervariable region comprises amino acid residues from a "complementarity determining region" or "CDR" (i.e. residues 24-34 (CDRL1), 50-56 (CDRL2) and 89-97 (CDRL3) in the light chain variable domain and residues 31-35 (CDRH1), 50-65 (CDRH2) and 95-102 (CDRH3) in the heavy chain variable domain; Kabat et al. (1991) Sequences of Proteins of Immunological Interest, 5th Ed. Public Health Service, National Institutes of Health, Bethesda, Md.) and/or those residues from a "hypervariable loop" (i.e. residues 26-32 (CDRL1), 50-52 (CDRL2) and 91-96 (CDRL3) in the light chain variable domain and 26-32 (CDRH1), 53-55 (CDRH2) and 96-101 (CDRH3) in the heavy chain variable domain; Chothia and Lesk (1987) *J. Mol. Biol.* 196: 901-917). As used herein, the term "framework" or "FR" residues refers to those variable domain residues other than the hypervariable region residues defined herein as CDR residues.

"Binding substance" refers to a molecule, small molecule, macromolecule, antibody, a fragment or analogue thereof, or soluble receptor, capable of binding to a target. "Binding substance" also may refer to a complex of molecules, e.g., a non-covalent complex, to an ionized molecule, and to a covalently or non-covalently modified molecule, e.g., modified by phosphorylation, acylation, cross-linking, cyclization, or limited cleavage, that is capable of binding to a target. "Binding substance" may also refer to a molecule capable of binding to a target in combination with a stabilizer, excipient, salt, buffer, solvent, or additive. "Binding" may be defined as an association of the binding substance with a target where the association results in reduction in the normal Brownian motion of the binding substance, in cases where the binding substance can be dissolved or suspended in solution.

"Effective amount" encompasses an amount sufficient to ameliorate or prevent a symptom or sign of the medical condition. Effective amount also means an amount sufficient to allow or facilitate diagnosis. An effective amount for a particular patient or veterinary subject may vary depending on factors such as the condition being treated, the overall health of the patient, the method route and dose of administration and the severity of side affects (see, e.g., U.S. Pat. No. 5,888, 530 issued to Netti, et al.). An effective amount can be the maximal dose or dosing protocol that avoids significant side effects or toxic effects. The effect will result in an improvement of a diagnostic measure or parameter by at least 5%, usually by at least 10%, more usually at least 20%, most usually at least 30%, preferably at least 40%, more preferably at least 50%, most preferably at least 60%, ideally at least 70%, more ideally at least 80%, and most ideally at least 90%, where 100% is defined as the diagnostic parameter shown by a normal subject (see, e.g., Maynard, et al. (1996) *A Handbook of SOPs for Good Clinical Practice*, Interpharm Press, Boca Raton, Fla.; Dent (2001) *Good Laboratory and Good Clinical Practice*, Urch Publ., London, UK).

"Exogenous" refers to substances that are produced outside an organism, cell, or human body, depending on the context. "Endogenous" refers to substances that are produced within a cell, organism, or human body, depending on the context.

"Homology" refers to sequence similarity between two polynucleotide sequences or between two polypeptide sequences. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous when the sequences are optimally aligned then the two sequences are 60% homologous. Generally, the comparison is made when two sequences are aligned to give maximum percent homology.

"Immune condition" or "immune disorder" encompasses, e.g., pathological inflammation, an inflammatory disorder, and an autoimmune disorder or disease. "Immune condition" also refers to infections, persistent infections, and proliferative conditions, such as cancer, tumors, and angiogenesis, including infections, tumors, and cancers that resist eradication by the immune system. "Cancerous condition" includes, e.g., cancer, cancer cells, tumors, angiogenesis, and precancerous conditions such as dysplasia.

"Inflammatory disorder" means a disorder or pathological condition where the pathology results, in whole or in part, from, e.g., a change in number, change in rate of migration, or change in activation, of cells of the immune system. Cells of the immune system include, e.g., T cells, B cells, monocytes or macrophages, antigen presenting cells (APCs), dendritic cells, microglia, NK cells, NKT cells, neutrophils, eosinophils, mast cells, or any other cell specifically associated with the immunology, for example, cytokine-producing endothelial or epithelial cells.

"Isolated binding compound" refers to the purification status of a binding compound and in such context means the molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

"Isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, "polymerase chain reaction" or "PCR" refers to a procedure or technique in which minute amounts of a specific piece of nucleic acid, RNA and/or DNA, are amplified as described in, e.g., U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al. (1987) *Cold Spring Harbor Symp. Quant. Biol.* 51:263; Erlich, ed., (1989) PCR TECHNOLOGY (Stockton Press, N.Y.) As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

As used herein, the term "germline sequence" refers to a sequence of unrearranged immunoglobulin DNA sequences. Any suitable source of unrearranged immunoglobulin may be used.

"Inhibitors" and "antagonists," or "activators" and "agonists," refer to inhibitory or activating molecules, respectively, e.g., for the activation of, e.g., a ligand, receptor, cofactor, a gene, cell, tissue, or organ. A modulator of, e.g., a gene, a receptor, a ligand, or a cell, is a molecule that alters an activity of the gene, receptor, ligand, or cell, where activity can be activated, inhibited, or altered in its regulatory properties. The modulator may act alone, or it may use a cofactor, e.g., a protein, metal ion, or small molecule. Inhibitors are compounds that decrease, block, prevent, delay activation, inactivate, desensitize, or down regulate, e.g., a gene, protein, ligand, receptor, or cell. Activators are compounds that increase, activate, facilitate, enhance activation, sensitize, or up regulate, e.g., a gene, protein, ligand, receptor, or cell. An inhibitor may also be defined as a compound that reduces, blocks, or inactivates a constitutive activity. An "agonist" is a compound that interacts with a target to cause or promote an increase in the activation of the target. An "antagonist" is a compound that opposes the actions of an agonist. An antagonist prevents, reduces, inhibits, or neutralizes the activity of an agonist. An antagonist can also prevent, inhibit, or reduce constitutive activity of a target, e.g., a target receptor, even where there is no identified agonist. In the case of BTLA, a BTLA agonist would initiate and potentiate the negative signal delivered by BTLA to B and T cells. On the other hand, a BTLA antagonist would block that signal to B and T cells, thus augmenting B and T cell activation/proliferation.

To examine the extent of inhibition, for example, samples or assays comprising a given, e.g., protein, gene, cell, or organism, are treated with a potential activator or inhibitor and are compared to control samples without the inhibitor. Control samples, i.e., samples not treated with antagonist, are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 25%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Endpoints in activation or inhibition can be monitored as follows. Activation, inhibition, and response to treatment, e.g., of a cell, physiological fluid, tissue, organ, and animal or human subject, can be monitored by an endpoint. The endpoint may comprise a predetermined quantity or percentage of, e.g., indicia of inflammation, oncogenicity, or cell degranulation or secretion, such as the release of a cytokine, toxic oxygen, or a protease. The endpoint may comprise, e.g., a predetermined quantity of ion flux or transport; cell migration; cell adhesion; cell proliferation; potential for metastasis; cell differentiation; and change in phenotype, e.g., change in expression of gene relating to inflammation, apoptosis, transformation, cell cycle, or metastasis (see, e.g., Knight (2000) *Ann. Clin. Lab. Sci.* 30:145-158; Hood and Cheresh (2002) *Nature Rev. Cancer* 2:91-100; Timme, et al. (2003) *Curr. Drug Targets* 4:251-261; Robbins and Itzkowitz (2002) *Med. Clin. North Am.* 86:1467-1495; Grady and Markowitz (2002) *Annu. Rev. Genomics Hum. Genet.* 3:101-128; Bauer, et al. (2001) *Glia* 36:235-243; Stanimirovic and Satoh (2000) *Brain Pathol.* 10:113-126).

An endpoint of inhibition is generally 75% of the control or less, preferably 50% of the control or less, more preferably 25% of the control or less, and most preferably 10% of the control or less. Generally, an endpoint of activation is at least 150% the control, preferably at least two times the control, more preferably at least four times the control, and most preferably at least ten times the control.

"Ligand" refers, e.g., to a small molecule, peptide, polypeptide, and membrane associated or membrane-bound molecule, or complex thereof, that can act as an agonist or antagonist of a receptor. "Ligand" also encompasses an agent that is not an agonist or antagonist, but that can bind to the receptor. Moreover, "ligand" includes a membrane-bound ligand that has been changed, e.g., by chemical or recombinant methods, to a soluble version of the membrane-bound ligand. By convention, where a ligand is membrane-bound on a first cell, the receptor usually occurs on a second cell. The second cell may have the same or a different identity as the first cell. A ligand or receptor may be entirely intracellular, that is, it may reside in the cytosol, nucleus, or some other intracellular compartment. The ligand or receptor may change its location, e.g., from an intracellular compartment to the outer face of the plasma membrane. The complex of a ligand and receptor is termed a "ligand receptor complex." Where a ligand and receptor are involved in a signaling pathway, the ligand occurs at an upstream position and the receptor occurs at a downstream position of the signaling pathway. HVEM is a TNF-receptor superfamily member. In addition to binding BTLA, it also can bind LIGHT, LTα and CD160.

"Small molecule" is defined as a molecule with a molecular weight that is less than 10 kDa, typically less than 2 kDa, preferably less than 1 kDa, and most preferably less than about 500 Da. Small molecules include, but are not limited to, inorganic molecules, organic molecules, organic molecules containing an inorganic component, molecules comprising a radioactive atom, synthetic molecules, peptide mimetics, and antibody mimetics. As a therapeutic, a small molecule may be more permeable to cells, less susceptible to degradation, and less apt to elicit an immune response than large molecules. Small molecules, such as peptide mimetics of antibodies and cytokines, as well as small molecule toxins, have been described (see, e.g., Casset, et al. (2003) *Biochem. Biophys. Res. Commun.* 307:198-205; Muyldermans (2001) *J. Biotechnol.* 74:277-302; L1 (2000) *Nat. Biotechnol.* 18:1251-1256; Apostolopoulos, et al. (2002) *Curr. Med. Chem.* 9:411-420; Monfardini, et al. (2002) *Curr. Pharm. Des.* 8:2185-2199; Domingues, et al. (1999) *Nat. Struct. Biol.* 6:652-656; Sato and Sone (2003) *Biochem. J.* 371:603-608; U.S. Pat. No. 6,326,482 issued to Stewart, et al).

"Specifically" or "selectively" binds, when referring to a ligand/receptor, antibody/antigen, or other binding pair, indicates a binding reaction that is determinative of the presence of the protein in a heterogeneous population of proteins and other biologics. Thus, under designated conditions, a specified ligand binds to a particular receptor and does not bind in a significant amount to other proteins present in the sample. The antibody, or binding compound derived from the antigen-binding site of an antibody, of the contemplated method binds to its antigen, or a variant or mutein thereof, with an affinity that is at least two fold greater, preferably at least ten times greater, more preferably at least 20-times greater, and most preferably at least 100-times greater than the affinity with any other antigen.

As used herein, the term "immunomodulatory agent" refers to natural or synthetic agents that suppress or modulate an immune response. The immune response can be a humoral or cellular response. Immunomodulatory agents encompass immunosuppressive or anti-inflammatory agents.

"Immunosuppressive agents", "immunosuppressive drugs", or "immunosuppressants" as used herein are therapeutics that are used in immunosuppressive therapy to inhibit or prevent activity of the immune system. Clinically they are used to prevent the rejection of transplanted organs and tissues (e.g. bone marrow, heart, kidney, liver), and/or in the treatment of autoimmune diseases or diseases that are most likely of autoimmune origin (e.g. rheumatoid arthritis, myasthenia gravis, systemic lupus erythematosus, ulcerative colitis, multiple sclerosis). Immunosuppressive drugs can be classified as: glucocorticoids; cytostatics; antibodies; biological response modifiers such as Ig fusion proteins including CTLA-4/Ig (Abatacept™); drugs acting on immunophilins; other drugs, including known chemotherapeutic agents used in the treatment of proliferative disorders, such as mycophenolatemofetil (MMF). For multiple sclerosis, in particular, the antibodies of the present invention can be administered in conjunction with a new class of myelin binding protein-like therapeutics, known as copaxones.

"Anti-inflammatory agents" or "anti-inflammatory drugs" refer to both steroidal and non-steroidal therapeutics. Steroids, also known as corticosteroids, are drugs that closely resemble cortisol, a hormone produced naturally by adrenal glands. Steroids are used as the main treatment for certain inflammatory conditions, such as: systemic vasculitis (inflammation of blood vessels); and myositis (inflammation of muscle). Steroids might also be used selectively to treat inflammatory conditions such as: rheumatoid arthritis (chronic inflammatory arthritis occurring in joints on both sides of the body); systemic lupus erythematosus (a generalized disease caused by abnormal immune system function); Sjögren's syndrome (chronic disorder that causes dry eyes and a dry mouth).

Non-steroidal anti-inflammatory drugs, usually abbreviated to NSAIDs, are drugs with analgesic, antipyretic and anti-inflammatory effects—they reduce pain, fever and inflammation. The term "non-steroidal" is used to distinguish these drugs from steroids, which (amongst a broad range of other effects) have a similar eicosanoid-depressing, anti-inflammatory action. NSAIDs are generally indicated for the symptomatic relief of the following conditions: rheumatoid arthritis; osteoarthritis; inflammatory arthropathies (e.g. ankylosing spondylitis, psoriatic arthritis, Reiter's syndrome); acute gout; dysmenorrhoea; metastatic bone pain; headache and migraine; postoperative pain; mild-to-moderate pain due to inflammation and tissue injury; pyrexia; and renal colic. NSAIDs include salicylates, arlyalknoic acids, 2-arylpropionic acids (profens), N-arylanthranilic acids (fenamic acids), oxicams, coxibs, and sulphonanilides.

Disease-modifying anti-rheumatic drugs (DMARDs) may be administered, often in combination with NSAIDs. Commonly prescribed DMARDs include hydroxychloroquine/chloroquine, methotrexate, gold therapy, sulfasalazine, and azathioprine.

A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell. An example of a "cell surface receptor" of the present disclosure is the BTLA receptor.

Antibodies Specific for Human BTLA

The present invention generally isolated antibodies or antigen binding fragments thereof that bind BTLA and uses of such antibodies or antigen binding fragments thereof. More specifically, the invention provides isolated fully human anti BTLA antibodies and methods of use of the antibodies or antigen binding fragments thereof in the treatment of disease. Examples of fully human anti-BTLA antibodies include, but are not limited to: Hu Mab8D5, hu Mab8A3, hu Mab21H6, hu Mab19A7, and hu Mab4C7.

The present invention provides an isolated anti-BTLA agonist antibody or antigen binding fragment thereof wherein the antibody or antigen binding fragment exhibits one or more of the following properties: (1) does not block binding of HVEM or LIGHT to human BTLA; (2) cross reacts with cynomolgus BTLA; (3) has a $K_D$ for binding to human BTLA of at most about $2.5 \times 10^{-9}$ in a protein binding assay (e.g., Biacore); and (4) an $EC_{50}$ of at least about 10 nM in a T and B cell activation assay. In one embodiment anti-BTLA antibody or antigen binding fragment thereof has a $K_D$ for binding to human BTLA of at most about $2.5 \times 10^{-9}$ in a protein binding assay (e.g., Biacore; Examples 2-3) and an $EC_{50}$ of about 10-100 nM in a T and B cell activation assay.

In another embodiment, the antibody or antigen binding fragment is an isolated fully human antibody or antigen binding fragment thereof which blocks binding of HVEM to BTLA. In yet another embodiment, Examples of such antibodies include, but are not limited to, the fully human anti-BTLA antibody, hu Mab4C7.

The isolated antibody or antigen binding fragment thereof, that binds BTLA can comprise one, two, three, four, five, or six complementarity determining regions (CDRs) of the described antibodies and antigen-binding fragments of the invention. The one, two, three, four, five, or six CDRs may be independently selected from the described CDR sequences (e.g., Table 1, Table 2) of the antibodies and antigen-binding fragments of the invention. Alternatively, the one, two, three, four, five, or six CDRs may be selected from the CDR sequences of a single described antibody or antigen-binding fragment of the invention. In certain embodiments, one two or three CDRs are selected from the $V_L$ CDRs (e.g., Table 1; SEQ ID NOs:12-14) of the described agonist antibodies and/or one, two or three CDRs selected from the $V_H$ CDRs (e.g., Table 2; SEQ ID NOs:5-7) of the described invention. In another embodiment, one two or three CDRs are selected from the $V_L$ CDRs (e.g., Table 1; SEQ ID NOs:26-28) of the described antagonist antibodies and/or one, two or three CDRs selected from the $V_H$ CDRs (e.g., Table 2; SEQ ID NOs:19-21) of the described invention.

The isolated antibody or antigen-binding fragment thereof that binds BTLA can comprise at least one antibody light chain variable ($V_L$) domain comprising one or more of CDR-L1, CDR-L2 or CDR-L3 selected from the group consisting of: (a) CDR-L1, CDR-L2 and CDR-L3 of the variable region of antibody hu Mab8D5; (b) CDR-L1, CDR-L2 and CDR-L3 of the variable region of antibody hu Mab8A3; (c) CDR-L1, CDR-L2 and CDR-L3 of the variable region of antibody hu Mab21H6; and (d) CDR-L1, CDR-L2 and CDR-L3 of the variable region of antibody hu Mab19A7.

The isolated antibody or antigen-binding fragment thereof that binds BTLA can comprise at least one antibody heavy chain variable (VH) domain comprising one or more of CDR-H1, CDR-H2 or CDR-H3 selected from the group consisting of: (a) CDR-H1, CDR-H2 and CDR-H3 of the variable region of antibody hu Mab8D5; (b) CDR-H1, CDR-H2 and CDR-H3 of the variable region of antibody hu Mab8A3; (c) CDR-H1, CDR-H2 and CDR-H3 of the variable region of antibody hu Mab21H6; and (d) CDR-H1, CDR-H2 and CDR-H3 of the variable region of antibody hu Mab19A7.

In a preferred embodiment the isolated antibody or antigen-binding fragment thereof that binds BTLA comprises at least one antibody light chain variable ($V_L$) domain comprising a CDR-L1, CDR-L2 and CDR-L3 selected from the group consisting of: (a) CDR-L1, CDR-L2 and CDR-L3 of the variable region of antibody hu Mab8D5; (b) CDR-L1, CDR-L2 and CDR-L3 of the variable region of antibody hu Mab8A3; (c) CDR-L1, CDR-L2 and CDR-L3 of the variable region of antibody hu Mab21H6; and (d) CDR-L1, CDR-L2 and CDR-L3 of the variable region of antibody hu Mab19A7 and at least one antibody heavy chain variable ($V_H$) domain comprising a CDR-H1, CDR-H2 and CDR-H3 selected from the group consisting of: (a) CDR-H1, CDR-H2 and CDR-H3 of the variable region of antibody hu Mab8D5; (b) CDR-H1, CDR-H2 and CDR-H3 of the variable region of antibody hu Mab8A3; (c) CDR-H1, CDR-H2 and CDR-H3 of the variable region of antibody hu Mab21H6; and (d) CDR-H1, CDR-H2 and CDR-H3 of the variable region of antibody hu Mab19A7.

Sequences of light and heavy chain CDRs of the antibodies of the present invention are provided in Tables 1 and 2, respectively. By way of example and not limitation, the $V_L$ domain CDRs for agonist antibodies are selected from SEQ ID NOs: 12-14, while $V_L$ domain CDRs for antagonist antibodies are selected from SEQ ID NOs:26-28. Similarly, $V_H$ domain CDRs for agonist antibodies are selected from SEQ ID NOs: 7-9, while $V_H$ domain CDRs for antagonist antibodies are selected from SEQ ID NOs: 10-12.

TABLE 1

Light Chain CDRs

| Antibody | CDR1 | CDR2 | CDR3 |
| --- | --- | --- | --- |
| 8D5 (agonist) | (SEQ ID NO: 12) | (SEQ ID NO: 13) | (SEQ ID NO: 14) |
| 4C7 (antagonist) | (SEQ ID NO: 26, $V_K$) | (SEQ ID NO: 27, $V_K$) | (SEQ ID NO: 28, $V_K$) |

TABLE 2

Heavy Chain CDRs

| Antibody | CDR1 | CDR2 | CDR3 |
| --- | --- | --- | --- |
| 8D5 (agonist) | (SEQ ID NO: 5) | (SEQ ID NO: 6) | (SEQ ID NO: 7) |
| 4C7 (antagonist) | (SEQ ID NO: 19) | (SEQ ID NO: 20) | (SEQ ID NO: 21) |

The present invention further provides an isolated antibody or antigen binding fragment thereof that binds BTLA and functions as an agonist antibody and comprises the mature $V_L$ domain of antibody Hu Mab8D5 (SEQ ID No:18). In a preferred embodiment, the antibody is a fully human monoclonal antibody. Examples of preferred fully human agonist anti-BTLA antibodies include, but are not limited to hu Mab8D5, hu Mab8A3, hu Mab21H6, hu Mab19A7, and antigen binding fragments thereof.

The present invention further provides an isolated antibody or antigen binding fragment thereof that binds BTLA and functions as an antagonist and comprises the mature $V_L$ domain of antibody Hu Mab4C7 (SEQ ID No:32). In a preferred embodiment, the antibody is a fully human monoclonal antibody. An example of a preferred fully human antagonist anti-BTLA antibody includes, but is not limited to hu Mab4C7 and antigen binding fragments thereof.

The present invention further provides an isolated antibody or antigen binding fragment thereof that binds BTLA and functions as an agonist and comprises at least one $V_H$ domain selected from the group consisting of (a) the mature $V_H$ domain of antibody Hu Mab8D5 (SEQ ID No:11). In a preferred embodiment the antibody is a fully human monoclonal agonist anti-BTLA antibody. Examples of preferred fully human agonist anti-BTLA antibodies include, but are not limited to hu Mab8D5, hu Mab8A3, hu Mab21H6, hu Mab19A7, and antigen binding fragments thereof.

The present invention further provides an isolated antibody or antigen binding fragment thereof that binds BTLA and functions as an antagonist and comprises at least one $V_H$ domain selected from the group consisting of (a) the mature $V_H$ domain of antibody hu Mab4C7 (SEQ ID No:25). In a preferred embodiment the antibody is a fully human antagonist anti-BTLA antibody. An example of a preferred fully human antagonist anti-BTLA antibody includes, but is not limited to hu Mab4C7 and antigen binding fragments thereof.

The present invention provides an isolated agonist antibody or antigen binding fragment thereof that binds BTLA and has at least one $V_L$ domain selected from the group consisting of SEQ ID Nos.:12, 13, and 14 and at least one $V_H$ domain selected from the group consisting of SEQ ID Nos.: 5, 6, and 7. In a preferred embodiment the antibody is a fully human agonist anti-BTLA antibody. Examples of preferred fully human agonist anti-BTLA antibodies include, but are not limited to hu Mab8D5, hu Mab8A3, hu Mab21H6, hu Mab19A7, and antigen binding fragments thereof.

The present invention provides an isolated antagonist antibody or antigen binding fragment thereof that binds BTLA and has at least one $V_L$ domain selected from the group consisting of SEQ ID Nos.:26, 27, 28, and at least one $V_H$ domain selected from the group consisting of SEQ ID Nos.: 19, 20, and 21. In a preferred embodiment the antibody is a fully human antagonist anti-BTLA antibody. Examples of preferred fully human antagonist anti-BTLA antibodies include, but are not limited to, hu Mab4C7 and antigen binding fragments thereof.

In one embodiment, the isolated antibody of the present invention comprises a heavy chain constant region, preferably a human constant region, such as γ1, γ2, γ3, or γ4 human heavy chain constant region or a variant thereof. In another embodiment, the binding compound comprises a light chain constant region, preferably a human light chain constant region, such as lambda or kappa human light chain region or variant thereof. By way of example, and not limitation the human heavy chain constant region can be γ1 and the human light chain constant region can be kappa. In an alternative embodiment, the Fc region of the antibody is γ4 with a Ser228Pro mutation (Schuurman, J et. al., *Mol. Immunol.* 38: 1-8, 2001).

In one embodiment, the antigen binding fragment is selected from the group consisting of Fab, Fab', Fab'-SH, Fv, scFv, F(ab')₂, and a diabody.

The invention also provides isolated polypeptides comprising the $V_L$ domains (e.g., SEQ ID Nos.:16, 18, 30, 32, 37, and 38) and isolated polypeptides comprising the $V_H$ domains (e.g., SEQ ID Nos.:9, 11, 23, and 25) of the antibodies of the invention. In one embodiment the invention provides an antibody or antigen binding fragment thereof that binds BTLA and has $V_L$ domains $V_H$ domains with at least 95%, 90%, 85%, 80%, 75% or 50% sequence homology. In another embodiment the binding compound of the present invention comprises $V_L$ and $V_H$ domains (with and without signal sequence) having up to 0, 1, 2, 3, 4, 5, 6, 7, 8, 9, 10 or more conservative or non conservative amino acid substitutions, while still exhibiting the desired binding property.

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Various embodiments of the binding compounds of the present invention comprise polypeptide chains with sequences that include up to 0 (no changes), 1, 2, 3, 4, 5, 6, 7, 8, 9, 10, 12, 15, 20 or more conservative amino acid substitutions when compared with the specific amino acid sequences disclosed herein, e.g. SEQ ID NOs: 5, 6, 7, 9, 11, 12, 13, 14, 16, 18, 19, 20, 21, 23, 25, 30, 32, and 37. As used herein, the phrase "up to X" conservative amino acid substitutions includes 0 substitutions and any number of substitutions up to and including X substitutions. Such exemplary substitutions are preferably made in accordance with those set forth in Table 3 as follows:

TABLE 3

Exemplary Conservative Amino Acid Substitutions

| Original residue | Conservative substitution |
|---|---|
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

Function-conservative variants of the antibodies of the invention are also contemplated by the present invention. "Function-conservative variants" are those in which one or more amino acid residues in a protein or enzyme have been changed without altering the overall conformation and function of the polypeptide, including, but, by no means, limited to, replacement of an amino acid with one having similar properties.

Amino Acid Substitutions

The invention also provides isolated polypeptides comprising the $V_L$ domains of agonist BTLA antibodies (e.g., SEQ ID Nos.:16 and 18) and isolated polypeptides comprising the $V_H$ domains (e.g., SEQ ID Nos.: 9 and 11) of agonist BTLA antibodies of the invention having up to 0, 1, 2, 3, 4, or 5 or more amino acid substitutions, while still exhibiting the ability to bind to BTLA.

In additional embodiments, the invention provides isolated polypeptides comprising the $V_L$ domains of antagonist BTLA antibodies (e.g., SEQ ID Nos.: 30 or 32) and isolated polypeptides comprising the $V_H$ domains (e.g., SEQ ID Nos.: 23 or 25) of antagonist BTLA antibodies of the invention having up to 0, 1, 2, 3, 4, or 5 or more amino acid substitutions, while still exhibiting the ability to bind to BTLA.

In another embodiment, the invention provides an antibody or antigen binding fragment thereof that binds human BTLA and has $V_L$ domains $V_H$ domains with at least 95%, 90%, 85%, 80%, 75% or 50% sequence homology to one or more of the $V_L$ domains or $V_H$ domains described herein, and exhibits binding to human BTLA. In another embodiment the binding compound of the present invention comprises $V_L$ and $V_H$ domains (with and without signal sequence) having up to 0, 1, 2, 3, 4, or 5 or more amino acid substitutions, and exhibits binding to human BTLA.

In certain embodiments, it will be desirable to change certain amino acids containing exposed side-chains to another amino acid residue in order to provide for greater chemical stability of the final antibody, as follows. For example, an asparagine (Asn) residue may be changed to Gln or Ala to reduce the potential for formation of isoaspartate at any Asn-Gly sequences within a CDR. A similar problem may occur at a Asp-Gly sequence. See, Reissner and Aswad (2003) *Cell. Mol. Life Sci.* 60:1281. Isoaspartate formation may debilitate or completely abrogate binding of an antibody to its target antigen. See, Presta (2005) *J. Allergy Clin. Immunol.* 116:731 at 734. In one embodiment, the asparagine is changed to glutamine (Gln). It may also be desirable to alter an amino acid adjacent to an asparagine (Asn) or glutamine (Gln) residue to reduce the likelihood of deamidation, which occurs at greater rates when small amino acids occur adjacent to asparagine or glutamine. See, Bischoff & Kolbe (1994) *J. Chromatog.* 662:261. In addition, any methionine residues (typically solvent exposed Met) in CDRs may be changed to Lys, Leu, Ala, or Phe in order to reduce the possibility that the methionine sulfur would oxidize, which could reduce antigen binding affinity and also contribute to molecular heterogeneity in the final antibody preparation. Id. In one embodiment, the methionine is changed to alanine (Ala). Additionally, in order to prevent or minimize potential scissile Asn-Pro peptide bonds, it may be desirable to alter any Asn-Pro combinations found in a CDR to Gln-Pro, Ala-Pro, or Asn-Ala. Antibodies with such substitutions are subsequently screened to ensure that the substitutions do not decrease BTLA binding affinity or other desired biological activity to unacceptable levels.

TABLE 4

Exemplary stabilizing CDR variants

| CDR Residue/s→ | Stabilizing Variant Sequence |
| --- | --- |
| Asn-Gly (N-G) | Gln-Gly, Ala-Gly, or Asn-Ala (Q-G), (A-G), or (N-A) |
| Asp-Gly (D-G) | Glu-Gly, Ala-Gly or Asp-Ala (E-G), (A-G), or (D-A) |
| Met (typically solvent exposed) (M) | Lys, Leu, Ala, or Phe (K), (L), (A), or (F) |
| Asn (N) | Gln or Ala (Q) or (A) |
| Asn-Pro (N-P) | Gln-Pro, Ala-Pro, or Asn-Ala (Q-P), (A-P), or (N-A) |

Exemplary CDR Variants for 8D5 VH Include:
CDR1: SYDMH (SEQ ID NO:5)
CDR1 variant SYDXH=wherein X is M, K, L, A, or F (SEQ ID NO:38)
CDR3: EGMAAHNYYGMDV (SEQ ID NO:7)
CDR3 variant $EGX_1AAHX_2YYGX_1DV$=wherein $X_1$ is M, K, L, A, or F; $X_2$ is N, Q or A (SEQ ID NO:39)
The X variations for the VH CDRs can be independently selected in any combination.
Exemplary CDR Variants for 8D5 VL Include:
CDR2: DASNRAT (SEQ ID NO:13)
CDR2 variant: DASXRAT=wherein X is Q or A (SEQ ID NO:40)
CDR3: QQRSNWPPIT (SEQ ID NO:14)
CDR3 variant: QQRSXWPPIT=wherein X is Q or A (SEQ ID NO:41)
The X variations for the VL CDRs can be independently selected in any combination. Additionally, any X variation described herein can be independently selected in any combination, as long as the desired activity or binding ability is maintained.
Exemplary CDR Variants for 4C7 VH Include:
CDR2: YIYYSGSTKYNPSLKS (SEQ ID NO:20)
CDR2 variant: $YIYYSGSTKYX_1X_2SLKS$=wherein $X_1X_2$ are N-P, Q-P, A-P, or N-A (SEQ ID NO:42)
CDR3: EWPYYYYEMDV (SEQ ID NO:21)
CDR3 variant: EWPYYYYEXDV=wherein X is M, K, L, A, or F (SEQ ID NO:43)
The X variations for the VH CDRs can be independently selected in any combination.

The terms "consists essentially of," or variations such as "consist essentially of" or "consisting essentially of," as used throughout the specification and claims, indicate the inclusion of any recited elements or group of elements, and the optional inclusion of other elements, of similar or different nature than the recited elements, which do not materially change the basic or novel properties of the specified dosage regimen, method, or composition. As a nonlimiting example, a binding compound which consists essentially of a recited amino acid sequence may also include one or more amino acids that do not materially affect the properties of the binding compound.

Nucleic Acid Hybridization Background

The present invention includes anti-BTLA antibodies and fragments thereof, such as those encoded by nucleic acids as described in Tables 1-2, or those that encode amino acid residues as described in Table 4, as well as nucleic acids which hybridize thereto. Preferably, the nucleic acids hybridize under low stringency conditions, more preferably under moderate stringency conditions and most preferably under high stringency conditions and, preferably, exhibit BTLA binding activity. A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook, et al., supra). The conditions of temperature and ionic strength determine the "stringency" of the hybridization. Typical low stringency hybridization conditions include 55° C., 5×SSC, 0.1% SDS and no formamide; or 30% formamide, 5×SSC, 0.5% SDS at 42° C. Typical, moderate stringency hybridization conditions are similar to the low stringency conditions except the hybridization is carried out in 40% formamide, with 5× or 6×SSC and 0.1% SDS at 42° C. High stringency hybridization conditions are similar to low stringency conditions except the hybridization conditions are carried out in 50% formamide, 5× or 6×SSC at 42° C. or, optionally, at a higher temperature (e.g., 57° C., 59° C., 60° C., 62° C., 63° C., 65° C. or 68° C.). In general, SSC is 0.15M NaCl and 0.015M Na-citrate. Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook, et al., supra, 9.50-9.51). For hybridization with shorter nucleic acids, i.e., oligonucleotides, the position of mismatches becomes more important, and the length of the oligonucleotide determines its specificity (see Sambrook, et al., supra, 11.7-11.8).

Also included in the present invention are nucleic acids comprising nucleotide sequences and polypeptides comprising amino acid sequences which are at least about 70% identical, preferably at least about 80% identical, more preferably at least about 90% identical and most preferably at least about 95% identical (e.g., 95%, 96%, 97%, 98%, 99%, 100%) to the reference nucleotide and amino acid sequences when the comparison is performed by a BLAST algorithm wherein the parameters of the algorithm are selected to give the largest match between the respective sequences over the entire length of the respective reference sequences. Polypeptides comprising amino acid sequences which are at least about 70% similar, preferably at least about 80% similar, more preferably at least about 90% similar and most preferably at least about 95% similar (e.g., 95%, 96%, 97%, 98%, 99%, 100%) to any of the reference amino acid sequences when the comparison is performed with a BLAST algorithm wherein the parameters of the algorithm are selected to give the largest match between the respective sequences over the entire length of the respective reference sequences, are also included in the present invention.

Sequence identity refers to exact matches between the nucleotides or amino acids of two sequences which are being compared. Sequence similarity refers to both exact matches between the amino acids of two polypeptides which are being compared in addition to matches between nonidentical, biochemically related amino acids. Biochemically related amino acids which share similar properties and may be interchangeable are discussed above.

The following references regarding the BLAST algorithms are useful: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219: 555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, N.Y.

In another embodiment, the invention relates to an isolated nucleic acid, for example DNA, encoding the isolated antibodies or antigen binding fragment of the invention. In one embodiment, the isolated nucleic acid encodes an agonist antibody or antigen binding fragment thereof comprising at least one mature antibody light chain variable ($V_L$) domain and at least one mature antibody heavy chain variable ($V_H$) domain, wherein the $V_L$ domain comprises at least three CDRs having a sequence selected from SEQ ID NOs: 12-14, and the $V_H$ domain comprises at least at least three CDRs having a sequence selected from SEQ ID NOs: 5-7. In one embodiment, the isolated nucleic acid encodes the mature light and heavy chain variable region sequences of SEQ ID No:18 and SEQ ID NO:11, respectively. In some embodiments the isolated nucleic acid encodes both a light chain and a heavy chain on a single nucleic acid molecule, and in other embodiments the light and heavy chains are encoded on two or more separate nucleic acid molecules. In another embodiment the nucleic acids further encodes a signal sequence.

This invention also provides expression vectors comprising the isolated nucleic acids of the invention, wherein the nucleic acid is operably linked to control sequences that are recognized by a host cell when the host cell is transfected with the vector. Also provided are host cells comprising an expression vector of the present invention. The invention further relates to methods of producing a binding compound of the present invention comprising culturing a host cell harboring an expression vector encoding the binding compound in culture medium, and isolating the binding compound from the host cell or culture medium.

The invention also relates to antibodies or antigen binding fragments thereof that bind to the same epitope on human BTLA as antibody hu Mab8D5, hu Mab8A3, hu Mab21H6, or hu Mab19A7 (i.e., an agonist antibody) or hu Mab4C7 (i.e., an antagonist antibody blocking binding with HVEM), for example antibodies that are able to cross-block binding of any of the antibodies of the present invention.

By way of example, and not limitation, the fully human antibodies of the invention bind human BTLA with a $K_D$ value of no more than about 100 nM ($1 \times 10^{-7}$ M); preferably no more than about 10 nM; more preferably no more than about 1 nM. Even more preferred are embodiments in which the antibodies have $K_D$ values of no more than about 200 μM ($2\times10^{-10}$ M), 100 pM, 50 pM, 20 pM, 10 pM, 5 pM or even 2 pM.

Any suitable method for generating antibodies may be used to generate the antibodies of the present invention. Any suitable form of the human BTLA can be used as the immunogen (antigen) for the generation of the antibodies. By way of example and not limitation, any human BTLA isoform or fragment thereof may be used as the immunogen. Examples include, but are not limited to, isoforms and splice variants of human BTLA as described herein. In an alternative embodiment, rhesus BTLA can be used as the immunogen for generation of the antibodies.

In a preferred embodiment, fully-human monoclonal antibodies directed against BTLA are generated using transgenic mice carrying parts of the human immune system rather than the mouse system. These transgenic mice, which may be referred to, herein, as "HuMAb" mice, contain a human immunoglobulin gene miniloci that encodes unrearranged human heavy (μ and γ) and κ light chain immunoglobulin sequences, together with targeted mutations that inactivate the endogenous μ and κ chain loci (Lonberg, N., et al., (1994) Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg, N., et al., (1994), supra; reviewed in Lonberg, N. (1994) Handbook of Experimental Pharmacology 113:49-101; Lonberg, N., et al., (1995) Intern. Rev. Immunol. 13:65-93, and Harding, F., et al., (1995) Ann. N.Y. Acad. Sci. 764: 536-546). The preparation of HuMab mice is commonly known in the art and is described, for example, in Taylor, L., et al., (1992) Nucleic Acids Research 20:6287-6295; Chen, J., et al., (1993) International Immunology 5: 647-656; Tuaillon, et al., (1993) Proc. Natl. Acad. Sci. USA 90:3720-3724; Choi, et al., (1993) Nature Genetics 4:117-123; Chen, J., et al., (1993) EMBO J. 12: 821-830; Tuaillon, et al., (1994) J Immunol. 152:2912-2920; Lonberg, et al., (1994) Nature 368(6474): 856-859; Lonberg, N. (1994) Handbook of Experimental Pharmacology 113:49-101; Taylor, L., et al., (1994) International Immunology 6: 579-591; Lonberg, N., et al., (1995) Intern. Rev. Immunol. Vol. 13: 65-93; Harding, F., et al., (1995) Ann. N.Y. Acad. Sci. 764:536-546; Fishwild, D., et al., (1996) Nature Biotechnology 14: 845-851 and Harding, et al., (1995) Annals NY Acad. Sci. 764:536-546. See further, U.S. Pat. Nos. 5,545,806; 5,569,825; 5,625,126; 5,633,425; 5,789,650; 5,877,397; 5,661,016; 5,814,318; 5,874,299; 5,770,429 and 5,545,807; and International Patent Application Publication Nos. WO 98/24884; WO 94/25585; WO 93/12227; WO 92/22645 and WO 92/03918.

To generate fully human, monoclonal antibodies to BTLA, HuMab mice can be immunized with an antigenic BTLA polypeptide, preferably residues 31-152 of SEQ ID NO:35, as described by Lonberg, N., et al., (1994) Nature 368(6474): 856-859; Fishwild, D., et al., (1996) Nature Biotechnology 14: 845-851 and WO 98/24884. Preferably, the mice will be 6-16 weeks of age upon the first immunization. For example, a purified preparation of BTLA can be used to immunize the HuMab mice intraperitoneally and/or subcutaneously. The mice can also be immunized with whole HEK293 or CHO cells which are stably transfected with a BTLA gene. An "antigenic BTLA polypeptide" may refer to a BTLA polypeptide or any fragment thereof, preferably any BTLA fragment which elicits an anti-BTLA immune response, preferably in HuMab mice.

In general, HuMAb transgenic mice respond well when initially immunized intraperitoneally (IP) and/or subcutaneously with antigen in MPL®+TDM adjuvant (Sigma, Product No. M6536), followed by every other week or every two or three weeks IP immunizations (usually, up to a total of 6) with antigen in MPL®+TDM adjuvant. Mice can be immunized, first, with cells expressing BTLA (e.g., stably transfected HEK293 or CHO cells), then with a soluble fragment of BTLA (e.g., residues 31-152 of SEQ ID NO:35) and continually receive alternating immunizations with the two antigens. The immune response can be monitored over the course of the immunization protocol with plasma samples being obtained by retroorbital bleeds. The plasma can be screened for the presence of anti-BTLA antibodies, for example by ELISA, and mice with sufficient titers of immunoglobulin can be used for fusions. Mice can be boosted intravenously with antigen 4 days before sacrifice and removal of the spleen. It is expected that 2-3 fusions for each antigen may need to be performed. Several mice can be immunized for each antigen.

Hybridoma cells which produce the monoclonal, fully human anti-BTLA antibodies may be produced by methods which are commonly known in the art. These methods include, but are not limited to, the hybridoma technique originally developed by Kohler, et al., (1975) (Nature 256:495-497), as well as the trioma technique (Hering, et al., (1988) Biomed. Biochim. Acta. 47:211-216 and Hagiwara, et al., (1993) Hum. Antibod. Hybridomas 4:15), the human B-cell hybridoma technique (Kozbor, et al., (1983) Immunology Today 4:72 and Cote, et al., (1983) Proc. Natl. Acad. Sci. U.S.A 80:2026-2030), the EBV-hybridoma technique (Cole, et al., in *Monoclonal Antibodies and Cancer Therapy*, Alan R. Liss, Inc., pp. 77-96, 1985), and electric field based electrofusion using a Cyto Pulse large chamber cull fusion electroporator (Cyto Pulse Sciences, Inc., Glen Burnie, Md.). Preferably, mouse splenocytes are isolated and fused with PEG or by electrofusion to a mouse myeloma cell line based upon standard protocols. The resulting hybridomas may then be screened for the production of antigen-specific antibodies. For example, single cell suspensions of splenic lymphocytes from immunized mice may by fused to one-sixth the number of P3×63-Ag8.653 nonsecreting mouse myeloma cells (ATCC, CRL 1580) with 50% PEG. Cells may be plated at approximately $2\times10^5$ cells/mL in a flat bottom microtiter plate, followed by a two week incubation in selective medium containing 20% fetal Clone Serum, 18% "653" conditioned media, 5% origen (IGEN), 4 mM L-glutamine, 1 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After two weeks, cells may be cultured in medium in which the HAT is replaced with HT. Individual wells may then be screened by ELISA for human anti-BTLA monoclonal IgG antibodies. Once extensive hybridoma growth occurs, medium can be observed usually after 10-14 days. The antibody secreting hybridomas may be replated, screened again, and if still positive for human IgG, anti-BTLA monoclonal antibodies, can be subcloned at least twice by limiting dilution. The stable subclones may then be cultured in vitro to generate small amounts of antibody in tissue culture medium for characterization.

The anti-BTLA antibodies and antigen-binding fragments thereof of the present invention may also be produced recombinantly (e.g., in an *E. coli*/T7 expression system as discussed above). In this embodiment, nucleic acids encoding the antibody molecules of the invention (e.g., $V_H$ or $V_L$) may be inserted into a pET-based plasmid and expressed in the *E.* coli/T7 system. There are several methods by which to produce recombinant antibodies which are known in the art. One example of a method for recombinant production of antibodies is disclosed in U.S. Pat. No. 4,816,567. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors. Methods of transforming cells are well known in the art. See, for example, U.S. Pat. Nos. 4,399,216; 4,912,040; 4,740,461 and 4,959,455.

Anti-BTLA antibodies can also be synthesized by any of the methods set forth in U.S. Pat. No. 6,331,415.

Mammalian cell lines available as hosts for expression are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. When recombinant expression vectors encoding the heavy chain or antigen-binding portion or fragment thereof, the light chain and/or antigen-binding fragment thereof are introduced into mammalian host cells, the antibodies are produced by culturing the host cells for a period of time sufficient to allow for expression of the antibody in the host cells or, more preferably, secretion of the antibody into the culture medium in which the host cells are grown.

Antibodies can be recovered from the culture medium using standard protein purification methods. Further, expression of antibodies of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

It is likely that antibodies expressed by different cell lines or in transgenic animals will have different glycosylation from each other. However, all antibodies encoded by the nucleic acid molecules provided herein, or comprising the amino acid sequences provided herein are part of the instant invention, regardless of the glycosylation of the antibodies. Similarly, in certain embodiments, non fucosylated antibodies are advantageous, because they typically exhibit more potent efficacy than their fucosylated counterparts both in vitro and in vivo, and are not likely to be immunogenic because their carbohydrate structures are a normal component of natural human serum IgG.

The term "monoclonal antibody," as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Monoclonal antibodies are advantageous in that they may be synthesized by a hybridoma culture, essentially uncontaminated by other immunoglobulins. The modifier "monoclonal" indicates the character of the antibody as being amongst a substantially homogeneous population of antibodies, and is not to be construed as requiring production of the antibody by any particular method. As mentioned above, the monoclonal antibodies to be used in accordance with the present invention may be made by the hybridoma method first described by Kohler, et al., (1975) Nature 256: 495.

A polyclonal antibody is an antibody which was produced among or in the presence of one or more other, non-identical antibodies. In general, polyclonal antibodies are produced from a B-lymphocyte in the presence of several other B-lymphocytes which produced non-identical antibodies. Usually, polyclonal antibodies are obtained directly from an immunized animal.

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai, et al., (1990) Clin. Exp. Immunol. 79: 315-321, Kostelny, et al., (1992) J Immunol. 148:1547-1553. In addition, bispecific antibodies may be formed as "diabodies" (Holliger, et al., (1993) PNAS USA 90:6444-6448) or as "Janusins" (Traunecker, et al., (1991) EMBO J. 10:3655-3659 and Traunecker, et al., (1992) Int. J. Cancer Suppl. 7:51-52).

The present invention includes "chimeric antibodies"—an antibody which comprises a variable region of the present invention fused or chimerized with an antibody region (e.g., constant region) from another, non-human species (e.g., mouse, horse, rabbit, dog, cow, chicken). These antibodies may be used to modulate the expression or activity of BTLA in the non-human species.

"Single-chain Fv" or "sFv" antibody fragments have the $V_H$ and $V_L$ domains of an antibody, wherein these domains are present in a single polypeptide chain. Generally, the sFv polypeptide further comprises a polypeptide linker between the $V_H$ and $V_L$ domains which enables the sFv to form the desired structure for antigen binding. Techniques described for the production of single chain antibodies (U.S. Pat. Nos. 5,476,786; 5,132,405 and 4,946,778) can be adapted to produce anti-BTLA-specific single chain antibodies. For a review of sFv see Pluckthun in *The Pharmacology of Monoclonal Antibodies*, vol. 113, Rosenburg and Moore eds. Springer-Verlag, N.Y., pp. 269-315 (1994).

"Disulfide stabilized Fv fragments" and "dsFv" refer to antibody molecules comprising a variable heavy chain ($V_H$) and a variable light chain ($V_L$) which are linked by a disulfide bridge.

Antibody fragments within the scope of the present invention also include F(ab)$_2$ fragments which may be produced by enzymatic cleavage of an IgG by, for example, pepsin. Fab fragments may be produced by, for example, reduction of F(ab)$_2$ with dithiothreitol or mercaptoethylamine. A Fab fragment is a $V_L$-$C_L$ chain appended to a $V_H$-$C_{H1}$ chain by a disulfide bridge. A F(ab)$_2$ fragment is two Fab fragments which, in turn, are appended by two disulfide bridges. The Fab portion of an F(ab)$_2$ molecule includes a portion of the $F_c$ region between which disulfide bridges are located. An $F_v$ fragment is a $V_L$ or $V_H$ region.

Depending on the amino acid sequences of the constant domain of their heavy chains, immunoglobulins can be assigned to different classes. There are at least five major classes of immunoglobulins: IgA, IgD, IgE, IgG and IgM, and several of these may be further divided into subclasses (isotypes), e.g. IgG-1, IgG-2, IgG-3 and IgG-4; IgA-1 and IgA-2.

Antibody Engineering

Engineered antibodies of the invention include those in which modifications have been made to framework residues within $V_H$ and/or $V_L$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

For example, Table A shows regions where a framework region amino acid position (using Kabat numbering system) differs from the germline and how this position can be backmutated to the germline by the indicated substitutions:

TABLE A

Exemplary Backmutations

| Region | Framework Amino Acid Position (Kabat Numbering) | Backmutation |
|---|---|---|
| 4C7 $V_H$ | 25 | H25S |
| 4C7 $V_H$ | 68 | S68T |
| 4C7 $V_H$ | 82a | T82aT |

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043.

In addition or alternative to modifications made within the framework or CDR regions, antibodies of the invention can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention can be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In a preferred embodiment, the antibody is an IgG4 isotype antibody comprising a Serine to Proline mutation at a position corresponding to position 228 (S228P; EU index) in the hinge region of the heavy chain constant region. This mutation has been reported to abolish the heterogeneity of inter-heavy chain disulfide bridges in the hinge region (Angal et al. supra; position 241 is based on the Kabat numbering system). For example, in various embodiments, an anti-BTLA antibody of the invention can comprise the heavy chain variable region of 8D5 (SEQ ID NO: 9 or 11) or 4C7 (SEQ ID NO: 23 or 25) linked to a human IgG4 constant region in which the Serine at a position corresponding to position 241 as described in Angal et al., supra, has been mutated to Proline. Thus, for the 8D5 and 4C7 heavy chain variable regions linked to a human IgG4 constant region, this mutation corresponds to an S228P mutation by the EU index.

In one embodiment, the hinge region of CH1 is modified such that the number of cysteine residues in the hinge region is altered, e.g., increased or decreased. This approach is described further in U.S. Pat. No. 5,677,425. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745.

In another embodiment, the antibody is modified to increase its biological half life. Various approaches are possible. For example, one or more of the following mutations can be introduced: T252L, T254S, T256F, as described in U.S. Pat. No. 6,277,375. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551.

In another example, one or more amino acid residues within amino acid positions 231 and 239 are altered to thereby alter the ability of the antibody to fix complement. This approach is described further in PCT Publication WO 94/29351.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072. Moreover, the binding sites on human IgG1 for FcγR1, FcγRII, FcγRIII and FcRn have been mapped and variants with improved binding have been described (see Shields et al. (2001) *J. Biol. Chem.* 276: 6591-6604). Specific mutations at positions 256, 290, 298, 333, 334 and 339 were shown to improve binding to FcγRIII Additionally, the following combination mutants were shown to improve FcγRIII binding: T256A/S298A, S298A/E333A, S298A/K224A and S298A/E333A/K334A.

In still another embodiment, the glycosylation of an antibody is modified. For example, an aglycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (α (1,6)-fucosyltransferase), such that antibodies expressed in the Ms704, Ms705, and Ms709 cell lines lack fucose on their carbohydrates. The Ms704, Ms705, and Ms709 FUT8$^{-/-}$ cell lines were created by the targeted disruption of the FUT8 gene in CHO/DG44 cells using two replacement vectors (see U.S. Patent Publication No. 20040110704 and Yamane-Ohnuki et al. (2004) *Biotechnol Bioeng* 87:614-22). As another example, EP 1,176,195 describes a cell line with a functionally disrupted FUT8 gene, which encodes a fucosyl transferase, such that antibodies expressed in such a cell line exhibit hypofucosylation by reducing or eliminating the α-1,6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also Shields et al. (2002) *J. Biol. Chem.* 277:26733-26740). Antibodies with a modified glycosylation profile can also be produced in chicken eggs, as described in PCT Publication WO 06/089231. Alternatively, antibodies with a modified glycosylation profile can be produced in plant cells, such as Lemna (U.S. Pat. No. 7,632,983). Methods for production of antibodies in a plant system are disclosed in the U.S. Pat. No. 6,998,267 and U.S. Pat. No. 7,388,081. PCT Publication WO 99/54342 describes cell lines engineered to express glycoprotein-modifying glycosyl transferases (e.g., β(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17:176-180). Alternatively, the fucose residues of the antibody can be cleaved off using a fucosidase enzyme; e.g., the fucosidase α-L-fucosidase removes fucosyl residues from antibodies (Tarentino et al. (1975) *Biochem.* 14:5516-23).

Another modification of the antibodies herein that is contemplated by this disclosure is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See, e.g., EP 0 154 316 and EP 0 401 384.

Antibody Physical Properties

Antibodies of this disclosure can be characterized by their various physical properties, to detect and/or differentiate different classes thereof.

Antibodies of the present disclosure can contain one or more glycosylation sites in either the light or heavy chain variable region. Such glycosylation sites may result in increased immunogenicity of the antibody or an alteration of the pK of the antibody due to altered antigen binding (Marshall et al (1972) *Annu Rev Biochem* 41:673-702; Gala and Morrison (2004) *J Immunol* 172:5489-94; Wallick et al (1988) *J Exp Med* 168:1099-109; Spiro (2002) *Glycobiology* 12:43R-56R; Parekh et al (1985) *Nature* 316:452-7; Mimura et al. (2000) *Mol Immunol* 37:697-706). Glycosylation has been known to occur at motifs containing an N-X-S/T sequence. In some instances, it is preferred to have an anti-BTLA antibody that does not contain variable region glycosylation. This can be achieved either by selecting antibodies that do not contain the glycosylation motif in the variable region or by mutating residues within the glycosylation region.

In a preferred embodiment, the antibodies of the present disclosure do not contain asparagine isomerism sites. The deamidation of asparagine may occur on N-G or D-G sequences and result in the creation of an isoaspartic acid residue that introduces a kink into the polypeptide chain and decreases its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-BTLA antibody that contains a pI value that falls in the normal range. This can be achieved either by selecting antibodies with a pI in the normal range or by mutating charged surface residues.

Each antibody will have a characteristic melting temperature, with a higher melting temperature indicating greater overall stability in vivo (Krishnamurthy R and Manning M C (2002) *Curr Pharm Biotechnol* 3:361-71). Generally, it is preferred that the $T_{M1}$ (the temperature of initial unfolding) be greater than 60° C., preferably greater than 65° C., even more preferably greater than 70° C. The melting point of an antibody can be measured using differential scanning calorimetry (Chen et al (2003) *Pharm Res* 20:1952-60; Ghirlando et al (1999) *Immunol Lett* 68:47-52) or circular dichroism (Murray et al. (2002) *J. Chromatogr Sci* 40:343-9).

In a preferred embodiment, antibodies are selected that do not degrade rapidly. Degradation of an antibody can be measured using capillary electrophoresis (CE) and MALDI-MS (Alexander A J and Hughes D E (1995) *Anal Chem* 67:3626-32).

In another preferred embodiment, antibodies are selected that have minimal aggregation effects, which can lead to the triggering of an unwanted immune response and/or altered or unfavorable pharmacokinetic properties. Generally, antibodies are acceptable with aggregation of 25% or less, preferably 20% or less, even more preferably 15% or less, even more preferably 10% or less and even more preferably 5% or less. Aggregation can be measured by several techniques, including size-exclusion column (SEC), high performance liquid chromatography (HPLC), and light scattering.

Antibody Conjugates

The anti-BTLA antibody molecules of the invention may also be conjugated to a chemical moiety. The chemical moiety may be, inter alia, a polymer, a radionuclide or a cytotoxic factor. Preferably the chemical moiety is a polymer which increases the half-life of the antibody molecule in the body of a subject. Suitable polymers include, but are not limited to, polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee, et al., (1999) (Bioconj. Chem. 10:973-981) discloses PEG conjugated single-chain antibodies. Wen, et al., (2001) (Bioconj. Chem. 12:545-553) disclose conjugating antibodies with PEG which is attached to a radiometal chelator (diethylenetriaminpentaacetic acid (DTPA)).

The antibodies and antibody fragments of the invention may also be conjugated with labels such as $^{99}$Tc, $^{90}$Y, $^{111}$In, $^{32}$P, $^{14}$C, $^{125}$I, $^{3}$H, $^{131}$I, $^{11}$C, $^{15}$O, $^{13}$N, $^{18}$F, $^{35}$S, $^{51}$Cr, $^{57}$To, $^{226}$Ra, $^{60}$Co, $^{59}$Fe, $^{57}$Se, $^{152}$Eu, $^{67}$CU, $^{217}$Ci, $^{211}$At, $^{212}$Pb, $^{47}$Sc, $^{109}$Pd, $^{234}$Th, and $^{40}$K, $^{157}$Gd, $^{55}$Mn, $^{52}$Tr and $^{56}$Fe.

The antibodies and antibody fragments of the invention may also be conjugated with fluorescent or chemilluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}$Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

The antibody molecules may also be conjugated to a cytotoxic factor such as diptheria toxin, *Pseudomonas aeruginosa* exotoxin A chain, ricin A chain, abrin A chain, modeccin A chain, alpha-sarcin, *Aleurites fordii* proteins and compounds (e.g., fatty acids), dianthin proteins, *Phytoiacca americana* proteins PAPI, PAPII, and PAP-S, *momordica charantia* inhibitor, curcin, crotin, *saponaria officinalis* inhibitor, mitogellin, restrictocin, phenomycin, and enomycin.

Any method known in the art for conjugating the antibody molecules of the invention to the various moieties may be employed, including those methods described by Hunter, et al., (1962) Nature 144:945; David, et al., (1974) Biochemistry 13:1014; Pain, et al., (1981) J. Immunol. Meth. 40:219; and Nygren, J., (1982) Histochem. and Cytochem. 30:407. Methods for conjugating antibodies are conventional and very well known in the art.

In yet other embodiments, different constant domains may be appended to humanized $V_L$ and $V_H$ regions derived from the CDRs provided herein. For example, if a particular intended use of an antibody (or fragment) of the present invention were to call for altered effector functions, a heavy chain constant domain other than IgG1 may be used, or hybrid IgG1/IgG4 may be utilized.

Although IgG1 antibodies provide for long half-life and for effector functions, such as complement activation and antibody-dependent cellular cytotoxicity, such activities may not be desirable for all uses of the antibody. In such instances an IgG4 constant domain, for example, may be used. In hu Mab8D5, the IgG4 constant domain differs from the native human IgG4 constant domain (Swiss-Prot Accession No. P01861.1) at position 108 (corresponding to position 228 in the EU system and position 241 in the KABAT system), where the native Ser108 is replaced with Pro, in order to prevent a potential inter-chain disulfide bond between Cys106 and Cys109 (corresponding to positions Cys 226 and Cys 229 in the EU system and positions Cys 239 and Cys 242 in the KABAT system) that could interfere with proper intra-chain disulfide bond formation. See Angal et al. (1993) *Mol. Immunol.* 30:105.

For hu Mab21H6, hu Mab8A3, hu Mab15C5, hu Mab19A7, and hu Mab 20H4, the sequences described in Table 7 are based on human heavy chain IgG1.

Diseases

The invention also provides methods of treating subjects, including human subjects, in need of treatment with the isolated antibodies or antigen binding fragment thereof with the antibody or antigen binding fragment thereof, preferably a fully human antibody, of the present invention. Such subjects may have an inflammatory or autoimmune disorder, such as inflammatory bowel disorders (e.g., Crohn's disease, ulcerative colitis, and inflammatory bowel disease), inflammatory fibrosis (e.g., scleroderma, lung fibrosis, and cirrhosis), rheumatoid arthritis (RA), osteoarthritis, osteoporosis, asthma (including allergic asthma), allergies, chronic obstructive pulmonary disease (COPD), multiple sclerosis, psoriasis, uveitis, graft versus host disease (GVHD), juvenile early-onset Type I diabetes, transplant rejection, SLE, and Sjögren's syndrome. Such methods of treatment may further comprise administering one or more additional therapeutic agents, such as immunosuppressive or anti-inflammatory agents. By way of example, and not limitation, inflammatory bowel disorders are treated by the methods described herein. In a particularly preferred embodiment, Crohn's disease and ulcerative colitis are treated by the methods described herein.

Inflammatory Bowel Disease (IBD)

IBD is the name for a group of disorders (e.g. Crohn's disease and ulcerative colitis) in which the intestines become inflamed, resulting in abdominal cramps and pain, diarrhea, weight loss and intestinal bleeding. IBD affects over 600,000 Americans. Conventional treatment options include sulfasalazine, corticosteroids (e.g. prednisone), immune system suppressors such as azathioprine and mercaptopurine, or an antibiotic (e.g., metronidazole) for Crohn's disease. Therapeutic monoclonal antibody treatments include etanercept, natalizumab and infliximab.

The anti-BTLA antibodies of the present invention may be used to treat IBD in subjects in need of such treatment. The anti-BTLA antibodies of the present invention may also be combined with other treatments for IBD, e.g. IL-10 (see U.S. Pat. Nos. 5,368,854, 7,052,686), steroids and sulfasalazine.

Graft-Versus-Host Disease (GVHD)

Graft-versus-host disease (GVHD) is a common complication of allogeneic bone marrow transplantation in which functional immune cells in the transplanted marrow recognize the recipient as "foreign" and mount an immunologic attack. It can also take place in a blood transfusion under certain circumstances. Three criteria are typically associated with GVHD:

1) Administration of an immunocompetent graft, with viable and functional immune cells;

2) The recipient is immunologically disparate-histoincompatible; and

3) The recipient is immunocompromised and therefore cannot destroy or inactivate the transplanted cells.

After bone marrow transplantation, T cells present in the graft attack the tissues of the transplant recipient after perceiving host tissues as antigenically foreign. The T cells produce an excess of cytokines, including TNF alpha and interferon-gamma (IFNg). A wide range of host antigens can initiate graft-versus-host-disease, among them the human leukocyte antigens (HLAs). However, graft-versus-host disease can occur even when HLA-identical siblings are the donors. HLA-identical siblings or HLA-identical unrelated donors often have genetically different proteins (i.e., minor histocompatibility antigens) that can be presented by MHC molecules to the recipient's T-cells, which see these antigens as foreign and so mount an immune response.

BTLA agonist antibodies are expected to inhibit the activation, proliferation and effector function of grafted T and B cells that react to allogeneic antigens (including, but not limited to minor and major histocompatibility antigens) present in tissues of the recipient or host. Inhibition of these graft derived T and B cells is expected to occur by virtue of their expression of BTLA on the cell surface. While not being bound by theory, a BTLA agonist antibody is expected to inhibit pathogenic immune responses by 'forced engagement'. BTLA agonist antibodies may inhibit pathogenic immune responses indirectly for instance through the activation of other inhibitory cells such as regulatory T cells, or through modulation of antigen-presenting cells. BTLA agonist antibodies are expected to suppress or inhibit anti-host responses by lymphocytes originating from the graft either alone or in combination with other immune suppressive agents, used to prevent or treat the symptoms of graft versus host disease.

In a further embodiment, the invention also relates to methods of treatment comprising administration of a therapeutically effective amount of an anti-BTLA antibody or antigen binding fragment thereof in combination with one or more other therapeutic agents. By way of example, and not limitation, the one or more therapeutic agents include anti-IL-23, IL-1β, IL-6, TGF-β, CTLA4 fusion proteins, and small molecule anti-inflammatories, such as mycophenolate mofetil methotrexate (See, e.g., Veldhoen (2006) *Immunity* 24:179-189; Dong (2006) *Nat. Rev. Immunol.* 6(4):329-333) or a combination. In various embodiments the one or more other therapeutic agents is administered before, concurrently with, or after the anti-BTLA antibody or antigen binding fragment thereof.

Additionally, in certain embodiments, the anti-BTLA antibody or antigen binding fragment thereof can be administered in combination with immunosuppressive drugs used to treat transplant rejection including any combination of one or more of the following:

calcineurin inhibitors (e.g., ciclosporin and tacrolimus),
mTOR inhibitors (e.g., sirolimus and everolimus),
anti-proliferatives (e.g., azathioprine and mycophenolic acid),
corticosteroids (e.g., prednisolone and hydrocortisone),
antibodies with immunosuppressive effects (e.g., monoclonal anti-IL-2Rα receptor antibodies including basiliximab and daclizumab),
and polyclonal anti-T-cell antibodies (e.g., anti-thymocyte globulin (ATG) and anti-lymphocyte globulin (ALG)).

The invention also relates to compositions and formulations of the antibodies or antigen binding fragment thereof the present invention, comprising the binding compound and a pharmaceutically acceptable carrier or diluent, and optionally one or more immunosuppressive or anti-inflammatory agents.

Experimental and Diagnostic Uses

The antibodies and fragments of the invention may be used as affinity purification agents. In this process, the antibodies or fragments are immobilized on a solid phase such a Sephadex resin or filter paper, using methods well known in the art. The immobilized antibody or fragment is contacted with a sample containing the BTLA protein (or fragment thereof) to be purified, and thereafter the support is washed with a suitable solvent that will remove substantially all the material in the sample except the BTLA protein, which is bound to the immobilized antibody or fragment. Finally, the support is washed with a solvent which elutes the bound BTLA from the column (e.g., protein A). Such immobilized antibodies form part of the present invention.

The present invention also provides antigens for generating secondary antibodies which are useful for example for performing Western blots and other immunoassays discussed herein. Specifically, the present invention includes polypeptides comprising the variable regions and/or CDR sequences which may be used to generate an anti-BTLA or anti-BTLA secondary antibody. Detectably labeled anti-hu Mab8D5, hu Mab8A3, hu Mab21H6, hu Mab19A7, hu Mab4C7 or anti-Mab8D5, hu Mab8A3, hu Mab21H6, hu Mab19A7, hu Mab4C7 secondary antibodies are within the scope of the present invention.

Anti-BTLA antibodies or fragments thereof may also be useful in diagnostic assays for BTLA protein, e.g., detecting its expression in specific cells, tissues, or serum. Such diagnostic methods may be useful in various disease diagnoses.

For example, embodiments of the invention include ELISA assays (enzyme-linked immunosorbent assay) incorporating the use of an anti-BTLA antibody or fragment thereof of the invention. For example, in an embodiment of the invention, such a method comprises the following steps:

(a) coat a substrate (e.g., surface of a microtiter plate well, e.g., a plastic plate) with anti-BTLA antibody or antigen-binding fragment thereof;

(b) apply a sample to be tested for the presence of BTLA to the substrate;

(c) wash the plate, so that unbound material in the sample is removed;

(d) apply detectably labeled antibodies (e.g., enzyme-linked antibodies) which are also specific to the BTLA antigen;

(e) wash the substrate, so that the unbound, labeled antibodies are removed;

(f) if the labeled antibodies are enzyme linked, apply a chemical which is converted by the enzyme into a fluorescent signal; and (g) detect the presence of the labeled antibody.

In an embodiment of the invention, the labeled antibody is labeled with peroxidase which react with ABTS (e.g., 2,2'-azino-bis(3-ethylbenzthiazoline-6-sulphonic acid)) or 3,3',5,5'-Tetramethylbenzidine to produce a color change which is detectable. Alternatively, the labeled antibody is labeled with a detectable radioisotope (e.g., $^3$H) which can be detected by scintillation counter in the presence of a scintillant. An anti-BTLA antibody of the invention may be used in a Western blot or immuno protein blot procedure. Such a procedure forms part of the present invention and includes e.g.:

(1) contacting a membrane or other solid substrate to be tested for the presence of bound BTLA or a fragment thereof with an anti-BTLA antibody or antigen-binding fragment thereof of the invention. Such a membrane may take the form of a nitrocellulose or vinyl-based (e.g., polyvinylidene fluoride (PVDF)) membrane to which proteins to be tested for the presence of BTLA in a non-denaturing PAGE (polyacrylamide gel electrophoresis) gel or SDS-PAGE (sodium dodecyl sulfate polyacrylamide gel electrophoresis) gel have been transferred (e.g., following electrophoretic separation in the gel). Before contact of membrane with the anti-BTLA antibody or fragment, the membrane is optionally blocked, e.g., with non-fat dry milk or the like so as to bind non-specific protein binding sites on the membrane.

(2) washing the membrane one or more times to remove unbound anti-BTLA antibody or fragment and other unbound substances; and (3) detecting the bound anti-BTLA antibody or fragment.

Detection of the bound antibody or fragment may be by binding the antibody or fragment with a secondary antibody (an anti-immunoglobulin antibody) which is detectably labeled and, then, detecting the presence of the secondary antibody.

The anti-BTLA antibodies and antigen-binding fragments thereof of the invention may also be used for immunohistochemistry. Such a method forms part of the present invention and comprises, e.g., (1) contacting a cell to be tested for the presence of BTLA with an anti-BTLA antibody or antigen-binding fragment thereof of the invention; and (2) detecting the antibody or fragment on or in the cell.

If the antibody or fragment itself is detectably labeled, it can be detected directly. Alternatively, the antibody or fragment may be bound by a detectably labeled secondary antibody which is detected.

Certain anti-BTLA antagonist antibodies and antigen-binding fragments thereof of the invention may also be used for in vivo tumor imaging. Such a method forms part of the present invention and may include injection of a radiolabeled anti-BTLA antibody or antigen-binding fragment thereof of the invention into the body of a patient to be tested for the presence of a tumor associated with BTLA expression followed by nuclear imaging of the body of the patient to detect the presence of the labeled antibody or fragment e.g., at loci comprising a high concentration of the antibody or fragment which are bound to the tumor.

Imaging techniques include SPECT imaging (single photon emission computed tomography) or PET imaging (positron emission tomography). Labels include e.g., iodine-123 ($^{123}$I) and technetium-99m ($^{99m}$Tc), e.g., in conjunction with SPECT imaging or $^{11}$C, $^{13}$N, $^{15}$O or $^{18}$F, e.g., in conjunction with PET imaging or Indium-111 (See e.g., Gordon et al., (2005) International Rev. Neurobiol. 67:385-440).

Kits

The present invention also provides kits comprising the components of the combinations of the invention in kit form. A kit of the present invention includes one or more components including, but not limited to, a binding composition, as discussed herein, which specifically binds BTLA (e.g., agonist antibodies hu Mab8D5, hu Mab8A3, hu Mab21H6, or hu Mab19A7, or antagonist antibody hu Mab4C7) in association with one or more additional components including, but not limited to a pharmaceutically acceptable carrier and/or a chemotherapeutic agent, as discussed herein. The binding composition and/or the chemotherapeutic agent can be formulated as a pure composition or in combination with a pharmaceutically acceptable carrier, in a pharmaceutical composition.

In one embodiment, a kit includes a binding composition of the invention (e.g., agonist antibodies hu Mab8D5, hu Mab8A3, hu Mab21H6, or hu Mab19A7, or antagonist antibody hu Mab4C7) or a pharmaceutical composition thereof in one container (e.g., in a sterile glass or plastic vial) and a pharmaceutical composition thereof and/or a chemotherapeutic agent in another container (e.g., in a sterile glass or plastic vial).

In another embodiment of the invention, the kit comprises a combination of the invention, including a binding composition component (e.g., agonist antibodies hu Mab8D5, hu Mab8A3, hu Mab21H6, or hu Mab19A7, or antagonist antibody hu Mab4C7) along with a pharmaceutically acceptable carrier, optionally in combination with one or more chemotherapeutic agent component formulated together, optionally, in a pharmaceutical composition, in a single, common container.

If the kit includes a pharmaceutical composition for parenteral administration to a subject, the kit can include a device for performing such administration. For example, the kit can include one or more hypodermic needles or other injection devices as discussed above.

The kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

Pharmaceutical Compositions and Administration

To prepare pharmaceutical or sterile compositions of the anti-huBTLA antibodies of the present invention, the antibody is admixed with a pharmaceutically acceptable carrier or excipient. See, e.g., *Remington's Pharmaceutical Sciences* and *U.S. Pharmacopeia: National Formulary*, Mack Publishing Company, Easton, Pa. (1984).

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.). In one embodiment, anti-BTLA antibodies of the present invention are diluted to an appropriate concentration in a sodium acetate solution pH 5-6, and NaCl or sucrose is added for tonicity. Additional agents, such as polysorbate 20 or polysorbate 80, may be added to enhance stability.

Toxicity and therapeutic efficacy of the antibody compositions, administered alone or in combination with another agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). Antibodies exhibiting high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

The mode of administration can vary. Suitable routes of administration include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. Administration can be carried out in a variety of conventional ways, such as oral ingestion, inhalation, insufflation, topical application or cutaneous, transdermal, subcutaneous, intraperitoneal, parenteral, intraarterial or intravenous injection. Intravenous administration to the patient is preferred.

Alternately, one may administer the antibody in a local rather than systemic manner, for example, via injection of the antibody directly into an arthritic joint or pathogen-induced lesion characterized by immunopathology, often in a depot or sustained release formulation. Furthermore, one may administer the antibody in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

The administration regimen depends on several factors, including the serum or tissue turnover rate of the therapeutic antibody, the level of symptoms, the immunogenicity of the therapeutic antibody, and the accessibility of the target cells in the biological matrix. Preferably, the administration regimen delivers sufficient therapeutic antibody to effect improvement in the target disease state, while simultaneously minimizing undesired side effects. Accordingly, the amount of biologic delivered depends in part on the particular therapeutic antibody and the severity of the condition being treated. Guidance in selecting appropriate doses of therapeutic antibodies is available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert, et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602).

Determination of the appropriate dose is made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. Preferably, a biologic that will be used is derived from the same species as the animal targeted for treatment, thereby minimizing an inflammatory, autoimmune, or proliferative response to the reagent. In the case of human subjects, for example, chimeric, humanized and fully human antibodies are preferred.

Antibodies, antibody fragments, and cytokines can be provided by continuous infusion, or by doses administered, e.g., daily, 1-7 times per week, weekly, bi-weekly, monthly, bimonthly etc. Doses may be provided intravenously, subcutaneously, topically, orally, nasally, rectally, intramuscular, intracerebrally, intraspinally, or by inhalation. A total weekly dose is generally at least 0.05 µg/kg body weight, more generally at least 0.2 µg/kg, 0.5 µg/kg, 1 µg/kg, 10 µg/kg, 100 µg/kg, 0.25 mg/kg, 1.0 mg/kg, 2.0 mg/kg, 5.0 mg/ml, 10 mg/kg, 25 mg/kg, 50 mg/kg or more (see, e.g., Yang, et al. (2003) *New Engl. J. Med.* 349:427-434; Herold, et al. (2002) *New Engl. J. Med.* 346:1692-1698; Liu, et al. (1999) *J. Neurol. Neurosurg. Psych.* 67:451-456; Portielji, et al. (20003) *Cancer Immunol. Immunother.* 52:133-144). Doses may also be provided to achieve a pre-determined target concentration of anti-BTLA antibody in the subject's serum, such as 0.1, 0.3, 1, 3, 10, 30, 100, 300 µg/ml or more. In other embodiments, a fully human BTLA antibody of the present invention is administered subcutaneously or intravenously, on a weekly, biweekly or "every 4 weeks" basis at 10, 20, 50, 80, 100, 200, 500, 1000 or 2500 mg/subject.

As used herein, "inhibit" or "treat" or "treatment" includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a vertebrate subject with a disorder, disease or symptom, or with the potential to develop such a disorder, disease or symptom.

As used herein, the terms "therapeutically effective amount", "therapeutically effective dose" and "effective amount" refer to an amount of a BTLA binding compound of the invention that, when administered alone or in combination with an additional therapeutic agent to a cell, tissue, or subject, is effective to prevent or ameliorate one or more symptoms of a disease or condition or the progression of such disease or condition. A therapeutically effective dose further refers to that amount of the binding compound sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%.

Methods for co-administration with a second therapeutic agent, e.g., cytokine, another therapeutic antibody, steroid, chemotherapeutic agent, or antibiotic are well known in the art, see, e.g., Hardman, et al. (eds.) (2001) *Goodman and Gilman's The Pharmacological Basis of Therapeutics*, $10^{th}$ ed., McGraw-Hill, New York, N.Y.; Poole and Peterson (eds.) (2001) *Pharmacotherapeutics for Advanced Practice: A Practical Approach*, Lippincott, Williams & Wilkins, Phila., Pa.; Chabner and Longo (eds.) (2001) *Cancer Chemotherapy and Biotherapy*, Lippincott, Williams & Wilkins, Phila., Pa. The pharmaceutical composition of the invention may also contain immunosuppressive or immunomodulating agents. Any suitable immunosuppressive agent can be employed, including but not limited to anti-inflammatory agents, corticosteroids, cyclosporine, tacrolimus (i.e., FK-506), sirolimus, interferons, soluble cytokine receptors (e.g., sTNRF and sIL-1R), agents that neutralize cytokine activity (e.g., infliximab, etanercept), mycophenolate mofetil, 15-deoxyspergualin, thalidomide, glatiramer, azathioprine, leflunomide, cyclophosphamide, methotrexate, and the like. The pharmaceutical composition can also be employed with other therapeutic modalities such as phototherapy and radiation.

The BTLA binding compounds of the present invention can also be used in combination with one or more agonists or antagonists of other cytokines (e.g. antibodies), including but not limited to, IL-23, IL-1β, IL-6, CTLA-4, CTLA-4/Ig fusion, and TGF-β. See, e.g., Veldhoen (2006) *Immunity* 24:179-189; Dong (2006) *Nat. Rev. Immunol.* 6(4):329-333. In various embodiments, the BTLA binding compound of the invention is administered before, concurrently with, or after administration of the another agonist/s or antagonist/s. In one embodiment, a BTLA binding compound of the present invention is used in treatment of the acute early phase of an adverse immune response (e.g. MS, Crohn's Disease, juvenile early-onset type I diabetes) alone or in combination with an IL-23 antagonist. In the latter case, the BTLA binding compound may be gradually decreased and treatment with the antagonist of IL-23 alone is continued to maintain suppression of the adverse response. Alternatively, antagonists to IL-1β, IL-6 and/or TGF-β may be administered concurrently, before or after an BTLA binding compound of the present invention. See Cua and Kastelein (2006) *Nat. Immunol.* 7:557-559; Tato and O'Shea (2006) *Nature* 441:166-168; Iwakura and Ishigame (2006) *J. Clin. Invest.* 116:1218-1222.

Typical veterinary, experimental, or research subjects include monkeys, dogs, cats, rats, mice, rabbits, guinea pigs, horses, and humans.

Uses

The present invention provides methods for using engineered anti-BTLA antibodies for the treatment and diagnosis of inflammatory disorders and conditions, as well as autoimmune and proliferative disorders. Methods are provided for the diagnosis, prevention or treatment of inflammatory bowel disease (IBD), multiple sclerosis (MS), chronic obstructive pulmonary disease (COPD), cystic fibrosis (CF), psoriasis, systemic scleroderma, GVHD, allograft rejection, SLE, Sjögren's syndrome, juvenile early-onset type I diabetes autoimmune myocarditis and peritoneal adhesions (See, e.g., Chung et al. (2002) *J. Exp. Med.* 195:1471-78).

In certain embodiments, the antibody or antigen binding fragments of the invention, which specifically bind to human BTLA, can be used to increase, enhance, stimulate, or up-regulate an immune response related to BTLA activity. In certain embodiments, antibodies of the present invention that do not block binding of BTLA to HVEM (e.g. agonist antibodies Hu Mab8D5, huMab8A3) are used therapeutically to stabilize BTLA in subjects in need of prolonged BTLA activity. Anti-BTLA agonist antibodies (e.g., Hu Mab8D5, huMab8A3, hu Mab21H6, and hu Mab19A7) activate inhibitory receptor function of BTLA. Subjects who would benefit from such treatment include patients suffering from an inflammatory or autoimmune disorder, such as inflammatory bowel disorders (e.g., Crohn's disease, ulcerative colitis, and inflammatory bowel disease), inflammatory fibrosis (e.g., scleroderma, lung fibrosis, and cirrhosis), rheumatoid arthritis (RA), osteoarthritis, osteoporosis, asthma (including allergic asthma), allergies, chronic obstructive pulmonary disease (COPD), multiple sclerosis, psoriasis, uveitis, graft versus host disease (GVHD), juvenile early-onset Type I diabetes, transplant rejection, SLE, and Sjögren's syndrome. Such methods of treatment may further comprise administering one or more additional therapeutic agents, such as immunosuppressive or anti-inflammatory agents.

Rheumatoid Arthritis (RA)

RA is a progressive, systemic disease characterized by inflammation of the synovial joints affecting about 0.5% of the world's population. See, Emery (2006) *BMJ* 332:152-155. Joint inflammation can lead to deformity, pain, stiffness and swelling, and ultimately to irreversible deterioration of the joint. Affected joints include knees, elbows, neck and joints of the hands and feet. Conventional treatment involves use of NSAIDs to alleviate symptoms, followed by administration of disease modifying antirheumatic drugs (DMARDs) such as gold, penicillamine, sulfasalazine and methotrexate. Recent advances include treatment with TNF-α, inhibitors, including monoclonal antibodies, such as infliximab, adalimumab and golimumab, and receptor fusion proteins, such as etanercept. Treatment with these TNF-α, inhibitors dramatically reduces structural damage from the disease.

The anti-BTLA agonist antibodies of the present invention may be used to treat RA in subjects in need of such treatment. The anti-BTLA antibodies of the present invention may also be combined with other treatments for RA, e.g. methotrexate, azathioprine, cyclophosphamide, steroids, mycophenolate mofetil, NSAIDs, or TNF-α, inhibitors (antibodies or receptor fragments).

In one embodiment, the anti-BTLA antibodies of the present invention are used to treat human subjects who have not previously responded adequately to treatment with DMARDs alone. In another embodiment, treatment with the anti-BTLA antibodies of the present invention is begun early in the course of disease, without requiring prior failure of DMARD therapy. Such early intervention may be appropriate, for example, once the safety of the antibody therapy has been firmly established.

Clinical improvement is measured by determining the ACR score, as described in more detail in Example 18. In various embodiments, ACR scores of 20, 50, and 70 are the desired endpoint, and these endpoints may be assessed at any appropriate point in the course of treatment, such as 5, 10, 15, 24, 40, 50 or more weeks.

Inflammatory Bowel Disease (IBD)

IBD is the name for a group of disorders (e.g. Crohn's disease and ulcerative colitis) in which the intestines become inflamed, resulting in abdominal cramps and pain, diarrhea, weight loss and intestinal bleeding. IBD affects over 600,000 Americans. Conventional treatment options include sulfasalazine, corticosteroids (e.g. prednisone), immune system suppressors such as azathioprine and mercaptopurine, or an antibiotic (e.g. metronidazole) for Crohn's disease. Therapeutic monoclonal antibody treatments include etanercept, natalizumab and infliximab.

The anti-BTLA agonist antibodies of the present invention may be used to treat IBD in subjects in need of such treatment. The anti-BTLA agonist antibodies of the present invention may also be combined with other treatments for IBD, e.g. IL-10 (see U.S. Pat. Nos. 5,368,854, 7,052,686), steroids and sulfasalazine.

Psoriasis

The skin serves as an important boundary between the internal milieu and the environment, preventing contact with potentially harmful antigens. In the case of antigen/pathogen penetration, an inflammatory response is induced to eliminate the antigen. This response leads to a dermal infiltrate that consists predominantly of T cells, polymorphonuclear cells, and macrophages (see, e.g., Williams and Kupper (1996) Life Sci., 58:1485-1507.) Normally, this inflammatory response, triggered by the pathogen, is under tight control and will be halted upon elimination of the pathogen.

In certain cases this inflammatory response occurs without external stimuli and without proper controls, leading to cutaneous inflammation. The present invention provides methods for treating and diagnosing cutaneous inflammation. Cutaneous inflammation, the result of the cellular infiltrate noted above as well as the secreted cytokines from these cells, encompasses several inflammatory disorders such as cicatricial pemphigoid, scleroderma, hidradenitis suppurativa, toxic epidermal necrolysis, acne, osteitis, graft vs. host disease (GvHD), pyoderma gangrenosum, and Behcet's Syndrome (see, e.g., Williams and Griffiths (2002) Clin. Exp. Dermatol., 27:585-590). The most common form of cutaneous inflammation is psoriasis.

Psoriasis is characterized by T cell mediated hyperproliferation of keratinocytes coupled with an inflammatory infiltrate. The disease has certain distinct overlapping clinical phenotypes including chronic plaque lesions, skin eruptions, and pustular lesions (see, e.g., Gudjonsson et al. (2004) Clin Exp. Immunol. 135:1-8). Approximately 10% of psoriasis patients develop arthritis. The disease has a strong but complex genetic predisposition, with 60% concordance in monozygotic twins.

The typical psoriatic lesion is a well defined erythematosus plaque covered by thick, silvery scales. The inflammation and hyperproliferation of psoriatic tissue is associated with a different histological, antigenic, and cytokine profile than normal skin. Among the cytokines associated with psoriasis are: TNFα, IL-19, IL-18, IL-15, IL-12, IL-7, IFNγ, IL-17A and IL-23 (see Gudjonsson et al., supra).

Anti-BTLA antibodies of the present invention, either alone or in combination with other agents, may also be used in prevention, treatment, diagnosis and prediction of psoriasis flare-ups.

Systemic Lupus Erythematosis (SLE)

Lupus erythematosus is a connective tissue disease. Lupus is a chronic inflammatory disease that occurs when the body's immune system attacks its own tissues and organs. Inflammation caused by lupus can affect many different body systems, including joints, skin, kidneys, blood cells, heart, and lungs. Lupus occurs more frequently in women than men, although the reasons for this are unknown. Four types of lupus exist—systemic lupus erythematosus, discoid lupus erythematosus, drug-induced lupus erythematosus and neonatal lupus. Of these, systemic lupus erythematosus is the most common and serious form of lupus. In certain embodiments, anti-BTLA agonist antibodies of the present invention may be used to treat lupus in subjects in need of such treatment. The anti-BTLA antibodies may be combined with other treatments for lupus including NSAID's, certain anti-malaria drugs (e.g., hydroxychloroquine and corticosteroids, immunosuppressive drugs (e.g., cyclophosphamide (Cytoxan) and azathioprine (Imuran), and mycophenolate mofetil (CellCept)), Rituximab, and Dehydroepiandrosterone (DHEA).

Sjögren's syndrome is another chronic disorder that causes dry eyes and a dry mouth. In certain embodiments, anti-BTLA antibodies of the present invention may be useful for treating individuals with Sjögren's syndrome. The anti-BTLA antibodies of the present invention may also be combined with other treatments for Sjögren's syndrome, along the lines described for Lupus.

Multiple Sclerosis (MS)

MS is thought to be an autoimmune disease of the central nervous system (CNS) involving loss of myelin from nerve fibers, resulting in plaques or lesions. The most common form is relapsing/remitting MS in which well defined symptomatic flare-ups occur, followed by periods of partial or complete remission. Conventional treatment options include interferon-β-1a and -1b, mitoxantrone, the tetrapeptide glatiramer acetate, therapeutic alpha-4-integrin-specific antibodies (natalizumab), or small molecule antagonists of alpha-4-integrin (e.g. those disclosed at WO2003/084984).

In certain embodiments, anti-BTLA agonist antibodies of the present invention may be used to treat MS in subjects in need of such treatment. The anti-BTLA antibodies may also be combined with other treatments for MS, e.g. interferon-β, interferon-α, steroids or alpha-4-integrin-specific antibodies.

Cancer

Antagonist antibody or antigen binding fragments of the invention (exemplified by hu Mab4C7) can be used to treat cancer (i.e., to inhibit the growth or survival of tumor cells). Preferred cancers whose growth may be inhibited using the antagonist antibodies of the invention include cancers typically responsive to immunotherapy, but also cancers that have not hitherto been associated with immunotherapy. Non-limiting examples of preferred cancers for treatment include melanoma (e.g., metastatic malignant melanoma), renal cancer (e.g. clear cell carcinoma), prostate cancer (e.g. hormone refractory prostate adenocarcinoma), pancreatic adenocarcinoma, breast cancer, colon cancer, lung cancer (e.g. non-small cell lung cancer), esophageal cancer, squamous cell carcinoma of the head and neck, liver cancer, ovarian cancer, cervical cancer, thyroid cancer, glioblastoma, glioma, leukemia, lymphoma, and other neoplastic malignancies. Additionally, the invention includes refractory or recurrent malignancies whose growth may be inhibited using the antibodies of the invention.

Antagonist antibody or antibody fragments of the invention can be used alone or in combination with: other anti-neoplastic agents or immunogenic agents (for example, attenuated cancerous cells, tumor antigens (including recombinant proteins, peptides, and carbohydrate molecules), antigen presenting cells such as dendritic cells pulsed with tumor derived antigen or nucleic acids, immune stimulating cytokines (for example, IL-2, IFNa2, GM-CSF), and cells transfected with genes encoding immune stimulating cytokines such as but not limited to GM-CSF); standard cancer treatments (for example, chemotherapy, radiotherapy or surgery); or other antibodies (including but not limited to antibodies to VEGF, EGFR, Her2/neu, VEGF receptors, other growth factor receptors, CD20, CD40, CTLA-4, OX-40, 4-IBB, PD-1, PD-L1, CTLA-4, ICOS, and other molecules in negative regulatory pathways).

Infectious Diseases

Antagonist antibody or antigen binding fragments of the invention (exemplified by hu Mab4C7) can also be used to prevent or treat infections and infectious disease. The antibody or antibody fragments can be used alone, or in combination with vaccines, to stimulate the immune response to pathogens, toxins, and self-antigens. The antibodies or antigen-binding fragment thereof can be used to stimulate immune response to viruses infectious to humans, such as, but not limited to, human immunodeficiency viruses, hepatitis viruses class A, B and C, Eppstein Barr virus, human cytomegalovirus, human papilloma viruses, herpes viruses. The antibodies or antigen-binding fragment thereof can be used to stimulate immune response to infection with bacterial or fungal parasites, and other pathogens.

Vaccination Adjuvant

Antagonist antibody or antigen binding fragments of the invention (exemplified by hu Mab4C7) can be used in conjunction with other recombinant proteins and/or peptides (such as tumor antigens or cancer cells) in order to increase an immune response to these proteins (i.e., in a vaccination protocol).

For example, in certain embodiments, anti-BTLA antagonist antibodies and antibody fragments thereof may be used to stimulate antigen-specific immune responses by coadministration of an anti-BTLA antibody with an antigen of interest (e.g., a vaccine). Accordingly, in another aspect the invention provides a method of enhancing an immune response to an antigen in a subject, comprising administering to the subject: (i) the antigen; and (ii) an anti-BTLA antibody of the invention or antigen-binding fragment thereof, such that an immune response to the antigen in the subject is enhanced. The antigen can be, for example, a tumor antigen, a viral antigen, a bacterial antigen or an antigen from a pathogen. Non-limiting examples of such antigens include, without limitation, tumor antigens, or antigens from the viruses, bacteria or other pathogens.

Th2 Mediated Diseases

In certain embodiments, anti-BTLA antagonist antibodies and antibody fragments of the invention (exemplified by hu Mab4C7) can also be used to treat Th2 mediated diseases, such as asthma and allergy. This is based on the finding that the antibodies of the invention can help induce a Th1 response. Thus, the antibodies of the invention can be used to in Th2 mediated diseases to generate a more balanced immune response.

Ex-Vivo Activation of T Cells

In certain embodiments, the antibodies and antigen fragments of the invention (exemplified by hu Mab4C7) can also be used for the ex vivo activation and expansion of antigen specific T cells and adoptive transfer of these cells into recipients in order to increase antigen-specific T cells against tumor. These methods may also be used to activate T cell responses to infectious agents such as CMV. Ex vivo activation in the presence of anti-BTLA antibodies may be expected to increase the frequency and activity of the adoptively transferred T cells.

Other Combination Therapies

As previously described, anti-BTLA antibodies of the invention can be coadministered with one or other more therapeutic agents, e.g., a cytotoxic agent, a radiotoxic agent, or an immunosuppressive agent. The antibody can be linked to the agent (as an immunocomplex) or can be administered separately from the agent. In the latter case (separate administration), the antibody can be administered before, after or concurrently with the agent or can be co-administered with other known therapies.

Antibodies and antigen binding fragments of the invention can also be used to increase the effectiveness of donor engrafted tumor specific T cells.

Many modifications and variations of this invention can be made without departing from its spirit and scope, as will be apparent to those skilled in the art. The invention is defined by the terms of the appended claims, along with the full scope of equivalents to which such claims are entitled. The specific embodiments described herein, including the following examples, are offered by way of example only, and do not by their details limit the scope of the invention.

General Methods

Standard methods in molecular biology are described (Maniatis, et al. (1982) *Molecular Cloning, A Laboratory Manual*, Cold Spring Harbor Laboratory Press, Cold Spring Harbor, N.Y.; Sambrook and Russell (2001) *Molecular Cloning*, 3$^{rd}$ ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology, Vols. 1-4*, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science, Vol. 1*, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science, Vol. 2*, John Wiley and Sons, Inc., New York; Ausubel, et al. (2001) *Current Protocols in Molecular Biology, Vol. 3*, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology, Vol. 1*, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology, Vol. 4*, John Wiley, Inc., New York).

Monoclonal, polyclonal, and humanized antibodies can be prepared (see, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol.* 165:6205; He, et al. (1998) *J. Immunol.* 160:1029; Tang et al. (1999) J. Biol. Chem. 274:27371-27378; Baca et al. (1997) *J. Biol. Chem.* 272:10678-10684; Chothia et al. (1989) *Nature* 342:877-883; Foote and Winter (1992) *J. Mol. Biol.* 224:487-499; U.S. Pat. No. 6,329,511).

An alternative to humanization is to use human antibody libraries displayed on phage or human antibody libraries in transgenic mice (Vaughan et al. (1996) *Nature Biotechnol.* 14:309-314; Barbas (1995) *Nature Medicine* 1:837-839; Mendez et al. (1997) *Nature Genetics* 15:146-156; Hoogenboom and Chames (2000) *Immunol. Today* 21:371-377; Barbas et al. (2001) *Phage Display: A Laboratory Manual*, Cold Spring Harbor Laboratory Press, Cold Spring Harbor, N.Y.; Kay et al. (1996) *Phage Display of Peptides and Proteins: A*

Laboratory Manual, Academic Press, San Diego, Calif.; de Bruin et al. (1999) Nature Biotechnol. 17:397-399).

Single chain antibodies and diabodies are described (see, e.g., Malecki et al. (2002) Proc. Natl. Acad. Sci. USA 99:213-218; Conrath et al. (2001) J. Biol. Chem. 276:7346-7350; Desmyter et al. (2001) J. Biol. Chem. 276:26285-26290; Hudson and Kortt (1999) J. Immunol. Methods 231:177-189; and U.S. Pat. No. 4,946,778). Bifunctional antibodies are provided (see, e.g., Mack, et al. (1995) Proc. Natl. Acad. Sci. USA 92:7021-7025; Carter (2001) J. Immunol. Methods 248: 7-15; Volkel, et al. (2001) Protein Engineering 14:815-823; Segal, et al. (2001) J. Immunol. Methods 248:1-6; Brennan, et al. (1985) Science 229:81-83; Raso, et al. (1997) J. Biol. Chem. 272:27623; Morrison (1985) Science 229:1202-1207; Traunecker, et al. (1991) EMBO J. 10:3655-3659; and U.S. Pat. Nos. 5,932,448, 5,532,210, and 6,129,914).

Bispecific antibodies are also provided (see, e.g., Azzoni et al. (1998) J. Immunol. 161:3493; Kita et al. (1999) J. Immunol. 162:6901; Merchant et al. (2000) J. Biol. Chem. 74:9115; Pandey et al. (2000) J. Biol. Chem. 275:38633; Zheng et al. (2001) J. Biol Chem. 276:12999; Propst et al. (2000) J. Immunol. 165:2214; Long (1999) Ann. Rev. Immunol. 17:875).

Purification of antigen is not necessary for the generation of antibodies. Animals can be immunized with cells bearing the antigen of interest. Splenocytes can then be isolated from the immunized animals, and the splenocytes can fused with a myeloma cell line to produce a hybridoma (see, e.g., Meyaard et al. (1997) Immunity 7:283-290; Wright et al. (2000) Immunity 13:233-242; Preston et al., supra; Kaithamana et al. (1999) J. Immunol. 163:5157-5164).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) J. Immunol. 146:169-175; Gibellini et al. (1998) J. Immunol. 160:3891-3898; Hsing and Bishop (1999) J. Immunol. 162:2804-2811; Everts et al. (2002) J. Immunol. 168:883-889).

Methods for flow cytometry, including fluorescence activated cell sorting (FACS), are available (see, e.g., Owens, et al. (1994) Flow Cytometry Principles for Clinical Laboratory Practice, John Wiley and Sons, Hoboken, N.J.; Givan (2001) Flow Cytometry, 2$^{nd}$ ed.; Wiley-Liss, Hoboken, N.J.; Shapiro (2003) Practical Flow Cytometry, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) Catalogue, Molecular Probes, Inc., Eugene, Oreg.; Sigma-Aldrich (2003) Catalogue, St. Louis, Mo.).

Standard methods of histology of the immune system are described (see, e.g., Muller-Harmelink (ed.) (1986) Human Thymus: Histopathology and Pathology, Springer Verlag, New York, N.Y.; Hiatt, et al. (2000) Color Atlas of Histology, Lippincott, Williams, and Wilkins, Phila, Pa.; Louis, et al. (2002) Basic Histology: Text and Atlas, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000) Bioinformatics 16: 741-742; Menne, et al. (2000) Bioinformatics Applications Note 16:741-742; Wren, et al. (2002) Comput. Methods Programs Biomed. 68:177-181; von Heijne (1983) Eur. J. Biochem. 133:17-21; von Heijne (1986) Nucleic Acids Res. 14:4683-4690).

Example 1

Fully Human BTLA Antibodies

Fully human monoclonal antibodies specific for human BTLA were generated using Medarex, Inc.'s UltiMAb antibody generation platform by immunizing mice with a combination of CHO cells overexpressing membrane-bound huBTLA and huBTLA-Fc fusion protein in MPL®+TDM adjuvant. Mice were immunized with BTLA-Fc fusion protein or cells expressing membrane-bound BTLA expressing mature extracellular domain (residues 31-152 of SEQ ID NO: 35). This sequence corresponds with the extracellular domain of transcript 1 variant described at GenBank Accession No. NP_861445 sequence (that matches human BTLA transcript 1 variant (NP_861445), with one amino acid difference in the intracellular domain at position 267 ((Pro267Leu, SEQ ID NO:35, encoded by SEQ ID NO:36) relative to NP_861445 (SEQ ID NO:37). After multiple rounds of immunization and serum titering, selected mice were chosen for fusion. One fusion produced 49 anti-BTLA Mabs most of which were of the IgG4 isotype. Another fusion produced 154 MAbs most of which were of the IgG1 isotype, including the Mab8D5.

Following human gamma/kappa screening, anti-BTLA Mabs were initially characterized and selected based on binding to BTLA-Ig by ELISA, FACS/FMAT screening on CHO/huBTLA and CHO parental cells to eliminate CHO positive Mabs, and for their ability to block HVEM binding to BTLA CHO cells. Relative affinity determinations were made using BIACore surface plasmon resonance analysis. The hu Mab8D5 binds equally well to both human and cynomolgus BTLA, but has no blocking activity. Hu Mab8D5 also demonstrated agonist activity in B- and T-cell functional assays as described herein.

Hu Mab8D5 is a fully human monoclonal antibody of the IgG4/kappa isotype (containing the stabilizing 228 proline mutation) that binds to human BTLA with approximately 2 nM affinity (BIAcore). The Hu Mab8D5 antibody is non-blocking and does not interfere with HVEM binding. Three additional antibodies, hu Mab8A3, hu Mab21H6, hu Mab19A7 exhibit similar, but not identical functional properties to those of hu Mab8D5. While hu Mab8A3 is also a non-blocking agonist antibody that does not interfere with HVEM binding, hu Mab21H6 and hu Mab19A7 are agonists that also block binding of HVEM with BTLA.

Anti-BTLA Antibody Isotype selection

Antibodies of the IgG4 isotype poorly bind complement C1q and therefore do not significantly activate complement. IgG4 antibodies also bind weakly to Fcγ receptors, leading to inefficient or absent antibody-dependent cell-mediated cytotoxicity (ADCC) (reviewed in Presta, 2002). The initially selected 8D5 IgG1 Mab was re-expressed as a human IgG4 containing the stabilizing Adair S228P mutation, to produce an anti-BTLA antibody that lacks effector function. The variable regions were subcloned into Ubiquitous Chromatin Opening Element (UCOE; Millipore, Billerica, Mass.) vectors, which contain the human kappa constant region and the human gamma 4 constant region with the S228P hinge mutation (Angal, 1993). Heavy and light chain expression vectors were linearized and cotransfected into CHO-S cells (Invitrogen, Carlsbad, Calif.) and stable clones were selected in CD CHO medium (Invitrogen, Carlsbad, Calif.) containing G418 and puromycin. Clones were screened for expression using a human gamma/kappa sandwich ELISA, and the best producing line was scaled up to 2 L for production and purification. The IgG4 version of the original 8D5 Mab is referred to herein as hu Mab8D5 (or hu Mab8D5 G4). The IgG1 version of 8D5 is referred to herein as hu Mab8D5 G1.

Anti-BTLA Antibody Sequences

Using degenerate primer PCR-based methods, the DNA sequence of heavy and light chain variable regions of the hu Mab8D5 and hu Mab4C7 sequences were determined. Total RNA was prepared from 5×10⁶ hybridoma cells using the RNeasy Mini Kit according to manufacturer's instructions (Qiagen, Valencia, Calif., USA). cDNA was prepared by the 5'-RACE protocol with the SMART RACE cDNA Amplification Kit (Clontech Laboratories, Inc., Mountain View, Calif., USA) and SuperScript II Reverse Transcriptase (Invitrogen, Carlsbad, Calif., USA), both according to manufacturer's instructions. The V-regions of each antibody were amplified using a 3' human-specific constant region primer, (VH primer HLB02 (SEQ ID NO:33); VK primer LY49 (SEQ ID NO:34)), paired with the 5' RACE universal primer mix. PCR products containing the V-region were cloned into the pCR4-TOPO vector (Invitrogen, Carlsbad, Calif., USA) and transformed into *E. coli* strain TOP10 (Invitrogen, Carlsbad, Calif., USA). Either miniprep DNA or Templiphi (GE Healthcare Biosciences, Piscataway, N.J., USA) were prepared, and subjected to DNA sequencing (Sequetech, Mountain View, Calif., USA). The resultant DNA sequences were analyzed for in-frame rearrangements and other antibody characteristics. Sequences of heavy and light chain variable regions of hu Mab8D5 are shown in FIGS. 1A-C. Complementarity determining regions (CDRs) are labeled. Sequence features are outlined in FIG. 1C. The sequences of heavy and light chain variable regions of the antagonist antibody Hu Mab4C7 are shown in FIGS. 2A-C.

Example 2

Anti-BTLA Antibody Binding Affinities

Figure 3B:
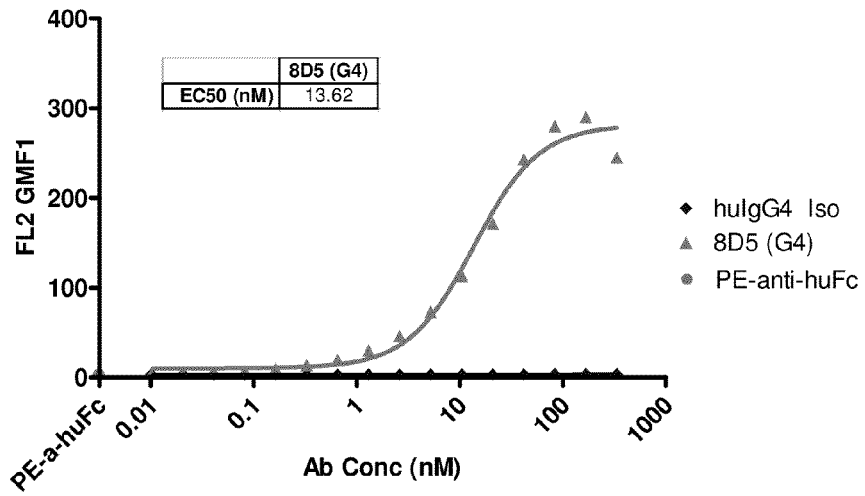
Figure 3C:
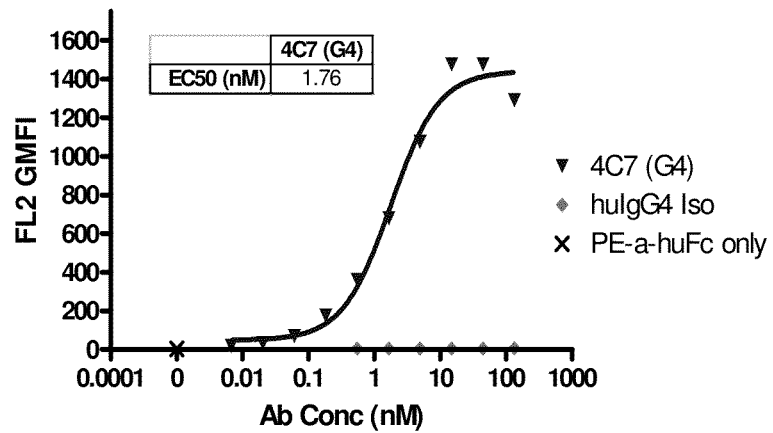
Figure 3D:
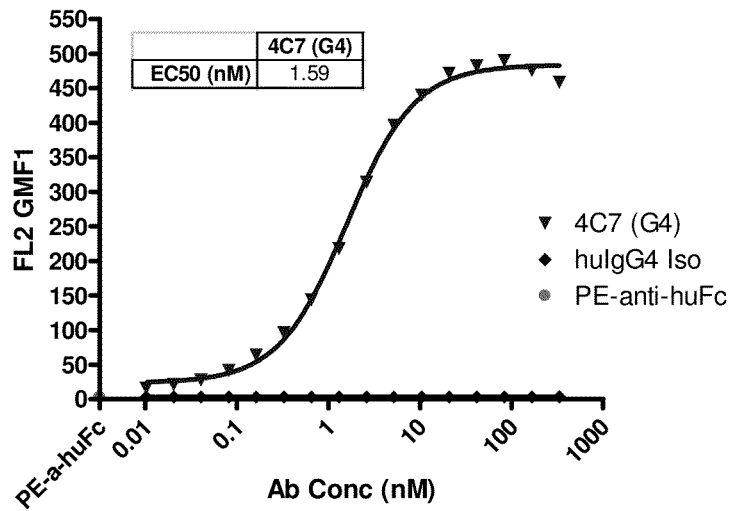

Cell-based flow cytometry was used to determine apparent binding affinities of hu Mab8D5 (FIGS. 3A-B) and hu Mab4C7 to human and cynomolgus BTLA (FIGS. 3C-D). Half-maximal binding of human and cynomolgus BTLA occurred at ~12 nM for both the IgG1 and IgG4 versions of hu Mab8D5. For agonist binding analysis (FIGS. 3A-B), hu Mab8D5 was titrated 3-fold from 20 µg/ml on CHO cells expressing human BTLA or 2-fold from 50 µg/ml on CHO cells expressing cynomolgus BTLA in 4° C. buffer containing 0.02% sodium azide to prevent receptor internalization. PE-anti-huFc was used for detection. This data illustrates that hu Mab8D5 binds to human and cynomolgus BTLA. Agonists huMab8A3, hu Mab21H6, and hu Mab19A7 exhibit similar binding affinities to that of hu Mab8D5.

TABLE 5

BIAcore Results

| Clone ID | $K_D \times 10^{-9}$ (M) | $k_{on} \times 10^4$ (1/Ms) | $k_{off} \times 10^{-4}$ (1/s) |
| --- | --- | --- | --- |
| 8D5 (G4) agonist | 2.99 | 4.58 | 1.37 |
| 21H6 (G1) | 5.50 | 5.11 | 2.82 |
| 8A3 (G1) | 9.27 | 2.88 | 5.96 |
| 19A7 (G1) | 20.7 | 2.88 | 5.96 |

For antagonist binding analysis (FIGS. 3C-D) hu Mab4C7 was titrated 3-fold from 20 µg/ml on CHO cells expressing human BTLA or 2-fold from 50 µg/ml on CHO cells expressing cynomolgus BTLA in 4° C. buffer containing 0.02% sodium azide to prevent receptor internalization. PE-anti-huFc was used for detection. For hu Mab4C7, half-maximal binding of human and cynomolgus BTLA occurred at ~1.6 nM for both the IgG1 and IgG4 versions of hu Mab4C7, as shown in FIGS. 3C-D. This data illustrates that hu Mab4C7 binds to human and cynomolgus BTLA.

Example 3

BIAcore

The antibodies were further profiled in order to elucidate binding kinetics and calculate equilibrium binding constants using BIAcore analysis demonstrating fast-on slow-off kinetics. For BIAcore, the test antibodies were captured on an anti-CH1 chip.

Hu Mab8D5 G4 exhibited an apparent Kd of 2.4 nM. The antagonist antibody hu Mab4C7 exhibited an apparent Kd of 4.6 nM.

TABLE 6

BIAcore Results

| HuMAb | Ka (1/Ms) * (10⁴) | $K_d$ (1/s) * (10⁻⁴) | $K_D$ (nM) |
| --- | --- | --- | --- |
| 8D5 (G4) agonist | 7.9 | 1.9 | 2.4 |
| 4C7 antagonist | 9.25 | 4.3 | 4.6 |

Example 4

HVEM Blocking Ability

The antibodies were tested to determine their ability to block the binding of HVEM to human BTLA. The ability to block the binding of HVEM to human BTLA was measured using a competitive cell-based flow cytometry assay. Serially diluted hu Mab8D5 was applied for 15 minutes to CHO cells expressing human BTLA (in buffer containing 0.02% sodium azide to prevent receptor internalization) prior to the addition of biotinylated human HVEM-Fc (R&D Systems; 1 µg/mL) for 30 minutes at 4° C. For the results shown in FIG. 4B, hu Mab8D5 was titrated 3 fold starting from 50 µg/ml and PE-SA was used for detection.

Figure 4A:
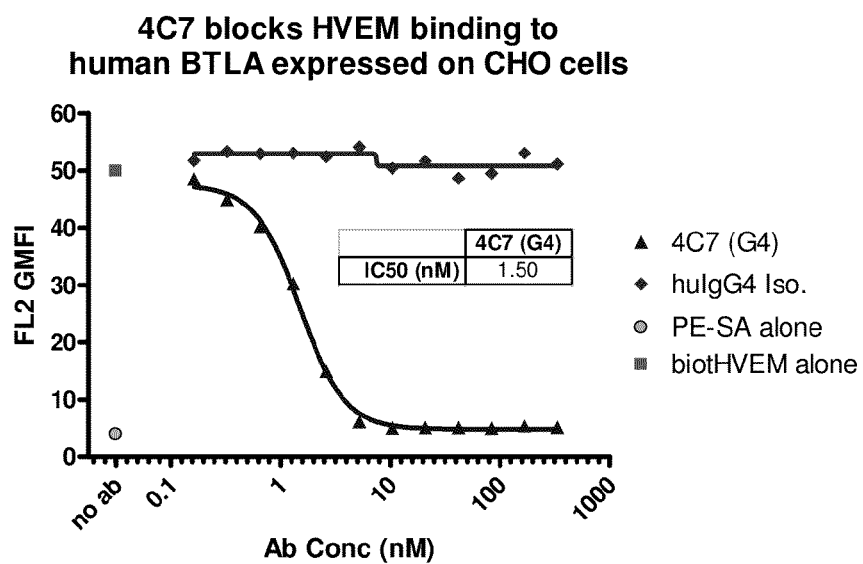
FIGS. 4A-B show the results of testing the ability of the antibodies to block human HVEM binding to CHO cells expressing human BTLA.

The HVEM blocking ability of hu Mab4C7 is shown in FIG. 4A from the same assay. Serially diluted hu Mab4C7 was applied for 15 minutes to CHO cells expressing human BTLA (in buffer containing 0.02% sodium azide to prevent receptor internalization) prior to the addition of biotinylated human HVEM-Fc (R&D Systems; 1 µg/mL) for 30 minutes at 4° C. For the results shown in FIG. 4A, hu Mab4C7 was titrated 3 fold starting from 50 µg/ml and PE-SA was used for detection. Washed cells were resuspended in 4° C. buffer containing propidium iodide (PI) as well as 0.02% sodium azide to prevent receptor internalization and analyzed by flow cytometry. Live cells were gated based on exclusion of PI-positive cells from the FSC/SSC gate and their geometric mean fluorescence was measured. The results in FIG. 4A show hu Mab4C7 blocks human HVEM (hHVEM) binding to CHO cells expressing hBTLA.

Figure 4B:
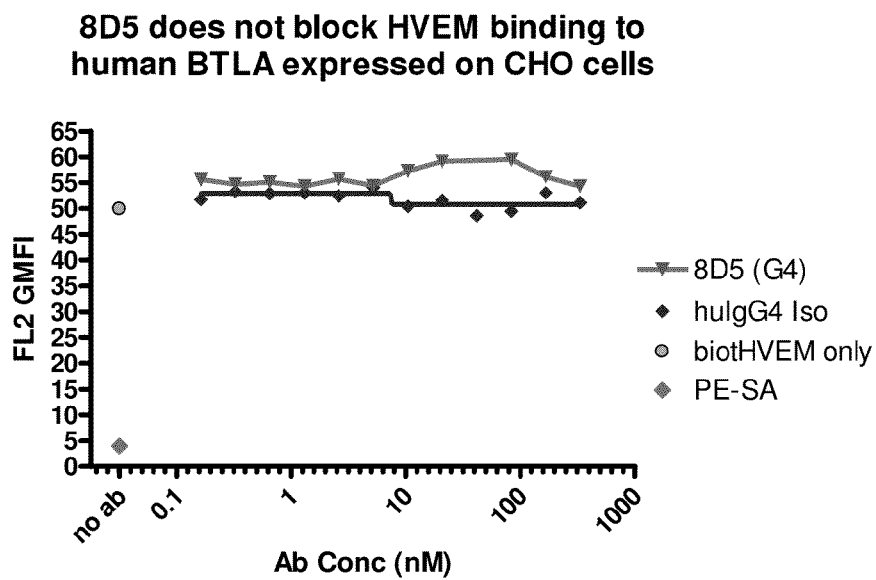

As shown in FIG. 4B, hu Mab8D5 does not inhibit or compete with binding of HVEM to human BTLA. Similar results were obtained for antibody huMab8A3. As shown in FIG. 4A, huMAb4C7 inhibits or competes with binding of HVEM to human BTLA. Similar blocking results were obtained for antibodies hu Mab21H6, hu Mab19A7.

Example 5

Human T Cell Response to CD3 Cross-Linking is Inhibited by hu Mab8D5

Anti-BTLA agonist antibodies and antibody fragments were tested for their capacity to decrease T cell activity in vitro using blood cells from healthy volunteers stimulated in various settings. A classical T cell stimulation assay was utilized that employs anti-CD3 Mab to cross-link the T cell receptor complex on the cell surface of all competent human T cells.

T cell blasts were generated in culture from human PBMCs using PHA and IL-2. Blasts were stimulated with immobilized anti-CD3 Abs for 48 hours in the presence or absence of soluble hu Mab8D5, hu Mab8D5 Fab fragment or IgG1 isotype control. Proliferation was measured by thymidine incorporation as shown in FIG. 5.

Figure 5:
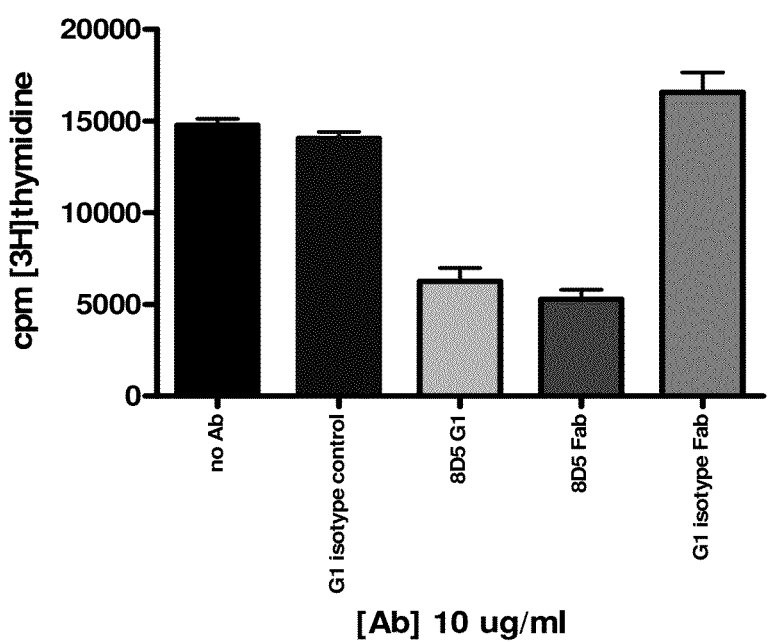
FIG. 5 is a graph showing that hu Mab8D5, as well as hu Mab8D5 Fab' fragment, inhibits anti-CD3 induced proliferation of human T cell blasts.

In this assay, hu Mab8D5 was demonstrated to inhibit proliferation suggesting that the outcome of concurrent stimulation of the antigen receptor and BTLA on T cells is suppression of T cell response (FIG. 5). The hu Mab8D5 antibody added to these cultures as monovalent Fab' fragments demonstrated similar activity, which strongly indicates that hu Mab8D5 activates BTLA receptor function by hitting a functional epitope, and not by cross-linking of multiple BTLA molecules on the cell surface. This data illustrates that hu Mab8D5 inhibits anti-CD3 induced proliferation of human T cell blasts.

Example 6

Human T Cell Response to SEB is Inhibited by hu Mab8D5 and Increased by hu Mab4C7

Another assay used to characterize the functional consequence of activating the BTLA receptor employs *Staphylococcus* enterotoxin B (SEB) to engage and activate all human T cells expressing the Vβ3, Vβ12, Vβ14, Vβ17 and some other T cell receptor chains, depending on the dose of SEB. Depending on the donor, SEB activates up to 20% of all T cells determined by IL-2 production.

In the present analyses, healthy human (FIG. 6A) or cynomolgus monkey donor blood (FIG. 6B) was diluted 1:10 and pre-incubated with antibodies before adding superantigen SEB (1 μg/ml) to the culture. Human IgG4 (HuIgG4) is the isotype control Mab for hu Mab8D5. A single representative human and monkey donor are shown.

After 2 days, IL-2 production was measured by ELISA. Hu Mab8D5 decreased IL-2 production compared to control human IgG4 in both human and monkey donors.

Figure 6A:
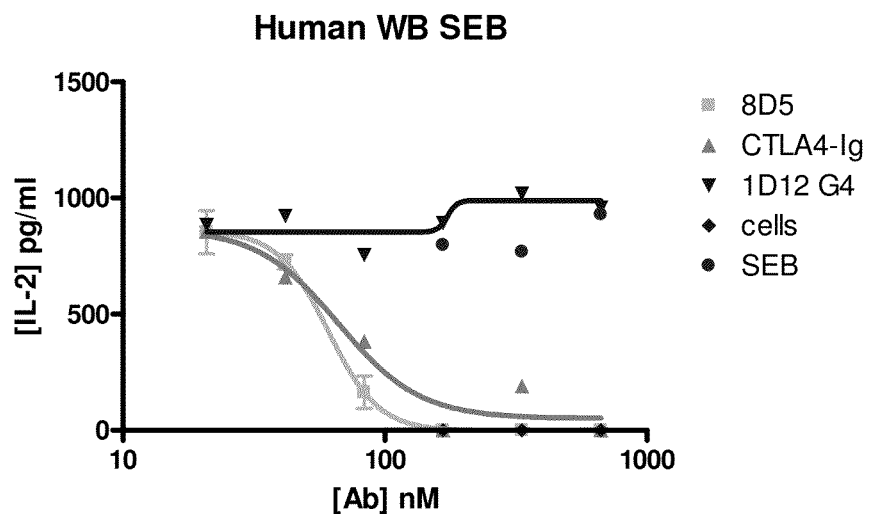
FIGS. 6A-D are graphs showing the effects of hu Mab8D5 and hu Mab4C7 on SEB-induced human and cyno monkey T-cell response.
Figure 6B:
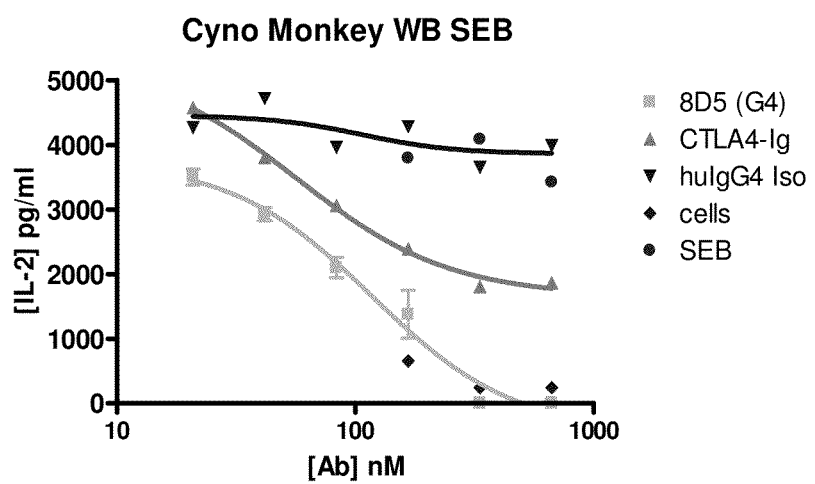
Figure 6C:
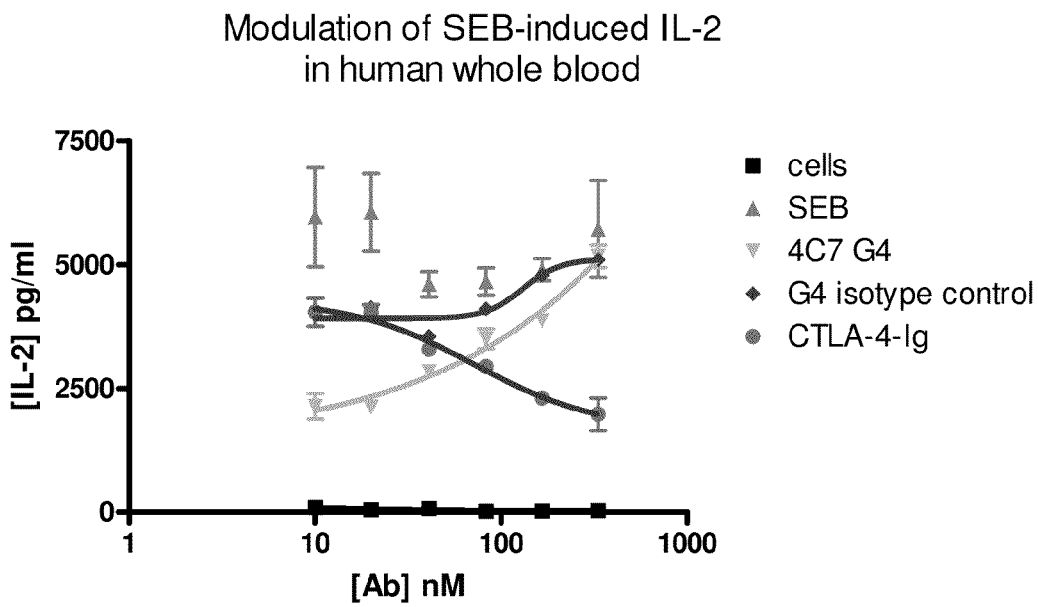

The soluble CTLA-4-Ig fusion protein (CTLA-4/Ig), which blocks the interaction between the costimulatory receptor CD28 and its ligands CD80/CD86, decreased the SEB-induced IL-2 production, further validating the SEB stimulation assay as a method to quantify T cell activity after manipulation of costimulatory pathways. The decrease in IL-2 production by the tested agonist anti-BTLA antibodies was found to be dose-dependent (FIGS. 6A-B). Antibodies hu Mab8A3, hu Mab21H6, hu Mab19A7 may also have similar effects on IL-2 production.

Figure 6D:
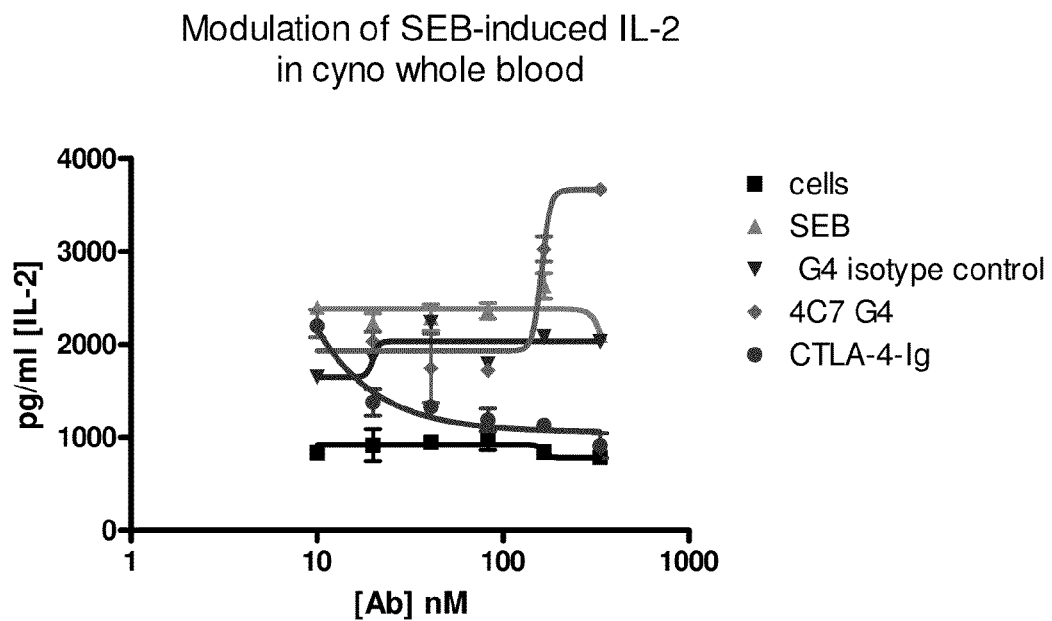

These assays were also conducted with hu Mab4C7, according to the methods described above. Hu MAb4C7, in contrast to CTLA-4/Ig and hu Mab8D5, increased IL-2 production compared to control human IgG4 in both human (FIG. 6C) and monkey donors (FIG. 6D).

The ability of the tested anti-human BTLA Mabs to cross-react with monkey BTLA is especially useful in testing for the ability of the Mabs to modulate T cell responses in well-tested models such as monkey kidney transplant and EAE systems, which are indicative of disease modulation in vivo. The ability of the tested agonist anti-BTLA antibodies to decrease IL-2 production in the SEB stimulation assay indicates that these antibodies would be suitable for controlling or preventing conditions such as graft versus host disease.

Example 7

Inhibition of Tetanus Toxoid (TT) Dependent IFNγ Production and Proliferation by hu Mab8D5 in Blood Cells from TT-Vaccinated Donors Additionally, it was examined whether the ability of anti-BTLA treatment suppressed an antigen-specific response using the tetanus toxoid (TT) recall antigen. TT was added to PBMCs at 0.1 μg/ml, cytokine and proliferation were analyzed after 7 days. PBMC from recently TT vaccinated individuals were restimulated in vitro for 7 days using TT in the presence or absence of Abatacept (CTLA-4/Ig), hu Mab8D5, or control isotype antibody IgG4. Interferon gamma (IFN γ) production was measured by ELISA and proliferation was measured by tritiated thymidine incorporation.

Figure 7A:
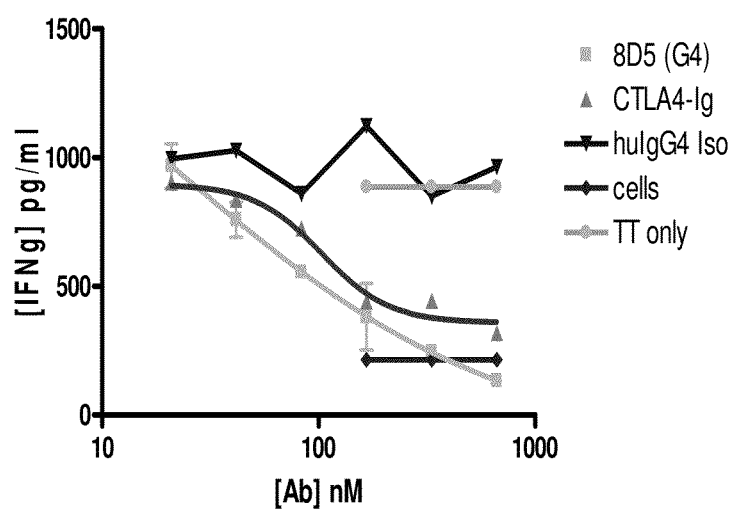
FIGS. 7A-B are graphs showing that human recall T cell response to tetanus toxoid challenge is decreased by hu Mab8D5.
Figure 7B:
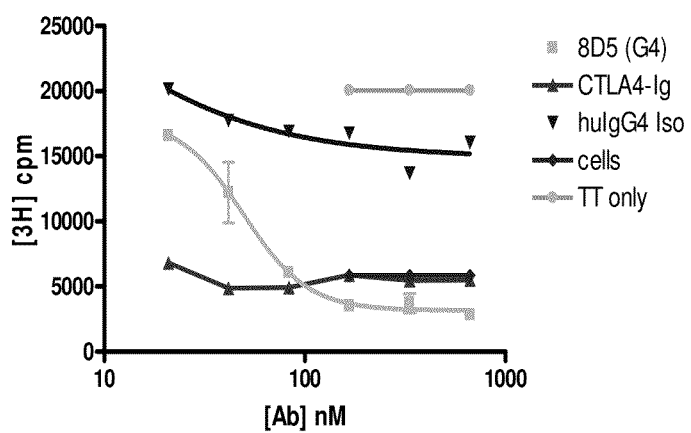
Figure 8A:
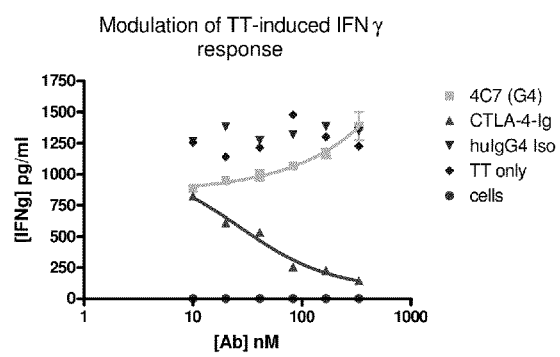
FIGS. 8A-B are graphs showing that human recall T cell response to tetanus toxoid challenge is increased by hu Mab4C7.
Figure 8B:
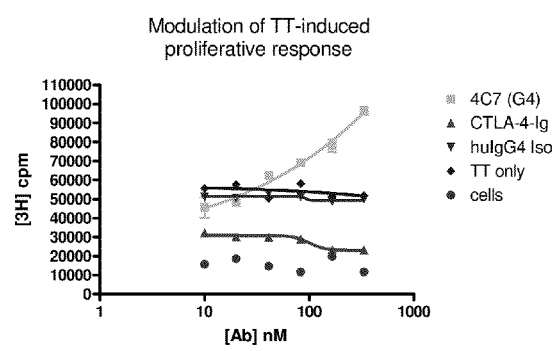

TT-induced IFNγ production (FIG. 7A) and proliferation (FIG. 7B) were markedly reduced by CTLA-4/Ig and by hu Mab8D5 compared to antigen alone. These data indicate that hu Mab8D5 is capable of inhibiting T cell responses triggered through the (antigen-specific) T cell receptor complex. Both primary and secondary (recall) responses are suppressed in the presence of hu Mab8D5.

Example 8

Increase in Tetanus Toxoid (TT) Dependent IFNγ Production and Proliferation by hu Mab4C7 in Blood Cells from TT-Vaccinated Donors The IFNγ production (FIG. 8A) and proliferation analyses (FIG. 8B) were also carried out, as described above, using the antagonist antibody hu Mab4C7. TT-induced IFNγ production (FIG. 8A) and proliferation (FIG. 8B) were markedly increased by hu Mab4C7 compared to antigen alone. These results indicate that hu Mab4C7 is capable of increasing T cell responses triggered through the antigen-specific T cell receptor complex. Both primary and secondary (recall) responses are increased in the presence of hu Mab4C7.

Example 9

Human B Cell Function is Inhibited by hu Mab8D5

Figure 9:
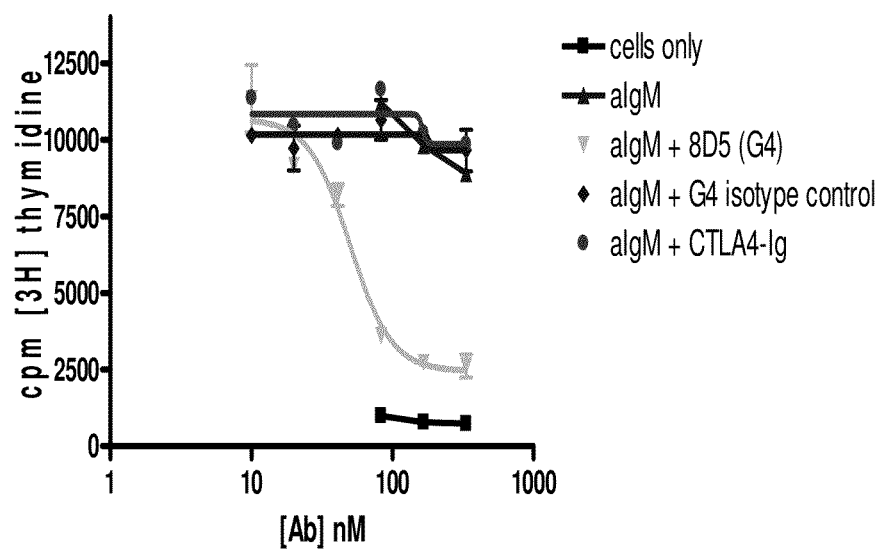
FIG. 9 is a graph showing that human B cell function is inhibited by hu Mab8D5.

Human B cells were isolated from peripheral blood and stimulated with anti-IgM in the presence or absence of anti-BTLA Mabs. Specifically, B cells were isolated by negative selection from human whole blood and stimulated with 10 μg/ml of anti-IgM F(ab')$_2$ fragments in the presence or absence of hu Mab8D5, CTLA-4/Ig or isotype control. Proliferation was measured by thymidine incorporation after 48h. Hu Mab8D5 produced a dose-dependent decrease in B cell proliferation, while an isotype control and CTLA-4/Ig had no effect, as shown in FIG. 9. Similar results were obtained for antibody huMab8A3.

Example 10

Inhibition of Peripheral Blood B Cell Chemokine Production by hu Mab8D5

Figure 10A:
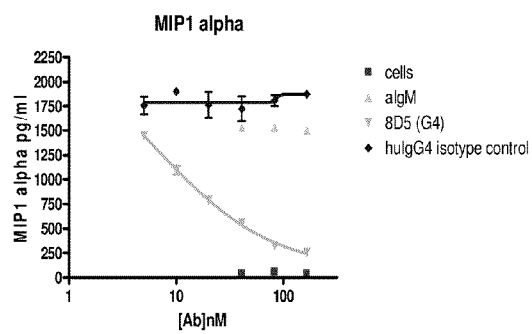
FIGS. 10A-B are graphs showing the inhibition of peripheral blood B cell chemokine production by hu Mab8D5.
Figure 10B:
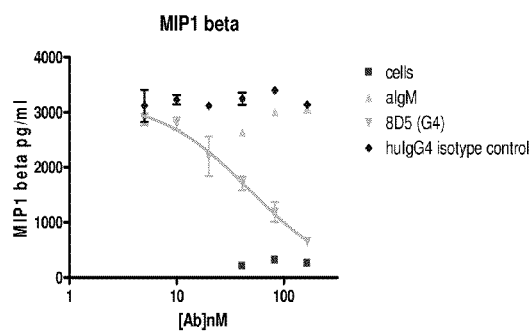

Cross-linking of surface IgM on naïve B cells leads to enhanced production of chemokines such as MIP1α and MIP1β. FIGS. 10A-B represent graphs showing the inhibition of peripheral blood B cell chemokine production by hu Mab8D5. B cells were isolated by negative selection from human whole blood and stimulated with 10 μg/ml of anti-IgM F(ab')$_2$ fragments in the presence or absence of hu Mab8D5 or isotype control. MIP1 α and β production were measured by ELISA.

In addition to limiting B cell proliferation, hu Mab8D5 reduced chemokine production of MIP1α (FIG. 10A) and MIP1β (FIG. 10B) of anti-IgM triggered B cells in a dose-dependent fashion. Importantly, hu Mab8D5 and control antibodies were tested in experiments using non-antigen-specific triggers, such as CD40L plus IL-4, which potently induce B cell proliferation without engaging the B cell receptor. Under these conditions, no activity of hu Mab8D5 was detected.

Example 11

Hu Mab8D5 does not Autonomously Elicit Immune Activity

Figure 11:
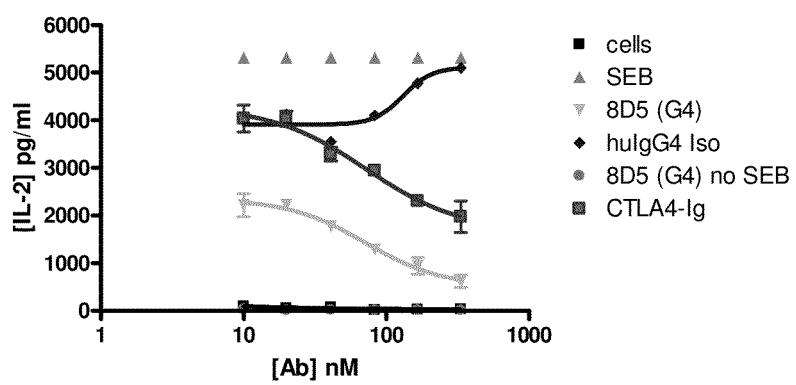
FIG. 11 is a graph showing that hu Mab8D5 does not autonomously stimulate immune activity in healthy donor blood.

FIG. 11 is a graph showing that hu Mab8D5 does not autonomously stimulate immune activity in healthy donor blood. Diluted whole blood from humans was stimulated with the superantigen SEB in the presence or absence of hu Mab8D5 or CTLA-4-Ig. HuIgG4 is the isotype control mAb for hu Mab8D5. Hu Mab8D5 was also added to blood in the absence of SEB stimulation. After 48 hours (h), IL-2 production was measured by ELISA.

In the TT recall response assays, as well as in the SEB stimulation assays (using human whole blood), hu Mab8D5 does not stimulate detectable proliferation or cytokine responses without concurrent specific stimulation of the T cell receptor. This demonstrates that hu Mab8D5 is not likely to induce inadvertent cytokine storm-like events in patients.

Example 12

Hu Mab8D5 Triggers BTLA Inhibitory Signaling Activity

Hu Mab8D5 and hu Mab4C7 immuno-precipitates BTLA protein from B cells, and pretreatment with hu Mab8D5 reduces TCRξ phosphorylation. Lysates from human peripheral blood B cells were immuno-precipitated with various BTLA HuMAbs. huIgG4 is an isotype control, hu Mab4C7 (an antagonist antibody), and 2G9, are other BTLA HuMAbs. For FIG. 12B, CD4 T cells were isolated from peripheral blood and treated as follows: Lane 1=unstimulated cells, Lane 2=stimulated for 30 min with anti-CD3 T cell expander beads, Lane 3=treated with 25 μg/ml hu Mab8D5-(labeled as clone 8D5) prior to 30 min. stimulation with expander beads. Top blot of whole cell lysates is probed for total CD3ξ, while bottom blot is probed with a phospho-specific CD3ξ Ab. M lane is molecular weight markers, numbers indicated kD.

In peripheral blood B cells derived from healthy donors, hu Mab8D5 and hu Mab4C7 were shown to specifically bind to and immunoprecipitate BTLA (FIG. 12A). In peripheral blood CD4+ T cells stimulated with anti-CD3 plus anti-CD28, pre-incubation with hu Mab8D5 was found to reduce phosphorylation of the TCRξ chain, which is critical for initiation of TCR/CD3 signaling (FIG. 12B).

Example 13

Hu Mab8D5 is Active as a Monovalent Fab'

Figure 13A:
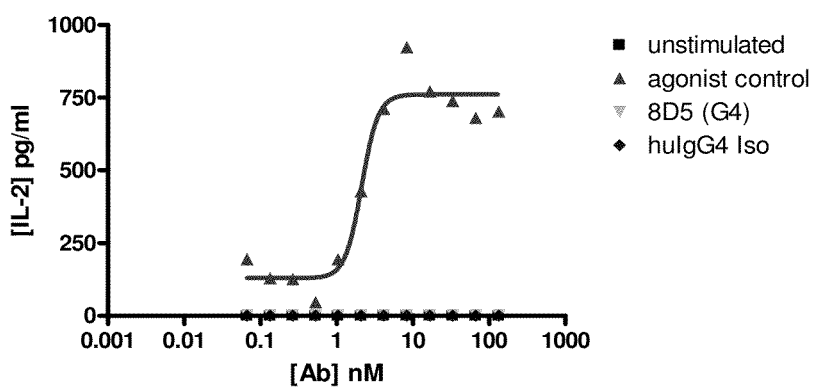
FIGS. 13A-B are graphs showing that hu Mab8D5 suppressed SEB response and B cell proliferation in a dose dependent manner.
Figure 13B:
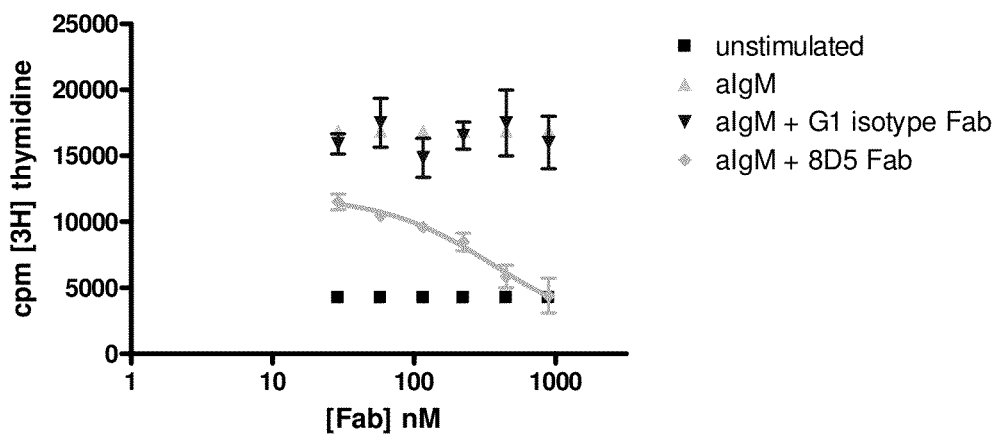

For FIG. 13A, diluted whole blood from humans was stimulated with the superantigen SEB in the presence or absence of hu Mab8D5 Fab or isotype control Fab for hu Mab8D5. After 48h, IL-2 production was measured by ELISA. For FIG. 13B, B cells were isolated by negative selection from human whole blood and stimulated with 10 μg/ml of anti-IgM F(ab')$_2$ fragments in the presence or absence of hu Mab8D5 Fab or isotype control Fab. Proliferation was measured by thymidine incorporation after 48h. FIGS. 13A-B illustrate that hu Mab8D5 suppressed SEB response and B cell proliferation in a dose dependent manner.

As described herein, the hu Mab8D5 was found to trigger BTLA activity when added to T or B cell cultures as a monovalent Fab'. The relative potency (but not the relative efficacy) of the Fab' was approximately 10-fold less than that of the full Mab which suggests that loss of potency was merely due to loss of avidity. Hu Mab8D5 as a Fab' fragment was able to dose-dependently suppress both an SEB response in human whole blood and anti-IgM-induced B cell proliferation (FIGS. 13A-B). Like other Ig-fold cell surface receptors, BTLA immune suppressive activity could also be triggered when any BTLA binding antibody was coated onto plastic (through cross-linking of multiple receptors). However, the fact that monovalent binding of hu Mab8D5 to BTLA appears to fully activate the inhibitory function seems to be a unique feature of BTLA (e.g. that is not shared with negative costimulatory protein family members PD-1 or CTLA-4). Since hu Mab8D5 does not impede binding of HVEM, the natural ligand of BTLA, while not wishing to be bound by theory, this indicates that hu Mab8D5 hits an (potentially allosteric) epitope on the extracellular domain of BTLA inducing a conformational change and subsequent intracellular signaling.

Example 14

Cytokine Storm

Figure 14A:
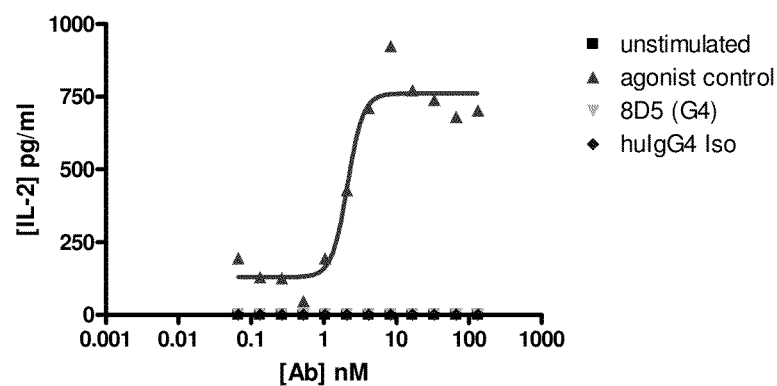
FIGS. 14A-D are graphs illustrating that the tested anti-BTLA agonist antibodies do not elicit a cytokine storm in human PBMC cultures, as measured by the lack of production of IL-2 (FIGS. 14A, B), IFNγ (FIG. 14C), and TNFα (FIG. 14D) in human PBMC cultures.
Figure 14B:
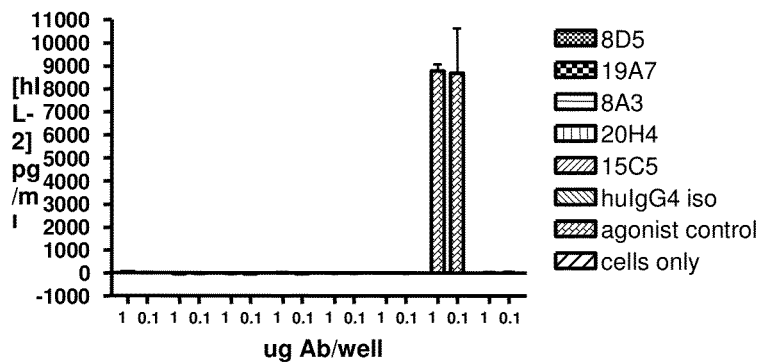
Figure 14C:
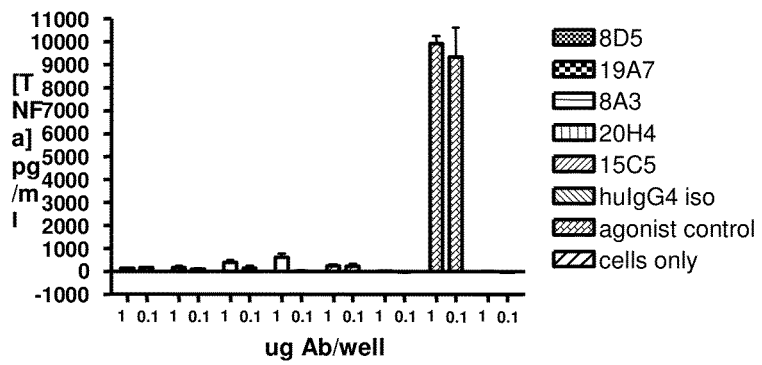
Figure 14D:
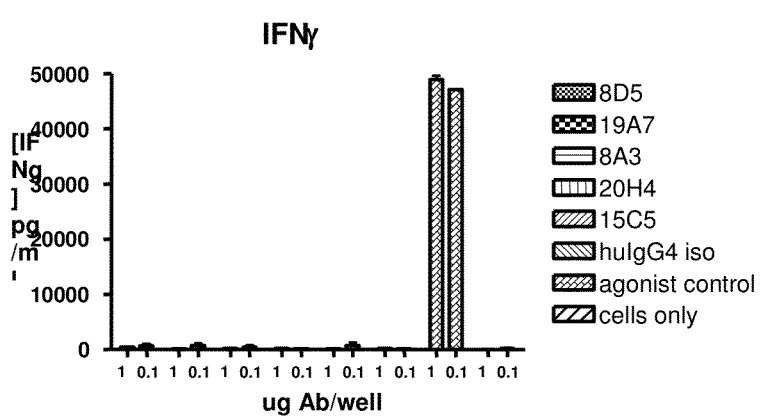
Figure 15:
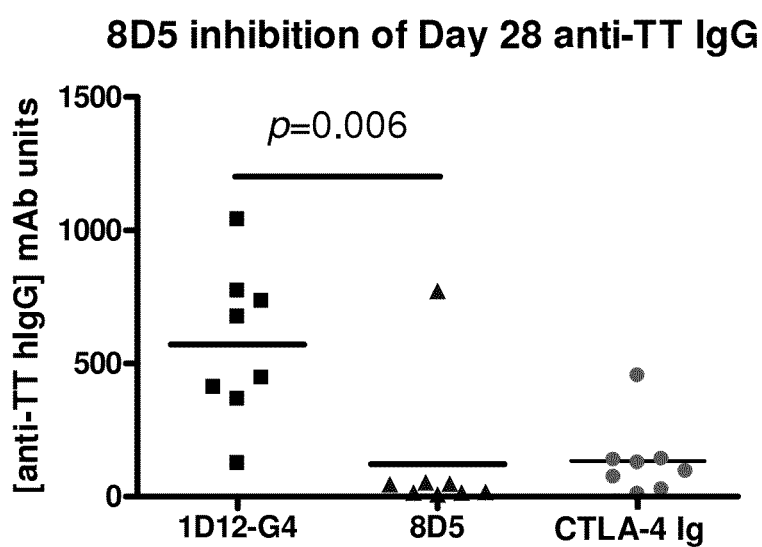
FIG. 15 is a graph of day 28 ELISA results showing that hu Mab8D5 inhibited human anti-TT recall IgG response in SCIDhu SPL mice.
Figure 16:
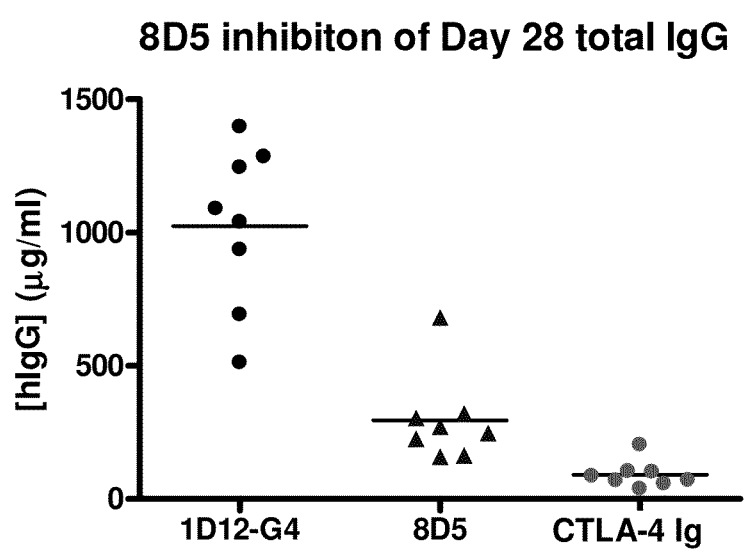
FIG. 16 is a graph of day 28 ELISA results showing that hu Mab8D5 inhibited human total IgG response in SCIDhu SPL mice.

BTLA is an immunomodulatory receptor of the CD28 family. A potential complication of utilizing an agonist antibody is induction of "cytokine storm" activity in vivo. Cytokine storm is a systemic inflammatory response characterized by a rapid induction of proinflammatory cytokines due to an interruption of the positive feedback loop between cytokines and immune cells. Procedures to improve predictive preclinical safety testing of immunomodulatory therapeutics have been developed (e.g., by the National Institute for Biological Standards and Control, UK, See, Stebbings, 2007). In vitro testing of hu Mab8D5, utilizing current models and methodology to predict the potential for cytokine storm in vivo has been performed. The cytokine storm assays were conducted using purified positive cytokine storm control agonist antibody as the positive reference. In these assays, immobilized positive control agonist mAb produced a robust IL-2 response in the absence of additional stimulation. When immobilized in the same manner, neither hu Mab8D5 nor control IgG4 induced IL-2 secretion, as shown in FIGS. 14A-B. FIGS.

14B-D, illustrate that agonist antibodies hu Mab8D5, hu Mab8A3, hu Mab15C5, hu Mab20H4, and hu Mab19A7 also did not elicit production of the inflammatory cytokines interferon gamma (IFNγ) and tumor necrosis factor alpha (TNFα) when supercrosslinked (under conditions as described above). The positive control agonist mAb, in contrast, produced both an IFNγ and TNFα response. Thus, none of the tested anti-BTLA agonist antibodies elicited a cytokine storm in human PBMC cultures, and likewise they would not be expected to elicit a cytokine storm in vivo, based on the results in this in vitro reference model.

As demonstrated in Example 11 and FIG. 11, hu Mab8D5 does not autonomously stimulate immune function in any of the functional assays employed. Addition of hu Mab8D5 in the absence of T cell specific triggering does not result in measurable changes in cytokine secretion or proliferation. Furthermore, in tests forcing higher level cross-linking by coating hu Mab8D5 onto plastic, the mAb did not induce cytokine release or proliferation. Based on these data, the inhibitory nature of the BTLA-HVEM interaction, and the fact that triggering BTLA incurs inhibitory intracellular signaling, the potential risk of a cytokine storm is considered highly unlikely.

Example 15

Tolerability and Side Effects in Animal Models

There were no tolerability issues or side effects noted in any animal studies with hu Mab8D5 or hu Mab4C7.

Example 16

Effects of 8D5 in SCIDhu SPL—A Human Immune Response Model

In order to determine whether HuMab anti-BTLA agonist IgG4 clone 8D5 can inhibit human T cell dependent mediated B cell IgG production in the SCIDhu SPL model of human immune response was used to probe the potential of HuMabs to modulate immune responses in vivo. CTLA-4-Ig was used as a control because it is an immunosuppressant that reduces T-cell responses and is known to affect T-cell dependent antibody production by B cells.

Briefly, SCID mice were engrafted i.p. with human spleen cells, immunized with 100 μg tetanus toxoid and treated with 200 μg target specific or control antibodies on days 0, 5, 9 and 14. Mice were boosted with TT on day 7. On Day 28 the mice were euthanized, sera were collected and peritoneal exudate cells (PEC) were harvested. PEC were analyzed by FACS for lymphocyte subset marker expression to evaluate Ab treatment effects on relative cell numbers. TT-specific and total human IgG concentrations in day 28 sera were quantified by ELISA.

Figure 17A:
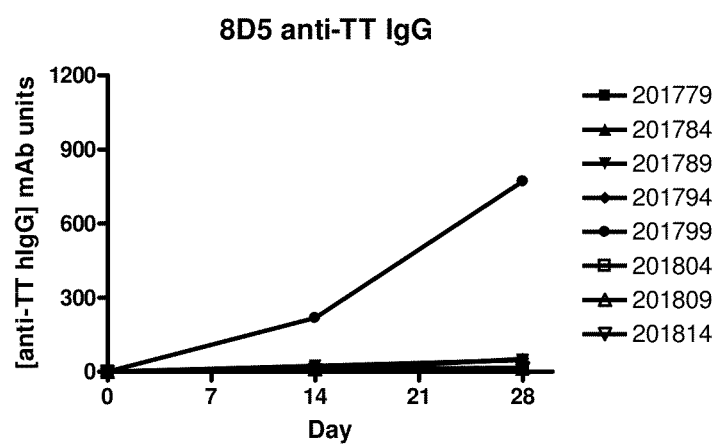
FIGS. 17A-B are graphs showing titers from individual treated mice illustrating that hu Mab8D5 inhibited human anti-TT recall IgG response in SCIDhu SPL mice (FIG. 17A), compared to isotype control (FIG. 17B).
Figure 17B:
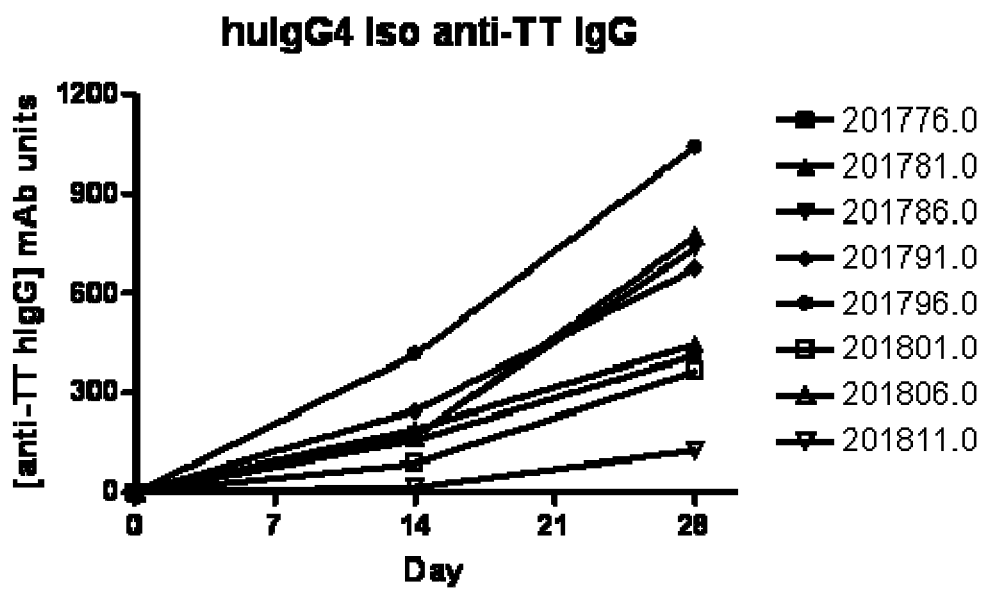
Figure 18A:
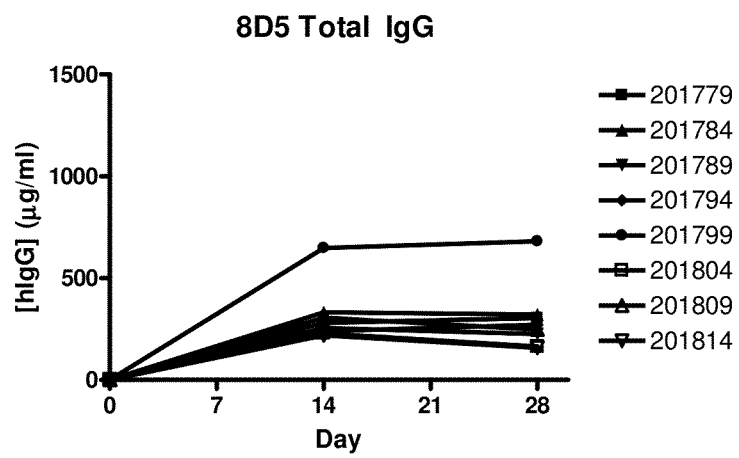
FIGS. 18A-B are graphs showing titers from individual treated mice illustrating that hu Mab8D5 inhibited human total IgG response in SCIDhu SPL mice (FIG. 18A) compared to isotype control (FIG. 18B).
Figure 18B:
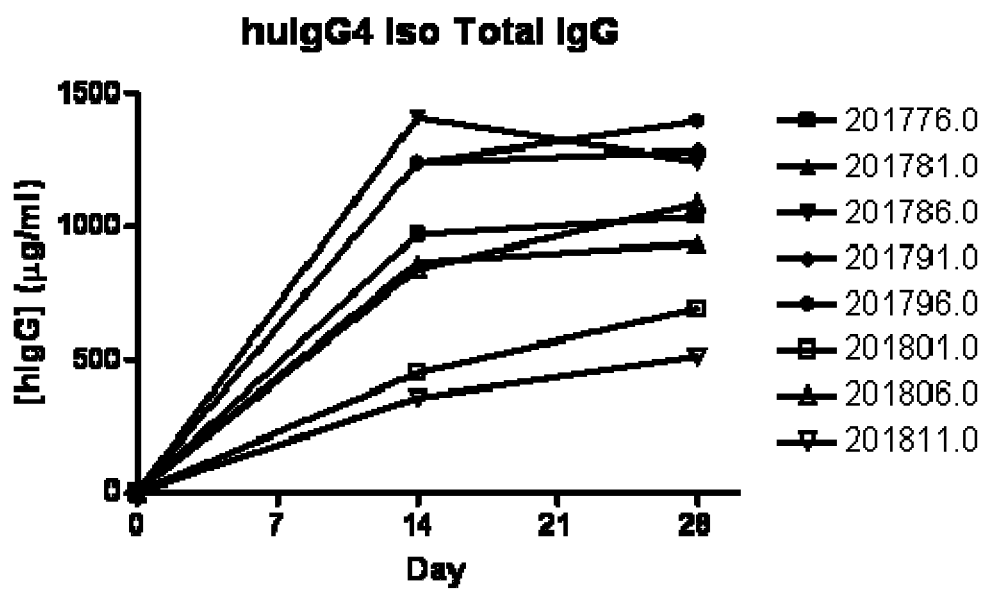

ELISA of Day 28 sera showed that hu MAb8D5 inhibited human anti-TT recall and total IgG responses in SCIDhu SPL mice (FIGS. 15, 16, 17A & 18A) compared to the isotype control huIgG4 (FIGS. 17B & 18B). Anti-BTLA hu MAb8D5 displayed similar efficacy as CTLA-4-Ig for lowering total and TT-specific IgG titers compared to isotype control huIgG4 treated mice. FIGS. 17A, 17B, 18A, and 18B show plots of the titers from individual treated mice. In summary, these data are consistent with hu MAb8D5 behaving as an agonist of BTLA and that hu MAb8D5-induced BTLA signaling inhibits human T cell activation, expansion and subsequent T cell dependent recall Ag specific and total IgG production by human B cells.

Example 17

SCID-RA Synovium Model

The SCID-RA synovium model involves transplantation of synovium from RA-patients to immune-deficient SCID mice to create a humanized mouse model for RA. RA synovial grafts can persist in SCID mice and maintain the morphology and characteristics of the RA joint, including synovial hyperplasia, inflammation, immune reactivity and angiogenesis. RA synovium are obtained from joint replacement surgery (e.g. hip, knee, shoulder). The SCID immuno-deficient mice have no functional T and B cells and exhibit no graft rejection.

Synovium are collected during surgery and directly processed into small pieces (biopsies of 6 mm). Synovium samples are freshly transplanted to SCID-mice into so-subcutaneous pockets on the back. After a 7 day engraftment period, IP injections of control or treatment/test antibodies are given on days 7 and 10. On day 14, mice are sacrificed, blood and synovia are collected. Analyses include serum cytokine ELISA, H+E staining and serum antibody quantification.

SEQUENCE INDEX

TABLE 7

| SEQ ID NO: | Description |
|---|---|
| 1 | cDNA sequence encoding human BTLA isoform; Accession No. AY293286 |
| 2 | Amino acid sequence of Human BTLA Accession No. AAP44003 |
| 3 | Mouse BTLA nucleotide sequence (Accession No. AY293285) |
| 4 | Mouse BTLA amino acid sequence (Accession No. AAP44002) |
| 5 | anti-BTLA 8D5 VH CDR1 |
| 6 | anti-BTLA 8D5 VH CDR2 |
| 7 | anti-BTLA 8D5 VH CDR3 |
| 8 | anti-BTLA 8D5 VH, nucleotide sequence including leader sequence |
| 9 | anti-BTLA 8D5 VH amino acid sequence including leader sequence |
| 10 | anti-BTLA 8D5 VH, nucleotide sequence without leader sequence |
| 11 | anti-BTLA 8D5 VH, amino acid sequence without leader sequence |
| 12 | anti-BTLA 8D5 $V_K$ CDR1 |
| 13 | anti-BTLA 8D5 $V_K$ CDR2 |
| 14 | anti-BTLA 8D5 $V_K$ CDR3 |
| 15 | anti-BTLA 8D5 $V_K$, nucleotide sequence including leader sequence |
| 16 | anti-BTLA 8D5 $V_K$ amino acid sequence including leader sequence |
| 17 | anti-BTLA 8D5 $V_K$, nucleotide sequence without leader sequence |
| 18 | anti-BTLA 8D5 $V_K$, amino acid sequence without leader sequence |
| 19 | anti-BTLA 4C7 VH CDR1 |
| 20 | anti-BTLA 4C7 VH CDR2 |
| 21 | anti-BTLA 4C7 VH CDR3 |
| 22 | anti-BTLA 4C7 VH, nucleotide sequence including leader sequence |
| 23 | anti-BTLA 4C7 VH amino acid sequence including leader sequence |
| 24 | anti-BTLA 4C7 VH, nucleotide sequence without leader sequence |
| 25 | anti-BTLA 4C7 VH, amino acid sequence without leader sequence |
| 26 | anti-BTLA 4C7 $V_K$ CDR1 |
| 27 | anti-BTLA 4C7 $V_K$ CDR2 |
| 28 | anti-BTLA 4C7 $V_K$ CDR3 |
| 29 | anti-BTLA 4C7 $V_K$, nucleotide sequence including leader sequence |
| 30 | anti-BTLA 4C7 $V_K$ amino acid sequence including leader sequence |
| 31 | anti-BTLA 4C7 $V_K$, nucleotide sequence without leader sequence |
| 32 | anti-BTLA 4C7 $V_K$, amino acid sequence without leader sequence |
| 33 | HLB02 sequencing primer |
| 34 | LY49 sequencing primer |

TABLE 7-continued

| SEQ ID NO: | Description |
|---|---|
| 35 | Human BTLA amino acid sequence |
| 36 | Human BTLA nucleotide sequence |
| 37 | Human BTLA amino acid sequence Accession No. NP_861445 |
| 38 | 8D5 VH CDR1 variants |
| 39 | 8D5 CDR3 variants |
| 40 | 8D5 $V_K$ CDR2 variants |
| 41 | 8D5 $V_K$ CDR3 variants |
| 42 | 4C7 VH CDR2 variants |
| 43 | 4C7 VH CDR3 variants |
| 44 | anti-BTLA 21H6 VH nucleotide sequence |
| 45 | anti-BTLA 21H6 VH amino acid sequence |
| 46 | anti-BTLA 21H6 $V_{K1}$ nucleotide sequence |
| 47 | anti-BTLA 21H6 $V_{K1}$ amino acid sequence |
| 48 | anti-BTLA 21H6 $V_{K2}$ nucleotide sequence |
| 49 | anti-BTLA 21H6 $V_{K2}$ amino acid sequence |
| 50 | anti-BTLA 21H6 $V_{K3}$ nucleotide sequence |
| 51 | anti-BTLA 21H6 $V_{K3}$ amino acid sequence |
| 52 | anti-BTLA 8A3 VH nucleotide sequence |
| 53 | anti-BTLA 8A3 VH amino acid sequence |
| 54 | anti-BTLA 8A3 $V_K$ nucleotide sequence |
| 55 | anti-BTLA 8A3 $V_K$ amino acid sequence |
| 56 | anti-BTLA 19A7 VH nucleotide sequence |
| 57 | anti-BTLA 19A7 VH amino acid sequence |
| 58 | anti-BTLA 19A7 $V_K$ nucleotide sequence |
| 59 | anti-BTLA 19A7 $V_K$ amino acid sequence |
| 60 | anti-BTLA 20H4 VH nucleotide sequence |
| 61 | anti-BTLA 20H4 VH amino acid sequence |
| 62 | anti-BTLA 20H4 $V_K$ nucleotide sequence |
| 63 | anti-BTLA 20H4 $V_K$ amino acid sequence |
| 64 | anti-BTLA 15C5 VH nucleotide sequence |
| 65 | anti-BTLA 15C5 VH amino acid sequence |
| 66 | anti-BTLA 15C5 $V_K$ nucleotide sequence |
| 67 | anti-BTLA 15C5 $V_K$ amino acid sequence |

REFERENCES

Ansari M J, Salama A D, Chitnis T, Smith R N, Yagita H, Akiba H, et al. The programmed death-1 (PD-1) pathway regulates autoimmune diabetes in nonobese diabetic (NOD) mice. J Exp Med. 2003; 198:63-9.

Compaan D M, Gonzalez L C, Tom I, Loyet K M, Eaton D, Hymowitz S G. Attenuating lymphocyte activity: the crystal structure of the BTLA-HVEM complex. J Biol. Chem. 2005; 280:39553-61.

Deppong C, Juehne T I, Hurchla M, Friend L D, Shah D D, Rose C M, et al. Cutting edge: B and T lymphocyte attenuator and programmed death receptor-1 inhibitory receptors are required for termination of acute allergic airway inflammation. J. Immunol. 2006; 176:3909-13.

Han P, Goularte O D, Rufner K, Wilkinson B, Kaye J. An inhibitory Ig superfamily protein expressed by lymphocytes and APCs is also an early marker of thymocyte positive selection. J. Immunol. 2004; 172:5931-9.

Harrop J A, McDonnell P C, Brigham-Burke M, Lyn S D, Minton J, Tan K B, et al. Herpesvirus entry mediator ligand (HVEM-L), a novel ligand for HVEM/TR2, stimulates proliferation of T cells and inhibits HT29 cell growth. J Biol. Chem. 1998; 273:27548-56.

Lin S C, Kuo C C, Chan C H. Association of a BTLA gene polymorphism with the risk of rheumatoid arthritis. J Biomed Sci. 2006; 13:853-60.

Oya Y, Watanabe N, Owada T, Oki M, Hirose K, Suto A, et al. Development of autoimmune hepatitis-like disease and production of autoantibodies to nuclear antigens in mice lacking B and T lymphocyte attenuator. Arthritis Rheum. 2008; 58:2498-510.

Presta L G. Engineering antibodies for therapy. Curr. Pharm. Biotechnol. 2002; 3:237-256.

Sedy J R, Gavrieli M, Potter K G, Hurchla M A, Lindsley R C, Hildner K, et al. B and T lymphocyte attenuator regulates T cell activation through interaction with herpesvirus entry mediator. Nat. Immunol. 2005; 6:90-8.

Stebbings R, Findlay L, Edwards C, Eastwood D, Bird C, North D, et al. "Cytokine storm" in the phase I trial of monoclonal antibody TGN1412: better understanding the causes to improve preclinical testing of immunotherapeutics. J. Immunol. 2007; 179:3325-31.

Steinberg M W, Turovskaya O, Shaikh R B, Kim G, McCole D F, Pfeffer K, et al. A crucial role for HVEM and BTLA in preventing intestinal inflammation. J Exp Med. 2008; 205: 1463-76.

Truong W, Plester J C, Hancock W W, Merani S, Murphy T L, Murphy K M, et al. Combined coinhibitory and costimulatory modulation with anti-BTLA and CTLA4Ig facilitates tolerance in murine islet allografts. Am J. Transplant. 2007; 7:2663-74.

Truong W, Hancock W W, Plester J C, Merani S, Rayner D C, Thangavelu G, Murphy K M, et al. BTLA targeting modulates lymphocyte phenotype, function, and numbers and attenuates disease in nonobese diabetic mice. J Leukoc Biol. 2009.

Vendel A C, Calemine-Fenaux J, Izrael-Tomasevic A, Chauhan V, Arnott D, Eaton D L. B and T lymphocyte attenuator regulates B cell receptor signaling by targeting Syk and BLNK. J. Immunol. 2009; 182:1509-17.

Watanabe N, Gavrieli M, Sedy J R, Yang J, Fallarino F, Loftin S K, et al. BTLA is a lymphocyte inhibitory receptor with similarities to CTLA-4 and PD-1. Nat Immunol 2003; 4:670-9.

Derré, L, Rivals, J-P, Jandus, C, Pastor, S., Rimoldi, D, Romero, P., Michielin, O., Olive, D, and Speiser D. BTLA Mediates inhibition of human tumor-specific CD8+ T cells that can be partially reversed by vaccination. J. ClinI. Invest. 2010, 120:157-167.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, Genbank Accession Numbers and publications are cited throughout this application, the disclosures of which, particularly, including all disclosed chemical structures and antibody amino acid sequences therein, are incorporated herein by reference. Citation of the above publications or documents is not intended as an admission that any of the foregoing is pertinent prior art, nor does it constitute any admission as to the contents or date of these publications or documents. All references cited herein are incorporated by reference to the same extent as if each individual publication, patent application, or patent, was specifically and individually indicated to be incorporated by reference.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

What is claimed is:

1. An isolated nucleic acid comprising a nucleotide sequence encoding heavy and light chain variable regions of an antibody, or antigen binding fragment thereof, wherein the heavy and light variable regions comprise the amino acid sequences set forth in SEQ ID NOs:25 and 32, respectively.

2. An expression vector comprising the isolated nucleic acid of claim 1.

3. An isolated host cell comprising the expression vector of claim 2.

4. A method of producing an antibody, or antigen binding fragment thereof, comprising:
   a. culturing the host cell of claim 3 in culture medium under conditions wherein the nucleic acid sequence is expressed, thereby producing a polypeptide comprising the light and heavy chain variable regions; and
   b. recovering the polypeptides from the host cell or culture medium.

5. An isolated nucleic acid comprising a nucleotide sequence encoding an anti-BTLA antibody variable region, wherein the antibody variable region is at least 95% identical to SEQ ID NO:25.

6. An isolated nucleic acid comprising a nucleotide sequence encoding an anti-BTLA antibody variable region, wherein the antibody variable region is at least 95% identical to SEQ ID NO:32.

7. An isolated nucleic acid comprising a nucleotide sequence encoding a heavy chain variable region as set forth in SEQ ID NO:25.

8. An isolated nucleic acid comprising a nucleotide sequence encoding a light chain variable region as set forth in SEQ ID NO:32.

9. An isolated nucleic acid comprising a nucleotide sequence set forth in SEQ ID NO:24.

10. An isolated nucleic acid comprising a nucleotide sequence set forth in SEQ ID NO:31.

11. An expression vector comprising the isolated nucleic acid of claim 5.

12. An isolated host cell comprising the expression vector of claim 11.

13. An expression vector comprising the isolated nucleic acid of claim 6.

14. An isolated host cell comprising the expression vector of claim 13.

15. An expression vector comprising the isolated nucleic acid of claim 7.

16. An isolated host cell comprising the expression vector of claim 15.

17. An expression vector comprising the isolated nucleic acid of claim 8.

18. An isolated host cell comprising the expression vector of claim 17.

19. An expression vector comprising the isolated nucleic acid of claim 9.

20. An isolated host cell comprising the expression vector of claim 19.

21. An expression vector comprising the isolated nucleic acid of claim 10.

22. An isolated host cell comprising the expression vector of claim 21.

* * * * *